United States Patent
Fretz et al.

(10) Patent No.: US 8,143,304 B2
(45) Date of Patent: Mar. 27, 2012

(54) (3-AMINO-1,2,3,4-TETRAHYDRO-9 H-CARBAZOL-9-YL)-ACETIC ACID DERIVATIVES

(75) Inventors: Heinz Fretz, Riehen (CH); Julien Pothier, Saint-Louis (FR); Philippe Risch, Zaessingue (FR)

(73) Assignee: Actelion Pharmaceutical Ltd., Allschwil (CH)

( * ) Notice: Subject to any disclaimer, the term of this patent is extended or adjusted under 35 U.S.C. 154(b) by 444 days.

(21) Appl. No.: 12/376,932

(22) PCT Filed: Aug. 2, 2007

(86) PCT No.: PCT/IB2007/053046
§ 371 (c)(1),
(2), (4) Date: Feb. 9, 2009

(87) PCT Pub. No.: WO2008/017989
PCT Pub. Date: Feb. 14, 2008

(65) Prior Publication Data
US 2010/0190830 A1    Jul. 29, 2010

(30) Foreign Application Priority Data

Aug. 7, 2006 (WO) .................. PCT/IB2006/052723

(51) Int. Cl.
A01N 43/38 (2006.01)
A61K 31/40 (2006.01)
C07C 49/00 (2006.01)
C07D 209/94 (2006.01)
C07D 487/00 (2006.01)
C07D 491/00 (2006.01)
C07D 513/00 (2006.01)

(52) U.S. Cl. ......... 514/411; 564/308; 548/439; 540/479
(58) Field of Classification Search .................. 514/411; 540/479; 548/439; 564/308
See application file for complete search history.

(56) References Cited

U.S. PATENT DOCUMENTS

| | | | |
|---|---|---|---|
| 4,808,608 A | 2/1989 | Guindon et al. | |
| 4,965,258 A | 10/1990 | Boshagen et al. | |
| 2005/0171143 A1 | 8/2005 | Tanimoto et al. | |

FOREIGN PATENT DOCUMENTS

| | | |
|---|---|---|
| EP | 0 242 518 | 10/1987 |
| EP | 1 505 061 | 2/2005 |
| EP | 1 505 061 A | 2/2005 |
| GB | 2 388 540 | 11/2003 |
| GB | 2 388 540 A | 11/2003 |
| GB | 2 407 318 | 4/2005 |
| GB | 2 422 829 | 8/2006 |
| GB | 2 422 830 | 8/2006 |
| GB | 2 422 831 | 8/2006 |
| WO | WO 01/79169 | 10/2001 |
| WO | WO 02/094830 | 11/2002 |
| WO | WO 03/051837 | 6/2003 |
| WO | WO 03051837 A3 * | 6/2003 |
| WO | WO 03/062200 | 7/2003 |
| WO | WO 03/066046 | 8/2003 |
| WO | WO 03/066047 | 8/2003 |
| WO | WO 03/097042 | 11/2003 |
| WO | WO 03/097598 | 11/2003 |
| WO | WO 03/101961 | 12/2003 |
| WO | WO 03/101981 | 12/2003 |
| WO | WO 2004/007451 | 1/2004 |
| WO | WO 2004/039807 | 5/2004 |
| WO | WO 2004/078719 | 9/2004 |
| WO | WO 2004/103970 | 12/2004 |
| WO | WO 2004/106302 | 12/2004 |
| WO | WO 2004/111047 | 12/2004 |
| WO | WO 2005/019171 | 3/2005 |
| WO | WO 2005/033099 | 4/2005 |
| WO | WO 2005/040112 | 5/2005 |
| WO | WO 2005/040114 | 5/2005 |
| WO | WO 2005/044260 | 5/2005 |
| WO | WO 2005/054232 | 6/2005 |
| WO | WO 2005/056527 | 6/2005 |
| WO | WO 2005/073234 | 8/2005 |
| WO | WO 2005/094816 | 10/2005 |
| WO | WO 2005/095397 | 10/2005 |
| WO | WO 2005/121141 | 12/2005 |
| WO | WO 2005/123731 | 12/2005 |

(Continued)

OTHER PUBLICATIONS

International Search Report (Form PCT/ISA/210) in PCT/IB2007/053046.

(Continued)

Primary Examiner — Sreeni Padmanabhan
Assistant Examiner — Kendra D Carter
(74) Attorney, Agent, or Firm — Hunton & Williams LLP

(57) ABSTRACT

The present invention relates to (3-amino-1,2,3,4-tetrahydro-9H-carbazol-9-yl)-acetic acid derivatives of Formula (I) wherein $R^1$, $R^2$, $R^3$, $R^4$, $R^5$ and $R^6$ are as described in the description and their use as prostaglandin receptor modulators, most particularly as prostaglandin $D_2$ receptor modulators, in the treatment of various prostaglandin-mediated diseases and disorders, to pharmaceutical compositions containing these compounds and to processes for their preparation.

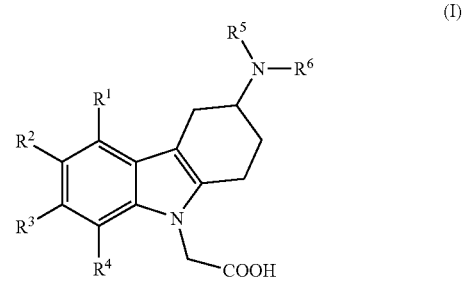

(I)

23 Claims, No Drawings

FOREIGN PATENT DOCUMENTS

| | | |
|---|---|---|
| WO | WO 2006/021418 | 3/2006 |
| WO | WO 2006/034418 | 3/2006 |
| WO | WO 2006/034419 | 3/2006 |
| WO | WO 2006/036994 | 4/2006 |
| WO | WO 2006/070325 | 7/2006 |
| WO | WO 2006/081343 | 8/2006 |
| WO | WO 2006/090817 | 8/2006 |
| WO | WO 2006/092579 | 9/2006 |
| WO | WO 2006/095183 | 9/2006 |
| WO | WO 2006/125784 | 11/2006 |
| WO | WO 2006/136859 | 12/2006 |
| WO | WO 2007/010964 | 1/2007 |
| WO | WO 2007/010965 | 1/2007 |
| WO | WO 2007/019675 | 2/2007 |
| WO | WO 2007/022501 | 2/2007 |
| WO | WO 2007/029629 | 3/2007 |
| WO | WO 2007/031747 | 3/2007 |
| WO | WO 2007/045867 | 4/2007 |
| WO | WO 2007/065683 | 6/2007 |
| WO | WO 2007/065684 | 6/2007 |
| WO | WO 2007/065924 | 6/2007 |
| WO | WO 2007/068418 | 6/2007 |

OTHER PUBLICATIONS

Written Opinion of the International Searching Authority (Form PCT/ISA/237) in PCT/IB2007/053046.

Arimura, A. et al, "Prevention of Allergic Inflammation by a Novel Prostaglandin Receptor Antagonist, S-5751", Journal of Pharmacology and Experimental Therapeutics, Feb. 2001, 298(2), pp. 411-419.

Conrow, R. et al., "Efficient Preparation of Polyfunctional .alpha.-diketones from Carboxylic Acids", The Journal of Organic Chemistry, 51(6), pp. 938-940, Rec'd. Sep. 1985.

Gennaro, A., "Remington: The Science and Practice of Pharmacy", 20th Edition, Philadelphia College of Pharmacy and Science, (2001).

Gibson, M., "Pharmaceutical Preformulation and Formulation", IHS Health Group, Englewood, GO, USA, ISBN: 1574911201, (2001).

Gould, P., "Salt Selction for Basic Drugs", International Journal of Pharmaceutics, vol. 33, pp. 201-217, Mar. 24, 1986.

Greene, "Protective Groups in Organic Synthesis", T.W. Greene, P.G.M. Wuts, Wiley InterScience, (1999).

Ha, J.D. et al., Synthesis of Tetrahydrocarbazole Derivatives as Potent β3-Adrenoceptor Agonists, Bulletin of the Korean Soc. Chem., 25, pp. 1784-1790, Rec'd. Jul. 2004.

Ishizuka, T. et al, "Ramatroban (BAY u 3405): A Novel Dual Antagonist of $TXA_2$ Receptor and $CRTh_2$, a Newly Identified Prostaglandin $D_2$ Receptor", Cardiovascular Drug Rev., 22(2), pp. 71-90, (2004).

Larock R. C. in "Comprehensive Organic Transformations: A Guide to Functional Group Preparations", VCH Publishers, (1999).

Miller, S.C. et al., "Site-Selective N-Methylation of Peptides on Solid Support", Journal of the American Chemical Society, vol. 119, pp. 2301-2302, Rec'd. (1997).

Pena, C. et al., Solvent Dependent Selective Alkylation of a Bis-(Sulfonamide) for the Synthesis of a DNA-Binding Chiral Polyamine, Tetrahedron Letters, 46, pp. 2783-2787, Rec'd. Jan. 2005.

Rosentreter, U. et al., Synthesis and Absolute Configuration of the New Thromboxane Antagonist (3R)-3-(4-Fluorophenylsulfonamido)-1,2,3,4-Tetrahydro-9-Carbazolepropanoic Acid and Comparison with its Enantiomer, Arzneim.-Forsch., 39(12), 1519-1521 (1989).

Sawyer N. et al., "Molecular Pharmacology of the Human Prostaglandin $D_2$ Receptor. CRTH2", British Journal Pharmacology, 137, pp. 1163-1172, (2002).

Sugimoto, H., An Orally Bioavailable Small Molecule Antagonist of CRTH2, Ramatroban (BAY u3405), Inhibits Prostaglandin $D_2$-Induced Eosinophil Migration in Vitro, Journal of Pharmacology and Experimental Therapeutics, 305(1), p. 347-352 (2003).

Ulven et al, "Minor Structural Modifications Convert the Dual TP/CRTH2 Antagonist Ramatroban Into a Highly Selective and Potent CRTH2 Antagonist", Journal of Medicinal Chemistry, 48(4), pp. 897-900, Feb. 2005.

Block et al., Journal of Medicinal Chemistry, vol. 45, pp. 3509-3523 (2002).

Robarge et al., Bioorganic & Medicinal Chemistry Letters, vol. 15, pp. 1749-1753 (2005).

* cited by examiner

(3-AMINO-1,2,3,4-TETRAHYDRO-9 H-CARBAZOL-9-YL)-ACETIC ACID DERIVATIVES

CROSS-REFERENCE TO RELATED APPLICATIONS

This application is the U.S. National Phase Application of International Application No. PCT/IB2007/053046, filed Aug. 2, 2007, which claims the benefit of PCT/IB2006/052723, filed Aug. 7, 2006, the disclosures of each of which is incorporated by reference.

FIELD OF THE INVENTION

The present invention relates to (3-amino-1,2,3,4-tetrahydro-9H-carbazol-9-yl)-acetic acid derivatives of Formula I and their use as prostaglandin receptor modulators, most particularly as prostaglandin $D_2$ receptor ("DP receptor") modulators, in the treatment of various prostaglandin-mediated diseases and disorders, to pharmaceutical compositions containing these compounds and to processes for their preparation. In particular, such derivatives may be used alone or in pharmaceutical compositions for the treatment of both, chronic and acute allergic/immune diseases/disorders such as allergic asthma, rhinitis, allergic rhinitis, chronic obstructive pulmonary disease (COPD), dermatitis, inflammatory bowel disease, rheumatoid arthritis, allergic nephritis, conjunctivitis, atopic dermatitis, bronchial asthma, food allergy, systemic mast cell disorders, anaphylactic shock, urticaria, eczema, itching, inflammation, ischemia-reperfusion injury, cerebrovascular disorders, pleuritis, ulcerative colitis, eosinophil-related diseases, such as Churg-Strauss syndrome and sinusitis, and basophil-related diseases, such as basophilic leukemia and basophilic leukocytosis, in humans and other mammals.

BACKGROUND OF THE INVENTION

As a response to allergen exposure in allergic conditions, mast cells are activated and release chemotactic key mediators like histamine, thromboxane A2 (TxA2), cysteinyl leukotrienes (CysLTs) and prostaglandin $D_2$ ($PGD_2$). These mediators interact with their respective receptors and cause physiological effects such as increased vascular permeability, edema, pruritus, nasal and pulmonary congestion, bronchoconstriction, and mucus secretion. An increased vascular permeability for example, allows excessive infiltration of eosinophilic and basophilic leukocytes into the tissue and thus amplifies the allergic response.

Current treatments of allergic diseases comprise agents that can block or otherwise interrupt such interactions, e.g. anti-histamines (histamine H1 receptor antagonists), leukotriene receptor antagonists, beta-adrenergic receptor agonists, and corticosteroids. Generally, treatments with anti-histamines and leukotriene antagonists are limited in efficacy, and long-term usage of corticosteroids is associated with unwanted side effects.

$PGD_2$ is an agonist known to act on two G-protein-coupled receptors, the $PGD_2$ receptor DP1 and the recently identified CRTH2 (chemoattractant receptor-homologous molecule expressed on Th2 cells) receptor (also referred to as "DP2 receptor").

Elevated $PGD_2$ levels are considered to cause inflammation actions as observed in allergic diseases such as allergic rhinitis, allergic asthma, allergic conjunctivitis, atopic dermatitis and the like. Therefore, blocking the interaction of $PGD_2$ with its receptors is considered a useful therapeutic strategy for the treatment of such diseases.

WO 01/79169 discloses (tetrahydrocarbazol-1-yl)acetic acid derivatives as $PGD_2$ receptor antagonists.

GB 2388540 (Bayer AG) discloses the use of ramatroban ((3R)-3-(4-fluorobenzene-sulfonamido)-1,2,3,4-tetrahydrocarbazole-9-propionic acid), a TxA2 receptor (also referred to as "TP receptor") antagonist with additional antagonistic activity on CRTH2, for the prophylaxis and treatment of allergic diseases, such as asthma, allergic rhinitis or allergic conjunctivitis. In T. Ishizuka et al., *Cardiovascular Drug Rev.* 2004, 22(2), 71-90 effects of ramatroban on late-phase inflammation are described. Furthermore, oral bioavailability of ramatroban and its ability to inhibit prostaglandin $D_2$-induced eosinophil migration in vitro has been reported (*Journal of Pharmacology and Experimental Therapeutics,* 305 (1), p. 347-352 (2003)).

WO 03/097598 and WO 03/097042 disclose Ramatroban analogues with CRTH2 antagonistic activity. Ulven et al, in *J. Med. Chem.* 2005, 48(4), 897-900 disclose further ramatroban analogues.

The compounds of the invention are structurally different from corticosteroids, anti-histamines, leukotriene antagonists or beta-adrenergic agonists.

DESCRIPTION OF THE INVENTION i) The present invention relates to (3-amino-1,2,3,4-tetrahydro-9H-carbazol-9-yl)-acetic acid compounds of the Formula I:

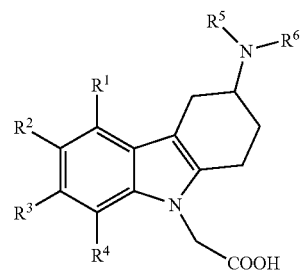

wherein $R^1$, $R^2$, $R^3$ and $R^4$ independently represent hydrogen, $C_{1-5}$-alkyl, $C_{1-5}$-alkoxy, alkenyl (especially allyl or vinyl), halogen, nitro, cyano, halo-$C_{1-6}$-alkoxy, halo-$C_{1-6}$-alkyl, $C_{1-6}$-alkylsulfonyl, or formyl;

$R^5$ represents hydrogen, alkenyl (especially allyl or vinyl), $C_{1-6}$-alkyl, cycloalkyl-$C_{1-4}$-alkyl, $C_{1-3}$-alkoxy-$C_{1-4}$-alkyl, aryl-$C_{1-4}$-alkyl, or aryloxy-$C_{1-4}$-alkyl (especially $R^5$ represents hydrogen, $C_{1-6}$-alkyl, cycloalkyl-$C_{1-4}$-alkyl, $C_{1-3}$-alkoxy-$C_{1-4}$-alkyl, aryl-$C_{1-4}$-alkyl, or aryloxy-$C_{1-4}$-alkyl);

wherein aryl is unsubstituted, mono- or di-substituted with a group independently selected from $C_{1-2}$-alkylendioxy, $C_{1-4}$-alkoxy, $C_{1-4}$-alkyl, halogen, trifluoromethyl, and trifluoromethoxy (especially trifluoromethyl); and $R^6$ represents $C_{1-9}$-alkylaminocarbonyl; $C_{1-9}$-alkylaminothiocarbonyl; $C_{1-9}$-alkylcarbonyl; $C_{1-9}$-alkoxycarbonyl; arylalkenylcarbonyl; arylaminocarbonyl; arylaminothiocarbonyl; aryl-$C_{1-3}$-alkoxy-$C_{1-3}$-alkoxycarbonyl; aryl-$C_{1-3}$-alkoxycarbonyl; aryl-$C_{1-3}$-alkylamino carbonyl; aryl-$C_{1-6}$-alkylcarbonyl; aryl-$C_{1-3}$-alkoxy-$C_{1-3}$-alkylcarbonyl; arylcarbonyl; arylcarbonyl-$C_{1-4}$-alkylcarbonyl; aryloxy-$C_{1-3}$-alkylcarbonyl; aryl sulfonylamino carbonyl; cycloalkyl- $C_{1-3}$-alkylcarbonyl; diaryl-$C_{1-3}$-alkylcarbonyl; heterocyclylcarbonyl; heteroaryl-$C_{1-3}$-alkylcarbonyl; heteroarylcarbonyl; aryl-$C_{3-6}$-cycloalkylcarbonyl; cycloalkylcarbonyl; or $R^7$—$C_{1-4}$-alkylcarbonyl, wherein the bridging $C_{1-4}$-alkyl group may additionally be mono-substituted with aryl or disubstituted with hydroxy, and $R^7$ represents arylaminocarbonyl, heteroarylaminocarbonyl, $C_{1-6}$-alkylaminocarbonyl, or aryl-$C_{1-3}$-alkylaminocarbonyl;

wherein aryl is unsubstituted, mono- or di-substituted with a group independently selected from $C_{1-2}$-alkylendioxy; $C_{1-6}$-alkoxy; $C_{1-6}$-alkyl; $C_{1-6}$-alkylsulfonyl; phenyl which is unsubstituted, mono- or di-substituted by substituents independently selected from halogen, trifluoromethyl, methoxy and methyl; naphthyl; phenyl-$C_{1-3}$-alkyl, wherein the phenyl group is unsubstituted, mono- or di-substituted with substituents independently selected from halogen, trifluoromethyl, methoxy and methyl; naphthyl-$C_{1-3}$-alkyl; phenoxy, wherein the phenyl group is unsubstituted, mono- or di-substituted with substituents independently selected from halogen, trifluoromethyl, methoxy and methyl; naphthyloxy; halogen; hydroxy; halo-$C_{1-6}$-alkyl; halo-$C_{1-6}$-alkoxy; $C_{1-6}$-alkylthio; and $C_{1-4}$-alkoxycarbonylamino.

ii) In another embodiment, the invention relates to compounds of Formula I according to embodiment i), wherein $R^5$ represents hydrogen, alkenyl (especially allyl or vinyl), or $C_{1-6}$-alkyl; and $R^6$ represents $C_{1-9}$-alkylaminocarbonyl, $C_{1-9}$-alkylaminothiocarbonyl, $C_{1-9}$-alkylcarbonyl, $C_{1-9}$-alkoxycarbonyl, arylalkenylcarbonyl, arylaminocarbonyl, arylaminothiocarbonyl, aryl-$C_{1-3}$-alkoxy-$C_{1-3}$-alkoxycarbonyl, aryl-$C_{1-3}$-alkoxycarbonyl, aryl-$C_{1-3}$-alkylamino carbonyl, aryl-$C_{1-3}$-alkylcarbonyl, aryl-$C_{1-3}$-alkoxy-$C_{1-3}$-alkylcarbonyl, arylcarbonyl, arylcarbonyl-$C_{1-4}$-alkylcarbonyl, aryloxy-$C_{1-3}$-alkylcarbonyl, arylsulfonylaminocarbonyl, cycloalkyl-$C_{1-3}$-alkylcarbonyl, diaryl-$C_{1-3}$-alkylcarbonyl, heterocyclylcarbonyl, heteroaryl-$C_{1-3}$-alkylcarbonyl, or heteroarylcarbonyl;

wherein aryl is unsubstituted, mono- or di-substituted with a group independently selected from $C_{1-2}$-alkylendioxy; $C_{1-6}$-alkoxy; $C_{1-6}$-alkyl; $C_{1-6}$-alkylsulfonyl; phenyl which is unsubstituted, mono- or di-substituted with substituents independently selected from halogen, trifluoromethyl, methoxy and methyl; naphthyl; phenyl-$C_{1-3}$-alkyl, wherein the phenyl group is unsubstituted, mono- or di-substituted with substituents independently selected from halogen, trifluoromethyl, methoxy and methyl; naphthyl-$C_{1-3}$-alkyl; phenoxy, wherein the phenyl group is unsubstituted, mono- or di-substituted with substituents independently selected from halogen, trifluoromethyl, methoxy and methyl; naphthyloxy; halogen; hydroxy; halo-$C_{1-6}$-alkyl; and halo-$C_{1-6}$-alkoxy.

iii) A further embodiment of the invention relates to compounds of Formula I according to embodiment ii), wherein $R^1$, $R^2$, $R^3$ and $R^4$ independently represent hydrogen; $C_{1-5}$-alkyl, especially methyl, or isopropyl; $C_{1-5}$-alkoxy, especially methoxy; alkenyl, especially allyl or vinyl; halogen, especially fluoro, or chloro; halo-$C_{1-6}$-alkyl, especially trifluoromethyl; or $C_{1-6}$-alkylsulfonyl, especially methanesulfonyl;

$R^5$ represents hydrogen; alkenyl, especially ethenyl, or 2-propenyl; or $C_{1-6}$-alkyl, especially methyl, ethyl, or propyl; and $R^6$ represents $C_{1-9}$-alkylaminocarbonyl, such as butylaminocarbonyl; $C_{1-9}$-alkylcarbonyl, such as propylcarbonyl, isobutylcarbonyl, hexylcarbonyl, or nonylcarbonyl; $C_{1-9}$-alkoxycarbonyl, such as propoxycarbonyl, tert-butoxycarbonyl, or isobutoxycarbonyl; arylalkenylcarbonyl, such as naphthalenylethenylcarbonyl (especially 2-naphthalen-2-yl-ethenylcarbonyl), or phenylethenylcarbonyl; arylamino carbonyl, such as naphthalenaminocarbonyl (especially naphthalen-1-amino carbonyl), or phenylaminocarbonyl; aryl-$C_{1-3}$-alkoxy-$C_{1-3}$-alkoxycarbonyl, such as benzyloxyethoxycarbonyl (especially 2-benzyloxy-ethoxycarbonyl); aryl-$C_{1-3}$-alkoxycarbonyl, such as benzyloxycarbonyl; aryl-$C_{1-3}$-alkylaminocarbonyl, such as benzylaminocarbonyl, or phenylethylaminocarbonyl; aryl-$C_{1-3}$-alkylcarbonyl, such as phenylmethylcarbonyl, phenylethylcarbonyl (especially 2-phenylethyl-carbonyl), or naphthalenylethylcarbonyl (especially 2-naphthalen-2-yl-ethylcarbonyl); aryl-$C_{1-3}$-alkoxy-$C_{1-3}$-alkylcarbonyl, such as benzyloxymethyl-carbonyl; arylcarbonyl, such as phenylcarbonyl; arylcarbonyl-$C_{1-4}$-alkylcarbonyl, such as phenylcarbonylethylcarbonyl (especially 2-phenylcarbonyl-ethylcarbonyl); aryloxy-$C_{1-3}$-alkylcarbonyl, such as phenoxymethylcarbonyl; arylsulfonylaminocarbonyl, such as phenylsulfonylaminocarbonyl; cycloalkyl-$C_{1-3}$-alkylcarbonyl, such as cyclopentylethylcarbonyl (especially 2-cyclopentylethylcarbonyl), or indanylmethylcarbonyl (especially indan-2-ylmethylcarbonyl); diaryl-$C_{1-3}$-alkylcarbonyl, such as 1,2-diphenylethylcarbonyl, or 2,2-diphenylethylcarbonyl; heterocyclylcarbonyl, such as dihydroindolylcarbonyl (especially 2,3-dihydro-1H-indole-2-carbonyl); heteroaryl-$C_{1-3}$-alkylcarbonyl, such as benzimidazolyl-$C_{1-3}$-alkylcarbonyl (especially 2-1H-benzimidazol-2-yl-ethylcarbonyl), or indolyl-$C_{1-3}$-alkylcarbonyl, such as indolylethylcarbonyl (especially 2-1H-indol-3-yl-ethylcarbonyl), or thienylmethylcarbonyl (especially 2-thienylmethylcarbonyl), or pyridinylethylcarbonyl (especially 2-(pyridin-3-yl)ethylcarbonyl); or heteroarylcarbonyl, such as indolylcarbonyl (especially 1H-indole-2-yl-carbonyl);

wherein aryl (especially phenyl or naphthyl) is unsubstituted, mono- or di-substituted with (a) group(s) independently selected from $C_{1-2}$-alkylendioxy (especially methylendioxy), $C_{1-6}$-alkoxy (especially methoxy), $C_{1-6}$-alkyl (especially methyl, ethyl, isopropyl, or tert-butyl), $C_{1-6}$-alkylsulfonyl (especially methanesulfonyl), halogen (especially chloro, fluoro or bromo), hydroxy, and halo-$C_{1-6}$-alkyl (especially trifluoromethyl).

iv) A further embodiment of the invention relates to compounds of Formula I according to any one of embodiments i) to iii), wherein $R^1$ represents hydrogen, or halogen.

v) A further embodiment of the invention relates to compounds of Formula I according to any one of embodiments i) to iv), wherein $R^2$ represents hydrogen, trifluoromethyl, or halogen (especially hydrogen, or halogen).

vi) A further embodiment of the invention relates to compounds of Formula I according to any one of embodiments i) to v), wherein $R^3$ represents hydrogen, or halogen.

vii) A further embodiment of the invention relates to compounds of Formula I according to any one of embodiments i) to vi), wherein $R^4$ represents hydrogen, alkenyl (especially allyl or vinyl), halogen (especially chloro or bromo), $C_{1-6}$-alkylsulfonyl (especially methanesulfonyl); especially hydrogen or halogen.

viii) A further embodiment of the invention relates to compounds of Formula I according to any one of embodiments i) to vii), wherein $R^1$, $R^3$ and $R^4$ represent hydrogen.

ix) A further embodiment of the invention relates to compounds of Formula I according to any one of embodiments i) to viii), wherein $R^2$ represents fluoro.

x) A further embodiment of the invention relates to compounds of Formula I according to any one of embodiments i) and iv) to ix), wherein $R^5$ represents hydrogen, $C_{1-6}$-alkyl (especially $C_{1-3}$-alkyl), cycloalkyl-$C_{1-4}$-alkyl (especially cyclopropylmethyl), $C_{1-3}$-alkoxy-$C_{1-4}$-alkyl (especially 2-methoxyethyl), aryl-$C_{1-4}$-alkyl (especially naphthylmethyl, or preferably phenyl-$C_{2-3}$-alkyl), or aryloxy-$C_{1-4}$-alkyl (especially phenoxyethyl); wherein aryl (especially phenyl) is unsubstituted (preferred), or mono- or di-substituted with a group independently selected from $C_{1-2}$-alkylendioxy, $C_{1-4}$-alkoxy, $C_{1-4}$-alkyl, halogen, trifluoromethyl, and trifluoromethoxy.

xi) A further embodiment of the invention relates to compounds of Formula I according to any one of embodiments i) and iv) to ix), wherein $R^5$ represents hydrogen; $C_{1-3}$-alkyl (especially methyl); cyclopropylmethyl; 2-methoxyethyl; phenyl-$C_{2-3}$-alkyl; or phenoxyethyl, wherein the phenyl group is unsubstituted (preferred), or mono-substituted with a group selected from $C_{1-2}$-alkylendioxy, $C_{1-4}$-alkoxy, $C_{1-4}$-alkyl, halogen, trifluoromethyl, and trifluoromethoxy (especially trifluoromethyl).

xii) A further embodiment of the invention relates to compounds of Formula I according to any one of embodiments i) and iv) to ix), wherein $R^5$ represents $C_{1-3}$-alkyl (especially methyl); cyclopropylmethyl; 2-methoxyethyl; phenyl-$C_{2-3}$-alkyl; or phenoxyethyl, wherein the phenyl group is unsubstituted (preferred), or mono-substituted with a group selected from $C_{1-2}$-alkylendioxy, $C_{1-4}$-alkoxy, $C_{1-4}$-alkyl, halogen, trifluoromethyl, and trifluoromethoxy (especially trifluoromethyl).

xiii) A further embodiment of the invention relates to compounds of Formula I according to any one of embodiments i) and iv) to ix), wherein $R^5$ represents hydrogen, $C_{1-3}$-alkyl (especially methyl), cyclopropylmethyl, or 2-methoxyethyl; especially cyclopropylmethyl, or 2-methoxyethyl.

xiv) A further embodiment of the invention relates to compounds of Formula I according to any one of embodiments i) and iv) to ix), wherein $R^5$ represents hydrogen, methyl, ethyl, or n-propyl.

xv) A further embodiment of the invention relates to compounds of Formula I according to any one of embodiments i) and iv) to ix), wherein $R^5$ represents hydrogen.

xvi) A further embodiment of the invention relates to compounds of Formula I according to any one of embodiments i) and iv) to ix), wherein $R^5$ represents phenyl-$C_{2-3}$-alkyl.

xvii) A further embodiment of the invention relates to compounds of Formula I according to any one of embodiments i) and iv) to xvi), wherein $R^6$ represents $C_{1-9}$-alkylaminocarbonyl; $C_{1-9}$-alkylcarbonyl; $C_{1-9}$-alkoxycarbonyl; arylalkenylcarbonyl; arylaminocarbonyl; aryl-$C_{1-3}$-alkoxy-$C_{1-3}$-alkoxycarbonyl; aryl-$C_{1-3}$-alkoxycarbonyl; aryl-$C_{1-3}$-alkylamino carbonyl; aryl-$C_{1-6}$-alkylcarbonyl; aryl-$C_{1-3}$-alkoxy-$C_{1-3}$-alkylcarbonyl; arylcarbonyl; arylcarbonyl-$C_{1-4}$-alkylcarbonyl; aryloxy-$C_{1-3}$-alkylcarbonyl; aryl sulfonylamino carbonyl; cyclo alkyl-$C_{1-3}$-alkylcarbonyl; diaryl-$C_{1-3}$-alkylcarbonyl; heterocyclylcarbonyl; heteroaryl-$C_{1-3}$-alkylcarbonyl; heteroarylcarbonyl; aryl-$C_{3-6}$-cycloalkylcarbonyl; cycloalkylcarbonyl; or $R^7$—$C_{1-4}$-alkylcarbonyl, wherein the bridging $C_{1-4}$-alkyl group may additionally be mono-substituted with aryl, and $R^7$ represents arylaminocarbonyl, heteroarylaminocarbonyl, $C_{1-6}$-alkylamino carbonyl, or aryl-$C_{1-3}$-alkylamino carbonyl;

wherein aryl is unsubstituted, mono- or di-substituted with a group independently selected from $C_{1-2}$-alkylendioxy, $C_{1-6}$-alkoxy, $C_{1-6}$-alkyl, $C_{1-6}$-alkylsulfonyl, halogen, hydroxy, halo-$C_{1-6}$-alkyl, halo-$C_{1-6}$-alkoxy, $C_{1-6}$-alkylthio, and $C_{1-4}$-alkoxycarbonylamino.

xviii) A further embodiment of the invention relates to compounds of Formula I according to any one of embodiments i) and iv) to xvi), wherein $R^6$ represents aryl-$C_{1-3}$-alkoxycarbonyl; aryl-$C_{1-3}$-alkylaminocarbonyl; aryl-$C_{1-6}$-alkylcarbonyl; aryl-$C_{1-3}$-alkoxy-$C_{1-3}$-alkylcarbonyl; arylcarbonyl-$C_{1-4}$-alkylcarbonyl; aryloxy-$C_{1-3}$-alkylcarbonyl; cycloalkyl-$C_{1-3}$-alkylcarbonyl; diaryl-$C_{1-3}$-alkylcarbonyl; aryl-$C_{3-6}$-cycloalkylcarbonyl; or $R^7$—$C_{1-4}$-alkylcarbonyl, wherein the bridging $C_{1-4}$-alkyl group may additionally be mono-substituted with aryl, and $R^7$ represents arylaminocarbonyl, heteroarylaminocarbonyl, $C_{1-6}$-alkylamino carbonyl, or aryl-$C_{1-3}$-alkylamino carbonyl;

wherein aryl is unsubstituted, mono- or di-substituted with a group independently selected from $C_{1-2}$-alkylendioxy, $C_{1-6}$-alkoxy, $C_{1-6}$-alkyl, $C_{1-6}$-alkylsulfonyl, halogen, hydroxy, halo-$C_{1-6}$-alkyl, halo-$C_{1-6}$-alkoxy, $C_{1-6}$-alkylthio, and $C_{1-4}$-alkoxycarbonylamino.

xix) A further embodiment of the invention relates to compounds of Formula I according to any one of embodiments i) and iv) to xvi), wherein $R^6$ represents aryl-$C_{1-3}$-alkoxycarbonyl; aryl-$C_{1-3}$-alkylamino carbonyl; aryl-$C_{1-6}$-alkylcarbonyl; aryloxy-$C_{1-3}$-alkylcarbonyl; diaryl-$C_{1-3}$-alkylcarbonyl; or $R^7$—$C_{1-4}$-alkylcarbonyl, wherein the bridging $C_{1-4}$-alkyl group may additionally be mono-substituted with aryl, and $R^7$ represents arylaminocarbonyl, or $C_{1-6}$-alkylamino carbonyl;

wherein aryl is unsubstituted, mono- or di-substituted with a group independently selected from $C_{1-2}$-alkylendioxy, $C_{1-6}$-alkoxy, $C_{1-6}$-alkyl, $C_{1-6}$-alkylsulfonyl, halogen, hydroxy, halo-$C_{1-6}$-alkyl, halo-$C_{1-6}$-alkoxy, $C_{1-6}$-alkylthio, and $C_{1-4}$-alkoxycarbonylamino.

xx) A further embodiment of the invention relates to compounds of Formula I according to any one of embodiments i) and iv) to xvi), wherein $R^6$ represents aryl-$C_{1-2}$-alkoxycarbonyl; aryl-$C_{1-2}$-alkylaminocarbonyl; aryl-$C_{1-4}$-alkylcarbonyl; aryloxy-$C_{1-2}$-alkylcarbonyl; or diaryl-$C_{2-3}$-alkylcarbonyl; or $R^7$—$C_{2-4}$-alkylcarbonyl, wherein the bridging $C_{2-4}$-alkyl group may additionally be mono-substituted with aryl, and $R^7$ represents arylaminocarbonyl, or $C_{1-4}$-alkylaminocarbonyl;

wherein aryl is unsubstituted, mono- or di-substituted with a group independently selected from $C_{1-2}$-alkylendioxy, $C_{1-6}$-alkoxy, $C_{1-6}$-alkyl, $C_{1-6}$-alkylsulfonyl, halogen, hydroxy, trifluoromethyl, and trifluoromethoxy.

xxi) A further embodiment of the invention relates to compounds of Formula I according to any one of embodiments i) and iv) to xvi), wherein $R^6$ represents aryl-$C_{1-2}$-alkylaminocarbonyl; wherein aryl is unsubstituted, mono- or di-substituted with a group independently selected from $C_{1-2}$-alkylendioxy, $C_{1-6}$-alkoxy, $C_{1-6}$-alkyl, $C_{1-6}$-alkylsulfonyl, halogen, hydroxy, trifluoromethyl, and trifluoromethoxy.

xxii) A further embodiment of the invention relates to compounds of Formula I according to any one of embodiments i) and iv) to xvi), wherein $R^6$ represents aryl-$C_{1-2}$-alkoxycarbonyl; aryl-$C_{1-4}$-alkylcarbonyl; aryloxy-$C_{1-2}$-alkylcarbonyl; or diaryl-$C_{2-3}$-alkylcarbonyl;

wherein aryl is unsubstituted, mono- or di-substituted with a group independently selected from $C_{1-2}$-alkylendioxy, $C_{1-6}$-alkoxy, $C_{1-6}$-alkyl, $C_{1-6}$-alkylsulfonyl, halogen, hydroxy, trifluoromethyl, and trifluoromethoxy.

xxiii) A further embodiment of the invention relates to compounds of Formula I according to any one of embodiments i) to xxii), wherein, in case $R^6$ represents a group which contains aryl, the aryl group is phenyl which unsubstituted, or mono- or di-substituted with a group independently selected from $C_{1-4}$-alkoxy, $C_{1-4}$-alkyl, halogen, and trifluoromethyl.

xxiv) A further embodiment of the invention relates to compounds of Formula I according to any one of embodiments i) and iv) to xvi), wherein $R^6$ represents $C_{1-4}$-alkylcarbonyl (especially acetyl); or aryl-$C_{2-4}$-alkylcarbonyl, wherein aryl is unsubstituted, mono- or di-substituted with a group independently selected from $C_{1-4}$-alkoxy, $C_{1-4}$-alkyl, halogen, and trifluoromethyl.

xxv) A further embodiment of the invention relates to compounds of Formula I according to any one of embodiments i)

and iv) to xvi), wherein $R^6$ represents aryl-$C_{2-4}$-alkylcarbonyl, wherein aryl is unsubstituted, mono- or di-substituted with a group independently selected from $C_{1-4}$-alkoxy, $C_{1-4}$-alkyl, halogen, and trifluoromethyl.

xxvi) A further embodiment of the invention relates to compounds of Formula I according to any one of embodiments i) to xxv), wherein, in case $R^6$ represents a group which contains a carbonyl group and one or more aryl moieties, said group is such that it contains a bridging group between the carbonyl group and said aryl moiety (moieties) of said $R^6$, wherein the carbonyl moiety and at least one of the aryl moieties are directly attached to different atoms of said bridging group.

xxvii) A further embodiment of the invention relates to compounds of Formula I according to any one of embodiments i) to xxv), wherein, in case $R^6$ represents a group which contains a carbonyl group and exactly one aryl moiety, said group is such that it contains a bridging group between the carbonyl group and said aryl moiety of said $R^6$, wherein the carbonyl moiety and the aryl moiety are directly attached to the same atom of said bridging group.

xxviii) A further embodiment of the invention relates to compounds of Formula I according to embodiment i), wherein $R^1$ represents hydrogen, or halogen;
$R^2$ represents hydrogen, trifluoromethyl, or halogen;
$R^3$ represents hydrogen, or halogen;
$R^4$ represents hydrogen, halogen (especially chloro or bromo), or $C_{1-6}$-alkylsulfonyl (especially methanesulfonyl);
$R^5$ represents hydrogen, $C_{1-6}$-alkyl, cycloalkyl-$C_{1-4}$-alkyl, $C_{1-3}$-alkoxy-$C_{1-4}$-alkyl, aryl-$C_{1-4}$-alkyl, or aryloxy-$C_{1-4}$-alkyl;
wherein aryl is unsubstituted, mono-substituted with a group selected from trifluoromethyl; and
$R^6$ represents $C_{1-9}$-alkylaminocarbonyl; $C_{1-9}$-alkylcarbonyl; $C_{1-9}$-alkoxycarbonyl; arylalkenylcarbonyl; arylaminocarbonyl; aryl-$C_{1-3}$-alkoxy-$C_{1-3}$-alkoxycarbonyl; aryl-$C_{1-3}$-alkoxycarbonyl; aryl-$C_{1-3}$-alkylaminocarbonyl; aryl-$C_{1-6}$-alkylcarbonyl; aryl-$C_{1-3}$-alkoxy-$C_{1-3}$-alkylcarbonyl; arylcarbonyl; arylcarbonyl-$C_{1-4}$-alkylcarbonyl; aryloxy-$C_{1-3}$-alkylcarbonyl; arylsulfonylaminocarbonyl; cycloalkyl-$C_{1-3}$-alkylcarbonyl; diaryl-$C_{1-3}$-alkylcarbonyl; heterocyclylcarbonyl; heteroaryl-$C_{1-3}$-alkylcarbonyl; heteroarylcarbonyl; aryl-$C_{3-6}$-cycloalkylcarbonyl; cycloalkylcarbonyl; or $R^7$—$C_{1-4}$-alkylcarbonyl, wherein the bridging $C_{1-4}$-alkyl group may additionally be mono-substituted with aryl or disubstituted with hydroxy, and $R^7$ represents arylaminocarbonyl, heteroarylaminocarbonyl, $C_{1-6}$-alkylamino carbonyl, or aryl-$C_{1-3}$-alkylamino carbonyl;
wherein aryl is unsubstituted, mono- or di-substituted with a group independently selected from $C_{1-2}$-alkylendioxy; $C_{1-6}$-alkoxy; $C_{1-6}$-alkyl; $C_{1-6}$-alkylsulfonyl; halogen; hydroxy; trifluoromethyl; trifluoromethoxy; $C_{1-6}$-alkylthio; and $C_{1-4}$-alkoxycarbonylamino.

xxix) A further embodiment of the invention relates to compounds of Formula I according to any one of embodiments i) to xxviii), wherein the position C(3) of the tetrahydrocarbazole ring of Formula I is (S)-configurated.

xxx) A further embodiment of the invention relates to compounds of Formula I according to any one of embodiments i) to xxviii), wherein the position C(3) of the tetrahydrocarbazole ring of Formula I is (R)-configurated.

In another embodiment preferred compounds of Formula I are selected from the group consisting of:
(3S)-[3-(3,3-diphenyl-propionylamino)-6-fluoro-1,2,3,4-tetrahydro-9H-carbazol-9-yl]-acetic acid;
(3R)-{3-[2-(3-chloro-phenoxy)-acetylamino]-6-fluoro-1,2,3,4-tetrahydro-9H-carbazol-9-yl}-acetic acid;
(3S)-[6-fluoro-3-(3-phenyl-propionylamino)-1,2,3,4-tetrahydro-9H-carbazol-9-yl]-acetic acid;
(3R)-{3-[2-(4-chloro-phenoxy)-acetylamino]-6-fluoro-1,2,3,4-tetrahydro-9H-carbazol-9-yl}-acetic acid;
(3S)-{3-[3-(2-chloro-phenyl)-propionylamino]-6-fluoro-1,2,3,4-tetrahydro-9H-carbazol-9-yl}-acetic acid;
(3R)-(3-isobutoxycarbonylamino-1,2,3,4-tetrahydro-9H-carbazol-9-yl)-acetic acid;
(3R)-[6-fluoro-3-(3-phenyl-propionylamino)-1,2,3,4-tetrahydro-9H-carbazol-9-yl]-acetic acid;
(3S)-{3-[3-(4-chloro-phenyl)-propionylamino]-6-fluoro-1,2,3,4-tetrahydro-9H-carbazol-9-yl}-acetic acid;
(3R)-(3-benzyloxycarbonylamino-6-fluoro-1,2,3,4-tetrahydro-9H-carbazol-9-yl)-acetic acid;
(3S)-(3-benzyloxycarbonylamino-6-fluoro-1,2,3,4-tetrahydro-9H-carbazol-9-yl)-acetic acid; and
(3S)-{3-[2-(4-chloro-phenoxy)-acetylamino]-6-fluoro-1,2,3,4-tetrahydro-9H-carbazol-9-yl}-acetic acid.

In another embodiment preferred compounds of Formula I are selected from the group consisting of:
(3R)-{3-[2-(2-chloro-phenoxy)-acetylamino]-6-fluoro-1,2,3,4-tetrahydro-9H-carbazol-9-yl}-acetic acid;
(3S)-{3-[3-(3-chloro-phenyl)-propionylamino]-6-fluoro-1,2,3,4-tetrahydro-9H-carbazol-9-yl}-acetic acid;
(3S)-[6-fluoro-3-(4-oxo-4-phenyl-butyrylamino)-1,2,3,4-tetrahydro-9H-carbazol-9-yl]-acetic acid;
(3S)-[6-fluoro-3-(2-indan-2-yl-acetylamino)-1,2,3,4-tetrahydro-9H-carbazol-9-yl]-acetic acid;
(3S)-{3-[(2,3-dihydro-1H-indole-2-carbonyl)-amino]-6-fluoro-1,2,3,4-tetrahydro-9H-carbazol-9-yl}-acetic acid;
(3S)-(3-{[2-(4-chloro-phenyl)-acetyl]-ethyl-amino}-6-fluoro-1,2,3,4-tetrahydro-9H-carbazol-9-yl)-acetic acid;
(3R)-(3-propoxycarbonylamino-1,2,3,4-tetrahydro-9H-carbazol-9-yl)-acetic acid;
(3R)-[6-fluoro-3-(2-p-tolyloxy-acetylamino)-1,2,3,4-tetrahydro-9H-carbazol-9-yl]-acetic acid;
(3S)-{6-fluoro-3-[methyl-(3-phenyl-propionyl)-amino]-1,2,3,4-tetrahydro-9H-carbazol-9-yl}-acetic acid;
(3S)-[6-fluoro-3-(3-1H-indol-3-yl-propionylamino)-1,2,3,4-tetrahydro-9H-carbazol-9-yl]-acetic acid;
(3S)-[3-(3-benzo[1,3]dioxol-5-yl-propionylamino)-6-fluoro-1,2,3,4-tetrahydro-9H-carbazol-9-yl]-acetic acid;
(3S)-{6-fluoro-3-[ethyl-(3-phenyl-propionyl)-amino]-1,2,3,4-tetrahydro-9H-carbazol-9-yl}-acetic acid;
(3S)-{3-[2-(4-chloro-phenyl)-acetylamino]-6-fluoro-1,2,3,4-tetrahydro-9H-carbazol-9-yl}-acetic acid;
(3S)-[3-(2,3-diphenyl-propionylamino)-6-fluoro-1,2,3,4-tetrahydro-9H-carbazol-9-yl]-acetic acid;
(3R)-[6-fluoro-3-(2-phenoxy-acetylamino)-1,2,3,4-tetrahydro-9H-carbazol-9-yl]-acetic acid;
(3S)-{3-[3-(3,4-difluoro-phenyl)-propionylamino]-6-fluoro-1,2,3,4-tetrahydro-9H-carbazol-9-yl}-acetic acid;
(3S)-[3-(3-phenyl-propionylamino)-1,2,3,4-tetrahydro-9H-carbazol-9-yl]-acetic acid;
(3R)-[3-(2-benzyloxy-acetylamino)-1,2,3,4-tetrahydro-9H-carbazol-9-yl]-acetic acid;
(3S)-{6-fluoro-3-[3-(2-methoxy-phenyl)-propionylamino]-1,2,3,4-tetrahydro-9H-carbazol-9-yl}-acetic acid;
(3S)-{6-fluoro-3-[propyl-(3-phenyl-propionyl)-amino]-1,2,3,4-tetrahydro-9H-carbazol-9-yl}-acetic acid;
(3S)-[3-(2-benzyloxy-acetylamino)-1,2,3,4-tetrahydro-9H-carbazol-9-yl]-acetic acid;
(3R)-(3-benzyloxycarbonylamino-1,2,3,4-tetrahydro-9H-carbazol-9-yl)-acetic acid;

(3R)-{6-fluoro-3-[2-(4-methoxy-phenyl)-acetylamino]-1,2,3,4-tetrahydro-9H-carbazol-9-yl}-acetic acid;
(3R)-{3-[3-(4-chloro-phenyl)-propionylamino]-6-fluoro-1,2,3,4-tetrahydro-9H-carbazol-9-yl}-acetic acid;
(3S)-{3-[4-(4-bromo-phenyl)-4-oxo-butyrylamino]-6-fluoro-1,2,3,4-tetrahydro-9H-carbazol-9-yl}-acetic acid;
(3S)-(3-{[2-(4-chloro-phenyl)-acetyl]-propyl-amino}-6-fluoro-1,2,3,4-tetrahydro-9H-carbazol-9-yl)-acetic acid;
(3R)-(3-phenylacetylamino-1,2,3,4-tetrahydro-9H-carbazol-9-yl)-acetic acid;
(3R)-{3-[3-(2-chloro-phenyl)-propionylamino]-6-fluoro-1,2,3,4-tetrahydro-9H-carbazol-9-yl}-acetic acid;
(3S)-{6-fluoro-3-[2-(4-trifluoromethyl-phenoxy)-acetylamino]-1,2,3,4-tetrahydro-9H-carbazol-9-yl}-acetic acid;
(3R)-(6-fluoro-3-phenylacetylamino-1,2,3,4-tetrahydro-9H-carbazol-9-yl)-acetic acid;
(3S)-{6-fluoro-3-[3-(2-hydroxy-phenyl)-propionylamino]-1,2,3,4-tetrahydro-9H-carbazol-9-yl}-acetic acid;
(3S)-[3-(3-1H-benzoimidazol-2-yl-propionylamino)-6-fluoro-1,2,3,4-tetrahydro-9H-carbazol-9-yl]-acetic acid;
(3S)-{6-fluoro-3-[3-(4-hydroxy-phenyl)-propionylamino]-1,2,3,4-tetrahydro-9H-carbazol-9-yl}-acetic acid;
(3S)-[6-fluoro-3-(2-p-tolyloxy-acetylamino)-1,2,3,4-tetrahydro-9H-carbazol-9-yl]-acetic acid;
(3R)-[6-fluoro-3-(2-p-tolyl-acetylamino)-1,2,3,4-tetrahydro-9H-carbazol-9-yl]-acetic acid;
(3R)-{3-[3-(3-chloro-phenyl)-propionylamino]-6-fluoro-1,2,3,4-tetrahydro-9H-carbazol-9-yl}-acetic acid;
(3R)-[3-(2-phenoxy-acetylamino)-1,2,3,4-tetrahydro-9H-carbazol-9-yl]-acetic acid;
(3S)-[6-fluoro-3-(3-p-tolyl-propionylamino)-1,2,3,4-tetrahydro-9H-carbazol-9-yl]-acetic acid;
(3S)-(3-benzyloxycarbonylamino-1,2,3,4-tetrahydro-9H-carbazol-9-yl)-acetic acid;
(3S)-[6-fluoro-3-(2-p-tolyl-acetylamino)-1,2,3,4-tetrahydro-9H-carbazol-9-yl]-acetic acid;
(3S)-[3-(3-phenethyl-ureido)-1,2,3,4-tetrahydro-9H-carbazol-9-yl]-acetic acid;
(3S)-{6-fluoro-3-[3-(3-hydroxy-phenyl)-propionylamino]-1,2,3,4-tetrahydro-9H-carbazol-9-yl}-acetic acid;
(3R)-[3-(2-benzyloxy-ethoxycarbonylamino)-1,2,3,4-tetrahydro-9H-carbazol-9-yl]-acetic acid;
(3S)-[6-fluoro-3-(3-naphthalen-2-yl-propionylamino)-1,2,3,4-tetrahydro-9H-carbazol-9-yl]-acetic acid;
(3S)-{6-fluoro-3-[4-(4-methanesulfonyl-phenyl)-4-oxo-butyrylamino]-1,2,3,4-tetrahydro-9H-carbazol-9-yl}-acetic acid;
(3S)-(3-{[2-(4-chloro-phenyl)-acetyl]-methyl-amino}-6-fluoro-1,2,3,4-tetrahydro-9H-carbazol-9-yl)-acetic acid;
(3S)-[3-(3-phenylsulfonyl-ureido)-1,2,3,4-tetrahydro-9H-carbazol-9-yl]-acetic acid;
(3S)-{6-fluoro-3-[3-(4-methoxy-phenyl)-propionylamino]-1,2,3,4-tetrahydro-9H-carbazol-9-yl}-acetic acid;
(3R)-[3-(3-phenyl-propionylamino)-1,2,3,4-tetrahydro-9H-carbazol-9-yl]-acetic acid;
(3R)-{3-[2-(4-chloro-phenyl)-acetylamino]-6-fluoro-1,2,3,4-tetrahydro-9H-carbazol-9-yl}-acetic acid;
(3R)-[6-fluoro-3-(3-p-tolyl-propionylamino)-1,2,3,4-tetrahydro-9H-carbazol-9-yl]-acetic acid;
(3R)-{6-fluoro-3-[3-(4-methoxy-phenyl)-propionylamino]-1,2,3,4-tetrahydro-9H-carbazol-9-yl}-acetic acid;
(3S)-{6-fluoro-3-[3-(4-hydroxy-3-methoxy-phenyl)-propionylamino]-1,2,3,4-tetrahydro-9H-carbazol-9-yl}-acetic acid;
(3S)-{6-fluoro-3-[2-(3-trifluoromethyl-phenyl)-acetylamino]-1,2,3,4-tetrahydro-9H-carbazol-9-yl}-acetic acid;
(3S)-{6-fluoro-3-[2-(4-methoxy-phenyl)-acetylamino]-1,2,3,4-tetrahydro-9H-carbazol-9-yl}-acetic acid;
(3R)-{3-[2-(3-chloro-phenyl)-acetylamino]-6-fluoro-1,2,3,4-tetrahydro-9H-carbazol-9-yl}-acetic acid;
(3S)-{6-fluoro-3-[2-(4-trifluoromethyl-phenyl)-acetylamino]-1,2,3,4-tetrahydro-9H-carbazol-9-yl}-acetic acid;
(3R)-(3-tert-butoxycarbonylamino-1,2,3,4-tetrahydro-9H-carbazol-9-yl)-acetic acid;
(3R)-{3-[2-(3,4-dichloro-phenyl)-acetylamino]-6-fluoro-1,2,3,4-tetrahydro-9H-carbazol-9-yl}-acetic acid;
(3S)-(3-isobutoxycarbonylamino-1,2,3,4-tetrahydro-9H-carbazol-9-yl)-acetic acid;
(3S)-{6-fluoro-3-[3-(3-methoxy-phenyl)-propionylamino]-1,2,3,4-tetrahydro-9H-carbazol-9-yl}-acetic acid; and
(3S)-[6-fluoro-3-(2-phenoxy-acetylamino)-1,2,3,4-tetrahydro-9H-carbazol-9-yl]-acetic acid.

In another embodiment preferred compounds of Formula I are selected from the group consisting of:
(3R)-[3-(3-phenethyl-ureido)-1,2,3,4-tetrahydro-9H-carbazol-9-yl]-acetic acid;
(3S)-[3-(2-benzyloxy-ethoxycarbonylamino)-1,2,3,4-tetrahydro-9H-carbazol-9-yl]-acetic acid;
(3S)-[3-(2-phenoxy-acetylamino)-1,2,3,4-tetrahydro-9H-carbazol-9-yl]-acetic acid;
(3S)-(3-propoxycarbonylamino-1,2,3,4-tetrahydro-9H-carbazol-9-yl)-acetic acid;
(3S)-[3-(2-thiophen-2-yl-acetylamino)-1,2,3,4-tetrahydro-9H-carbazol-9-yl]-acetic acid;
(3S)-(3-phenylacetylamino-1,2,3,4-tetrahydro-9H-carbazol-9-yl)-acetic acid;
(3R)-[3-(3-phenylsulfonyl-ureido)-1,2,3,4-tetrahydro-9H-carbazol-9-yl]-acetic acid;
(3S)-[3-(3-benzyl-ureido)-1,2,3,4-tetrahydro-9H-carbazol-9-yl]-acetic acid;
(3R)-[3-(3-naphthalen-1-yl-ureido)-1,2,3,4-tetrahydro-9H-carbazol-9-yl]-acetic acid;
(3S)-(3-decanoylamino-1,2,3,4-tetrahydro-9H-carbazol-9-yl)-acetic acid;
(3S)-[6-fluoro-3-(3-naphthalen-2-yl-acryloylamino)-1,2,3,4-tetrahydro-9H-carbazol-9-yl]-acetic acid;
(3S)-{3-[2-(4-tert-butyl-phenyl)-acetylamino]-6-fluoro-1,2,3,4-tetrahydro-9H-carbazol-9-yl}-acetic acid;
(3R)-(3-benzyloxycarbonylamino-8-chloro-6-fluoro-1,2,3,4-tetrahydro-9H-carbazol-9-yl)-acetic acid;
(3S)-(3-benzyloxycarbonylamino-8-chloro-6-fluoro-1,2,3,4-tetrahydro-9H-carbazol-9-yl)-acetic acid;
(3S)-[6-fluoro-3-(3-pyridin-3-yl-propionylamino)-1,2,3,4-tetrahydro-9H-carbazol-9-yl]-acetic acid;
(3R)-[3-(3-benzyl-ureido)-1,2,3,4-tetrahydro-9H-carbazol-9-yl]-acetic acid;
(3S)-[3-(3-methyl-butyrylamino)-1,2,3,4-tetrahydro-9H-carbazol-9-yl]-acetic acid;
(3R)-{6-fluoro-3-[2-(4-trifluoromethyl-phenyl)-acetylamino]-1,2,3,4-tetrahydro-9H-carbazol-9-yl}-acetic acid;
(3S)-[3-(3-phenyl-ureido)-1,2,3,4-tetrahydro-9H-carbazol-9-yl]-acetic acid;
(3S)-[3-(3-cyclopentyl-propionylamino)-1,2,3,4-tetrahydro-9H-carbazol-9-yl]-acetic acid;
(3R)-[3-(2-thiophen-2-yl-acetylamino)-1,2,3,4-tetrahydro-9H-carbazol-9-yl]-acetic acid;
(3S)-(3-butyrylamino-1,2,3,4-tetrahydro-9H-carbazol-9-yl)-acetic acid;

(3R)-(3-benzyloxycarbonylamino-8-chloro-5-fluoro-1,2,3,4-tetrahydro-9H-carbazol-9-yl)-acetic acid;
(3S)-(3-benzyloxycarbonylamino-8-chloro-5-fluoro-1,2,3,4-tetrahydro-9H-carbazol-9-yl)-acetic acid;
(3S)-(3-heptanoylamino-1,2,3,4-tetrahydro-9H-carbazol-9-yl)-acetic acid;
(3R)-[3-(3-cyclopentyl-propionylamino)-1,2,3,4-tetrahydro-9H-carbazol-9-yl]-acetic acid;
(3R)-(3-decanoylamino-1,2,3,4-tetrahydro-9H-carbazol-9-yl)-acetic acid;
(3R)-(3-benzoylamino-1,2,3,4-tetrahydro-9H-carbazol-9-yl)-acetic acid;
(3R)-[3-(3-butyl-ureido)-1,2,3,4-tetrahydro-9H-carbazol-9-yl]-acetic acid;
(3S)-{6-fluoro-3-[(1H-indole-2-carbonyl)-amino]-1,2,3,4-tetrahydro-9H-carbazol-9-yl}-acetic acid;
(3R)-[3-(3-methyl-butyrylamino)-1,2,3,4-tetrahydro-9H-carbazol-9-yl]-acetic acid; and
(3S)-[3-(3-butyl-ureido)-1,2,3,4-tetrahydro-9H-carbazol-9-yl]-acetic acid.

In another embodiment preferred compounds of Formula I are selected from the group consisting of:
(3R)-[3-(3-Benzyl-ureido)-6-fluoro-1,2,3,4-tetrahydro-9H-carbazol-9-yl]-acetic acid;
(3S)-[3-(3-Benzyl-ureido)-6-fluoro-1,2,3,4-tetrahydro-9H-carbazol-9-yl]-acetic acid;
(3S)-[6-Fluoro-3-(3-phenethyl-ureido)-1,2,3,4-tetrahydro-9H-carbazol-9-yl]-acetic acid;
(3R)-[3-(3-Benzyl-ureido)-8-chloro-6-fluoro-1,2,3,4-tetrahydro-9H-carbazol-9-yl]-acetic acid;
(3S)-[3-(3-Benzyl-ureido)-8-chloro-6-fluoro-1,2,3,4-tetrahydro-9H-carbazol-9-yl]-acetic acid;
(3R)-[8-Chloro-6-fluoro-3-(3-phenethyl-ureido)-1,2,3,4-tetrahydro-9H-carbazol-9-yl]-acetic acid;
(3S)-[8-Chloro-6-fluoro-3-(3-phenethyl-ureido)-1,2,3,4-tetrahydro-9H-carbazol-9-yl]-acetic acid;
(3R)-(3-Benzyloxycarbonylamino-6-trifluoromethyl-1,2,3,4-tetrahydro-9H-carbazol-9-yl)-acetic acid;
(3S)-(3-Benzyloxycarbonylamino-6-trifluoromethyl-1,2,3,4-tetrahydro-9H-carbazol-9-yl)-acetic acid;
(3R)-(3-Benzyloxycarbonylamino-8-bromo-6-fluoro-1,2,3,4-tetrahydro-9H-carbazol-9-yl)-acetic acid;
(3S)-(3-Benzyloxycarbonylamino-8-bromo-6-fluoro-1,2,3,4-tetrahydro-9H-carbazol-9-yl)-acetic acid;
(3R)-(3-Benzyloxycarbonylamino-6-fluoro-8-vinyl-1,2,3,4-tetrahydro-9H-carbazol-9-yl)-acetic acid;
(3S)-(3-Benzyloxycarbonylamino-6-fluoro-8-vinyl-1,2,3,4-tetrahydro-9H-carbazol-9-yl)-acetic acid;
(3R)-(3-Benzyloxycarbonylamino-6-fluoro-8-methanesulfonyl-1,2,3,4-tetrahydro-9H-carbazol-9-yl)-acetic acid;
(3S)-(3-Benzyloxycarbonylamino-6-fluoro-8-methanesulfonyl-1,2,3,4-tetrahydro-9H-carbazol-9-yl)-acetic acid;
(3S)-(3-Benzyloxycarbonylamino-6-fluoro-8-methyl-1,2,3,4-tetrahydro-9H-carbazol-9-yl)-acetic acid;
(3S)-(3-Benzyloxycarbonylamino-7-chloro-6-fluoro-1,2,3,4-tetrahydro-9H-carbazol-9-yl)-acetic acid;
(3S)-(8-Allyl-3-benzyloxycarbonylamino-6-fluoro-1,2,3,4-tetrahydro-9H-carbazol-9-yl)-acetic acid;
(3R)-(3-Benzyloxycarbonylamino-8-chloro-1,2,3,4-tetrahydro-9H-carbazol-9-yl)-acetic acid;
(3S)-{3-[3-(2,4-Dimethoxy-phenyl)-propionylamino]-6-fluoro-1,2,3,4-tetrahydro-9H-carbazol-9-yl}-acetic acid;
(3S)-[6-Fluoro-3-(3-naphthalen-1-yl-propionylamino)-1,2,3,4-tetrahydro-9H-carbazol-9-yl]-acetic acid;
(3R)-{6-Fluoro-3-[2-(2-methoxy-phenoxy)-acetylamino]-1,2,3,4-tetrahydro-9H-carbazol-9-yl}-acetic acid;
(3S)-{6-Fluoro-3-[2-(2-methoxy-phenoxy)-acetylamino]-1,2,3,4-tetrahydro-9H-carbazol-9-yl}-acetic acid;
(3R)-{6-Fluoro-3-[3-(2-methylphenyl)-propionylamino]-1,2,3,4-tetrahydro-9H-carbazol-9-yl}-acetic acid;
(3S)-{6-Fluoro-3-[3-(2-methylphenyl)-propionylamino]-1,2,3,4-tetrahydro-9H-carbazol-9-yl}-acetic acid;
(3R)-{6-Fluoro-3-[3-(3-methylphenyl)-propionylamino]-1,2,3,4-tetrahydro-9H-carbazol-9-yl}-acetic acid;
(3S)-{6-Fluoro-3-[3-(3-methylphenyl)-propionylamino]-1,2,3,4-tetrahydro-9H-carbazol-9-yl}-acetic acid;
(3R)-{6-Fluoro-3-[3-(3-methoxy-phenyl)-propionylamino]-1,2,3,4-tetrahydro-9H-carbazol-9-yl}-acetic acid;
(3S)-{6-Fluoro-3-[3-(3-methoxy-phenyl)-propionylamino]-1,2,3,4-tetrahydro-9H-carbazol-9-yl}-acetic acid;
(3R)-{6-Fluoro-3-[2-(3-methoxy-phenoxy)-acetylamino]-1,2,3,4-tetrahydro-9H-carbazol-9-yl}-acetic acid;
(3S)-{6-Fluoro-3-[2-(3-methoxy-phenoxy)-acetylamino]-1,2,3,4-tetrahydro-9H-carbazol-9-yl}-acetic acid;
(3R)-{6-Fluoro-3-[2-(2-methylphenoxy)-acetylamino]-1,2,3,4-tetrahydro-9H-carbazol-9-yl}-acetic acid;
(3S)-{6-Fluoro-3-[2-(2-methylphenoxy)-acetylamino]-1,2,3,4-tetrahydro-9H-carbazol-9-yl}-acetic acid;
(3S)-{3-[3-(2,5-Dimethoxy-phenyl)-propionylamino]-6-fluoro-1,2,3,4-tetrahydro-9H-carbazol-9-yl}-acetic acid;
(3S)-{6-Fluoro-3-[3-(4-trifluoromethyl-phenyl)-propionylamino]-1,2,3,4-tetrahydro-9H-carbazol-9-yl}-acetic acid;
(3S)-{3-[3-(2,6-Dichloro-phenyl)-propionylamino]-6-fluoro-1,2,3,4-tetrahydro-9H-carbazol-9-yl}-acetic acid;
(3S)-{3-[3-(2,5-Bis-trifluoromethyl-phenyl)-propionylamino]-6-fluoro-1,2,3,4-tetrahydro-9H-carbazol-9-yl}-acetic acid;
(3S)-{6-Fluoro-3-[3-(4-methylsulfanyl-phenyl)-propionylamino]-1,2,3,4-tetrahydro-9H-carbazol-9-yl}-acetic acid;
(3S)-{6-Fluoro-3-[3-(4-iodo-phenyl)-propionylamino]-1,2,3,4-tetrahydro-9H-carbazol-9-yl}-acetic acid;
(3S)-{6-Fluoro-3-[3-(4-isopropyl-phenyl)-propionylamino]-1,2,3,4-tetrahydro-9H-carbazol-9-yl}-acetic acid;
(3S)-{6-Fluoro-3-[3-(3-trifluoromethyl-phenyl)-propionylamino]-1,2,3,4-tetrahydro-9H-carbazol-9-yl}-acetic acid;
(3S)-{3-[3-(2,4-Dichloro-phenyl)-propionylamino]-6-fluoro-1,2,3,4-tetrahydro-9H-carbazol-9-yl}-acetic acid;
(3S)-{6-Fluoro-3-[3-(4-fluoro-phenyl)-propionylamino]-1,2,3,4-tetrahydro-9H-carbazol-9-yl}-acetic acid;
(3S)-{3-[3-(3,5-Bis-trifluoromethyl-phenyl)-propionylamino]-6-fluoro-1,2,3,4-tetrahydro-9H-carbazol-9-yl}-acetic acid;
(3S)-{3-[3-(4-Ethyl-phenyl)-propionylamino]-6-fluoro-1,2,3,4-tetrahydro-9H-carbazol-9-yl}-acetic acid;
(3S)-{6-Fluoro-3-[3-(3-iodo-phenyl)-propionylamino]-1,2,3,4-tetrahydro-9H-carbazol-9-yl}-acetic acid;
(3S)-{6-Fluoro-3-[3-(4-methanesulfonyl-phenyl)-propionylamino]-1,2,3,4-tetrahydro-9H-carbazol-9-yl}-acetic acid;
(3S)-{3-[3-(2,3-Dimethoxy-phenyl)-propionylamino]-6-fluoro-1,2,3,4-tetrahydro-9H-carbazol-9-yl}-acetic acid;
(3S)-{3-[3-(2-Bromo-phenyl)-propionylamino]-6-fluoro-1,2,3,4-tetrahydro-9H-carbazol-9-yl}-acetic acid;
(3S)-{6-Fluoro-3-[3-(3-trifluoromethoxy-phenyl)-propionylamino]-1,2,3,4-tetrahydro-9H-carbazol-9-yl}-acetic acid;

(3S)-{3-[3-(2,4-Dimethyl-phenyl)-propionylamino]-6-fluoro-1,2,3,4-tetrahydro-9H-carbazol-9-yl}-acetic acid;
(3S)-{3-[3-(3-Bromo-phenyl)-propionylamino]-6-fluoro-1,2,3,4-tetrahydro-9H-carbazol-9-yl}-acetic acid;
(3S)-{3-[3-(3-tert-Butoxycarbonylamino-phenyl)-propionylamino]-6-fluoro-1,2,3,4-tetrahydro-9H-carbazol-9-yl}-acetic acid;
(3S)-{6-Fluoro-3-[(S)-3-(4-fluoro-phenyl)-2-phenyl-propionylamino]-1,2,3,4-tetrahydro-9H-carbazol-9-yl}-acetic acid;
(3S)-{6-Fluoro-3-[(S)-3-(4-methoxy-phenyl)-2-phenyl-propionylamino]-1,2,3,4-tetrahydro-9H-carbazol-9-yl}-acetic acid;
(3S)-{6-Fluoro-3-[3-(2-fluoro-phenyl)-propionylamino]-1,2,3,4-tetrahydro-9H-carbazol-9-yl}-acetic acid;
(3S)-(6-Fluoro-3-{[(2RS)-1,2,3,4-tetrahydro-naphthalene-2-carbonyl]-amino}-1,2,3,4-tetrahydro-9H-carbazol-9-yl)-acetic acid;
(3S)-(6-Fluoro-3-{[(2RS)-8-methoxy-1,2,3,4-tetrahydro-naphthalene-2-carbonyl]-amino}-1,2,3,4-tetrahydro-9H-carbazol-9-yl)-acetic acid;
(3S)-(6-Fluoro-3-{(2RS)-2-[(4-fluoro-phenylcarbamoyl)-methyl]-3-phenyl-propionylamino}-1,2,3,4-tetrahydro-9H-carbazol-9-yl)-acetic acid;
(3S)-{3-[(2RS)-2-Benzyl-3,3-dimethyl-butyrylamino]-6-fluoro-1,2,3,4-tetrahydro-9H-carbazol-9-yl}-acetic acid;
(3S)-(6-Fluoro-3-{[(2RS)-8-methoxy-1,2,3,4-tetrahydro-naphthalene-2-carbonyl]-amino}-1,2,3,4-tetrahydro-9H-carbazol-9-yl)-acetic acid;
(3S)-{6-Fluoro-3-[3-(3-fluoro-phenyl)-propionylamino]-1,2,3,4-tetrahydro-9H-carbazol-9-yl}-acetic acid;
(3S)-(6-Fluoro-3-{[(2RS)-8-methoxy-1,2,3,4-tetrahydro-naphthalene-2-carbonyl]-amino}-1,2,3,4-tetrahydro-9H-carbazol-9-yl)-acetic acid;
(3S)-{6-Fluoro-3-[(2R)-2-methyl-3-phenyl-propionylamino]-1,2,3,4-tetrahydro-9H-carbazol-9-yl}-acetic acid;
(3S)-[3-(2,2-Dimethyl-3-phenyl-propionylamino)-6-fluoro-1,2,3,4-tetrahydro-9H-carbazol-9-yl]-acetic acid;
(3S)-[6-Fluoro-3-(3-methyl-3-phenyl-butyrylamino)-1,2,3,4-tetrahydro-9H-carbazol-9-yl]-acetic acid;
(3S)-{6-Fluoro-3-[(3S)-3-phenyl-butyrylamino]-1,2,3,4-tetrahydro-9H-carbazol-9-yl}-acetic acid;
(3S)-[3-(2-Benzyloxy-acetylamino)-6-fluoro-1,2,3,4-tetrahydro-9H-carbazol-9-yl]-acetic acid;
(3S)-[6-Fluoro-3-(4-phenyl-butyrylamino)-1,2,3,4-tetrahydro-9H-carbazol-9-yl]-acetic acid;
(3S)-{3-[(2R,3R)-2,3-Dihydroxy-3-(2-methoxy-phenylcarbamoyl)-propionylamino]-6-fluoro-1,2,3,4-tetrahydro-9H-carbazol-9-yl}-acetic acid;
(3R)-{8-Chloro-6-fluoro-3-[3-(2-methylphenyl)-propionylamino]-1,2,3,4-tetrahydro-9H-carbazol-9-yl}-acetic acid;
(3S)-{8-Chloro-6-fluoro-3-[3-(2-methylphenyl)-propionylamino]-1,2,3,4-tetrahydro-9H-carbazol-9-yl}-acetic acid;
(3R)-{8-Chloro-6-fluoro-3-[2-(2-methoxy-phenoxy)-acetylamino]-1,2,3,4-tetrahydro-9H-carbazol-9-yl}-acetic acid;
(3S)-{8-Chloro-6-fluoro-3-[2-(2-methoxy-phenoxy)-acetylamino]-1,2,3,4-tetrahydro-9H-carbazol-9-yl}-acetic acid;
(3R)-{8-Chloro-6-fluoro-3-[3-(3-hydroxy-phenyl)-propionylamino]-1,2,3,4-tetrahydro-9H-carbazol-9-yl}-acetic acid;
(3S)-{8-Chloro-6-fluoro-3-[3-(3-hydroxy-phenyl)-propionylamino]-1,2,3,4-tetrahydro-9H-carbazol-9-yl}-acetic acid;
(3R)-{8-Chloro-6-fluoro-3-[3-(3-methoxy-phenyl)-propionylamino]-1,2,3,4-tetrahydro-9H-carbazol-9-yl}-acetic acid;
(3S)-{8-Chloro-6-fluoro-3-[3-(3-methoxy-phenyl)-propionylamino]-1,2,3,4-tetrahydro-9H-carbazol-9-yl}-acetic acid;
(3R)-{8-Chloro-6-fluoro-3-[3-(3-methylphenyl)-propionylamino]-1,2,3,4-tetrahydro-9H-carbazol-9-yl}-acetic acid;
(3S)-{8-Chloro-6-fluoro-3-[3-(3-methylphenyl)-propionylamino]-1,2,3,4-tetrahydro-9H-carbazol-9-yl}-acetic acid;
(3R)-{8-Chloro-6-fluoro-3-[3-(2-hydroxy-phenyl)-propionylamino]-1,2,3,4-tetrahydro-9H-carbazol-9-yl}-acetic acid;
(3S)-{8-Chloro-6-fluoro-3-[3-(2-hydroxy-phenyl)-propionylamino]-1,2,3,4-tetrahydro-9H-carbazol-9-yl}-acetic acid;
(3R)-[8-Chloro-6-fluoro-3-(3-phenyl-propionylamino)-1,2,3,4-tetrahydro-9H-carbazol-9-yl]-acetic acid;
(3S)-[8-Chloro-6-fluoro-3-(3-phenyl-propionylamino)-1,2,3,4-tetrahydro-9H-carbazol-9-yl]-acetic acid;
(3R)-{8-Chloro-6-fluoro-3-[3-(2-methoxy-phenyl)-propionylamino]-1,2,3,4-tetrahydro-9H-carbazol-9-yl}-acetic acid;
(3S)-{8-Chloro-6-fluoro-3-[3-(2-methoxy-phenyl)-propionylamino]-1,2,3,4-tetrahydro-9H-carbazol-9-yl}-acetic acid;
(3R)-{8-Chloro-3-[3-(3-chloro-phenyl)-propionylamino]-6-fluoro-1,2,3,4-tetrahydro-9H-carbazol-9-yl}-acetic acid;
(3S)-{8-Chloro-3-[3-(3-chloro-phenyl)-propionylamino]-6-fluoro-1,2,3,4-tetrahydro-9H-carbazol-9-yl}-acetic acid;
(3R)-[8-Chloro-6-fluoro-3-(3-1H-indol-3-yl-propionylamino)-1,2,3,4-tetrahydro-9H-carbazol-9-yl]-acetic acid;
(3S)-[8-Chloro-6-fluoro-3-(3-1H-indol-3-yl-propionylamino)-1,2,3,4-tetrahydro-9H-carbazol-9-yl]-acetic acid;
(3R)-{8-Chloro-3-[2-(2-chloro-phenoxy)-acetylamino]-6-fluoro-1,2,3,4-tetrahydro-9H-carbazol-9-yl}-acetic acid;
(3S)-{8-Chloro-3-[2-(2-chloro-phenoxy)-acetylamino]-6-fluoro-1,2,3,4-tetrahydro-9H-carbazol-9-yl}-acetic acid;
(3R)-{8-Chloro-6-fluoro-3-[2-(2-methylphenyl)-oxy-acetylamino]-1,2,3,4-tetrahydro-9H-carbazol-9-yl}-acetic acid;
(3S)-{8-Chloro-6-fluoro-3-[2-(2-methylphenyl)-oxy-acetylamino]-1,2,3,4-tetrahydro-9H-carbazol-9-yl}-acetic acid;
(3R)-[3-(3-Benzo[1,3]dioxol-5-yl-propionylamino)-8-chloro-6-fluoro-1,2,3,4-tetrahydro-9H-carbazol-9-yl]-acetic acid;
(3S)-[3-(3-Benzo[1,3]dioxol-5-yl-propionylamino)-8-chloro-6-fluoro-1,2,3,4-tetrahydro-9H-carbazol-9-yl]-acetic acid;
(3R)-{8-Chloro-6-fluoro-3-[2-(3-methoxy-phenoxy)-acetylamino]-1,2,3,4-tetrahydro-9H-carbazol-9-yl}-acetic acid;
(3S)-{8-Chloro-6-fluoro-3-[2-(3-methoxy-phenoxy)-acetylamino]-1,2,3,4-tetrahydro-9H-carbazol-9-yl}-acetic acid;
(3R)-{8-Chloro-3-[2-(3-chloro-phenoxy)-acetylamino]-6-fluoro-1,2,3,4-tetrahydro-9H-carbazol-9-yl}-acetic acid;
(3S)-{8-Chloro-3-[2-(3-chloro-phenoxy)-acetylamino]-6-fluoro-1,2,3,4-tetrahydro-9H-carbazol-9-yl}-acetic acid;
(3R)-{8-Chloro-3-[3-(2-chloro-phenyl)-propionylamino]-6-fluoro-1,2,3,4-tetrahydro-9H-carbazol-9-yl}-acetic acid;

(3S)-{8-Chloro-3-[3-(2-chloro-phenyl)-propionylamino]-6-fluoro-1,2,3,4-tetrahydro-9H-carbazol-9-yl}-acetic acid;
(3R)-[8-Chloro-6-fluoro-3-(2-indan-2-yl-acetylamino)-1,2,3,4-tetrahydro-9H-carbazol-9-yl]-acetic acid;
(3S)-[8-Chloro-6-fluoro-3-(2-indan-2-yl-acetylamino)-1,2,3,4-tetrahydro-9H-carbazol-9-yl]-acetic acid;
(3S)-[6-Fluoro-3-(1-methyl-3-phenethyl-ureido)-1,2,3,4-tetrahydro-9H-carbazol-9-yl]-acetic acid;
(3S)-{3-[3-(2-Chloro-benzyl)-1-methyl-ureido]-6-fluoro-1,2,3,4-tetrahydro-9H-carbazol-9-yl}-acetic acid;
(3S)-[3-(3-Benzyl-1-methyl-ureido)-6-fluoro-1,2,3,4-tetrahydro-9H-carbazol-9-yl]-acetic acid;
(3S)-[3-(Benzyloxycarbonyl-methyl-amino)-6-fluoro-1,2,3,4-tetrahydro-9H-carbazol-9-yl]-acetic acid;
{(3S)-3-[(2-Chloro-benzyloxycarbonyl)-methyl-amino]-6-fluoro-1,2,3,4-tetrahydro-9H-carbazol-9-yl}-acetic acid;
(3S)-(6-Fluoro-3-{[2-(4-methoxy-phenyl)-acetyl]-methyl-amino}-1,2,3,4-tetrahydro-9H-carbazol-9-yl)-acetic acid;
(3S)-(6-Fluoro-3-{methyl-[2-(4-methylphenyl)-acetyl]-amino}-1,2,3,4-tetrahydro-9H-carbazol-9-yl)-acetic acid;
(3S)-(6-Fluoro-3-{[2-(2-methoxy-phenyl)-acetyl]-methyl-amino}-1,2,3,4-tetrahydro-9H-carbazol-9-yl)-acetic acid;
(3S)-{6-Fluoro-3-[(2-indan-2-yl-acetyl)-methyl-amino]-1,2,3,4-tetrahydro-9H-carbazol-9-yl}-acetic acid;
(3S)-(3-{[2-(3-Chloro-phenyl)-acetyl]-methyl-amino}-6-fluoro-1,2,3,4-tetrahydro-9H-carbazol-9-yl)-acetic acid;
(3S)-(6-Fluoro-3-{methyl-[2-(3-methylphenyl)-acetyl]-amino}-1,2,3,4-tetrahydro-9H-carbazol-9-yl)-acetic acid;
(3S)-(6-Fluoro-3-{[2-(3-methoxy-phenyl)-acetyl]-methyl-amino}-1,2,3,4-tetrahydro-9H-carbazol-9-yl)-acetic acid;
(3S)-(3-{[2-(2-Chloro-phenoxy)-acetyl]-methyl-amino}-6-fluoro-1,2,3,4-tetrahydro-9H-carbazol-9-yl)-acetic acid;
(3S)-(3-{[2-(4-Chloro-phenoxy)-acetyl]-methyl-amino}-6-fluoro-1,2,3,4-tetrahydro-9H-carbazol-9-yl)-acetic acid;
(3S)-(6-Fluoro-3-{[3-(3-methoxy-phenyl)-propionyl]-methyl-amino}-1,2,3,4-tetrahydro-9H-carbazol-9-yl)-acetic acid;
(3S)-(6-Fluoro-3-{methyl-[2-(2-methylphenyl)-acetyl]-amino}-1,2,3,4-tetrahydro-9H-carbazol-9-yl)-acetic acid;
(3S)-{3-[(3,3-Diphenyl-propionyl)-methyl-amino]-6-fluoro-1,2,3,4-tetrahydro-9H-carbazol-9-yl}-acetic acid;
(3S)-(6-Fluoro-3-{[3-(2-methoxy-phenyl)-propionyl]-methyl-amino}-1,2,3,4-tetrahydro-9H-carbazol-9-yl)-acetic acid;
(3S)-{6-Fluoro-3-[(3-1H-indol-3-yl-propionyl)-methyl-amino]-1,2,3,4-tetrahydro-9H-carbazol-9-yl}-acetic acid;
(3S)-{3-[(2-Benzyloxy-acetyl)-methyl-amino]-6-fluoro-1,2,3,4-tetrahydro-9H-carbazol-9-yl}-acetic acid;
(3S)-{3-[(2,3-Diphenyl-propionyl)-methyl-amino]-6-fluoro-1,2,3,4-tetrahydro-9H-carbazol-9-yl}-acetic acid;
(3S)-{6-Fluoro-3-[[3-(2-methoxy-phenyl)-propionyl]-(3-phenyl-propyl)-amino]-1,2,3,4-tetrahydro-9H-carbazol-9-yl}-acetic acid;
(3S)-{3-[Acetyl-(3-phenyl-propyl)-amino]-6-fluoro-1,2,3,4-tetrahydro-9H-carbazol-9-yl}-acetic acid;
(3S)-{3-[3-Benzyl-(1-cyclopropylmethyl)-ureido]-6-fluoro-1,2,3,4-tetrahydro-9H-carbazol-9-yl}-acetic acid;
(3S)-[3-(Benzyloxycarbonyl-cyclopropylmethyl-amino)-6-fluoro-1,2,3,4-tetrahydro-9H-carbazol-9-yl]-acetic acid;
(3S)-{3-[Cyclopropylmethyl-(3-phenyl-propionyl)-amino]-6-fluoro-1,2,3,4-tetrahydro-9H-carbazol-9-yl}-acetic acid;
(3S)-{3-[Cyclopropylmethyl-((S)-2-methyl-3-phenyl-propionyl)-amino]-6-fluoro-1,2,3,4-tetrahydro-9H-carbazol-9-yl}-acetic acid;
(3S)-(3-{Cyclopropylmethyl-[3-(2-methoxy-phenyl)-propionyl]-amino}-6-fluoro-1,2,3,4-tetrahydro-9H-carbazol-9-yl)-acetic acid;
(3S)-(3-{[2-(3-Chloro-phenoxy)-acetyl]-cyclopropylmethyl-amino}-6-fluoro-1,2,3,4-tetrahydro-9H-carbazol-9-yl)-acetic acid;
(3S)-{3-[Cyclopropylmethyl-(3,3-diphenyl-propionyl)-amino]-6-fluoro-1,2,3,4-tetrahydro-9H-carbazol-9-yl}-acetic acid;
(3S)-{3-[Cyclopropylmethyl-(2-naphthalen-1-yl-acetyl)-amino]-6-fluoro-1,2,3,4-tetrahydro-9H-carbazol-9-yl}-acetic acid;
(3S)-(3-{Benzyloxycarbonyl-[2-(4-trifluoromethyl-phenoxy)-ethyl]-amino}-6-fluoro-1,2,3,4-tetrahydro-9H-carbazol-9-yl)-acetic acid;
(3S)-(3-{Acetyl-[2-(4-trifluoromethyl-phenoxy)-ethyl]-amino}-6-fluoro-1,2,3,4-tetrahydro-9H-carbazol-9-yl)-acetic acid;
(3S)-(6-Fluoro-3-{propionyl-[2-(4-trifluoromethyl-phenoxy)-ethyl]-amino}-1,2,3,4-tetrahydro-9H-carbazol-9-yl)-acetic acid;
(3S)-(6-Fluoro-3-{(3-phenyl-propionyl)-[2-(4-trifluoromethyl-phenoxy)-ethyl]-amino}-1,2,3,4-tetrahydro-9H-carbazol-9-yl)-acetic acid;
(3S)-(6-Fluoro-3-{[3-(2-methoxy-phenyl)-propionyl]-[2-(4-trifluoromethyl-phenoxy)-ethyl]-amino}-1,2,3,4-tetrahydro-9H-carbazol-9-yl)-acetic acid;
(3S)-{6-Fluoro-3-[(2-phenoxy-ethyl)-(3-phenyl-propionyl)-amino]-1,2,3,4-tetrahydro-9H-carbazol-9-yl}-acetic acid;
(3S)-{6-Fluoro-3-[((S)-2-methyl-3-phenyl-propionyl)-(2-phenoxy-ethyl)-amino]-1,2,3,4-tetrahydro-9H-carbazol-9-yl}-acetic acid;
(3S)-{6-Fluoro-3-[[3-(2-methoxy-phenyl)-propionyl]-(2-phenoxy-ethyl)-amino]-1,2,3,4-tetrahydro-9H-carbazol-9-yl}-acetic acid;
(3S)-{3-[Acetyl-(2-phenoxy-ethyl)-amino]-6-fluoro-1,2,3,4-tetrahydro-9H-carbazol-9-yl}-acetic acid;
(3S)-{3-[3-Benzyl-1-(2-methoxy-ethyl)-ureido]-6-fluoro-1,2,3,4-tetrahydro-9H-carbazol-9-yl}-acetic acid;
(3S)-{3-[Benzyloxycarbonyl-(2-methoxy-ethyl)-amino]-6-fluoro-1,2,3,4-tetrahydro-9H-carbazol-9-yl}-acetic acid;
(3S)-{6-Fluoro-3-[(2-methoxy-ethyl)-(3-phenyl-propionyl)-amino]-1,2,3,4-tetrahydro-9H-carbazol-9-yl}-acetic acid;
(3S)-{6-Fluoro-3-[(2-methoxy-ethyl)-((S)-2-methyl-3-phenyl-propionyl)-amino]-1,2,3,4-tetrahydro-9H-carbazol-9-yl}-acetic acid;
(3S)-(6-Fluoro-3-{(2-methoxy-ethyl)[3-(2-methoxy-phenyl)-propionyl]-amino}-1,2,3,4-tetrahydro-9H-carbazol-9-yl)-acetic acid;
(3S)-{3-[[2-(3-Chloro-phenoxy)-acetyl]-(2-methoxy-ethyl)-amino]-6-fluoro-1,2,3,4-tetrahydro-9H-carbazol-9-yl}-acetic acid;
(3S)-{3-[(3,3-Diphenyl-propionyl)-(2-methoxy-ethyl)-amino]-6-fluoro-1,2,3,4-tetrahydro-9H-carbazol-9-yl}-acetic acid;
(3S)-{6-Fluoro-3-[(2-methoxy-ethyl)-(2-naphthalen-1-yl-acetyl)-amino]-1,2,3,4-tetrahydro-9H-carbazol-9-yl}-acetic acid;
(3S)-(6-Fluoro-3-{[(2S)-2-methyl-3-phenyl-propionyl]-phenethyl-amino}-1,2,3,4-tetrahydro-9H-carbazol-9-yl)-acetic acid;
(3S)-(6-Fluoro-3-{[3-(2-methoxy-phenyl)-propionyl]-phenethyl-amino}-1,2,3,4-tetrahydro-9H-carbazol-9-yl)-acetic acid;
(3S)-[3-(Acetyl-phenethyl-amino)-6-fluoro-1,2,3,4-tetrahydro-9H-carbazol-9-yl]-acetic acid;

(3S)-{6-Fluoro-3-[(2-naphthalen-1-yl-acetyl)-phenethyl-amino]-1,2,3,4-tetrahydro-9H-carbazol-9-yl}-acetic acid;
(3S)-{6-Fluoro-3-[phenethyl-(3-phenyl-propionyl)-amino]-1,2,3,4-tetrahydro-9H-carbazol-9-yl}-acetic acid;
(3S)-[3-(3-Benzyl-1-naphthalen-1-ylmethyl-ureido)-6-fluoro-1,2,3,4-tetrahydro-9H-carbazol-9-yl]-acetic acid;
(3S)-[3-(Benzyloxycarbonyl-naphthalen-1-ylmethyl-amino)-6-fluoro-1,2,3,4-tetrahydro-9H-carbazol-9-yl]-acetic acid;
(3S)-{6-Fluoro-3-[naphthalen-1-ylmethyl-(3-phenyl-propionyl)-amino]-1,2,3,4-tetrahydro-9H-carbazol-9-yl}-acetic acid;
(3S)-{6-Fluoro-3-[((S)-2-methyl-3-phenyl-propionyl)-naphthalen-1-ylmethyl-amino]-1,2,3,4-tetrahydro-9H-carbazol-9-yl}-acetic acid;
(3S)-(6-Fluoro-3-{[3-(2-methoxy-phenyl)-propionyl]-naphthalen-1-ylmethyl-amino}-1,2,3,4-tetrahydro-9H-carbazol-9-yl)-acetic acid;
(3S)-{3-[(3,3-Diphenyl-propionyl)-naphthalen-1-ylmethyl-amino]-6-fluoro-1,2,3,4-tetrahydro-9H-carbazol-9-yl}-acetic acid;
(3S)-[3-(Acetyl-naphthalen-1-ylmethyl-amino)-6-fluoro-1,2,3,4-tetrahydro-9H-carbazol-9-yl]-acetic acid;
(3S)-[6-Fluoro-3-(naphthalen-1-ylmethyl-propionyl-amino)-1,2,3,4-tetrahydro-9H-carbazol-9-yl]-acetic acid;
(3S)-{3-[(RS)-2-Benzyl-3-(2-methylphenyl)-carbamoyl-propionylamino]-6-fluoro-1,2,3,4-tetrahydro-9H-carbazol-9-yl}-acetic acid;
(3S)-{3-[(RS)-2-Benzyl-3-(3-methoxy-phenylcarbamoyl)-propionylamino]-6-fluoro-1,2,3,4-tetrahydro-9H-carbazol-9-yl}-acetic acid;
(3S)-{3-[(RS)-2-Benzyl-3-(4-chloro-phenylcarbamoyl)-propionylamino]-6-fluoro-1,2,3,4-tetrahydro-9H-carbazol-9-yl}-acetic acid;
(3S)-{3-[(RS)-2-Benzyl-3-(4-fluoro-benzylcarbamoyl)-propionylamino]-6-fluoro-1,2,3,4-tetrahydro-9H-carbazol-9-yl}-acetic acid;
[(3S)-3((RS)-2-Benzyl-3-propylcarbamoyl-propionylamino)-6-fluoro-1,2,3,4-tetrahydro-9H-carbazol-9-yl]-acetic acid;
(3S)-[6-Fluoro-3-(3-thiophen-2-yl-propionylamino)-1,2,3,4-tetrahydro-9H-carbazol-9-yl]-acetic acid;
(3S)-{3-[3-(2-Chloro-isoxazol-5-yl)-propionylamino]-6-fluoro-1,2,3,4-tetrahydro-9H-carbazol-9-yl}-acetic acid;
(3S)-[6-Fluoro-3-(3-pyrimidin-2-yl-propionylamino)-1,2,3,4-tetrahydro-9H-carbazol-9-yl]-acetic acid;
(3S)-{6-Fluoro-3-[3-phenyl-4-([1,3,4]thiadiazol-2-ylcarbamoyl)-butyrylamino]-1,2,3,4-tetrahydro-9H-carbazol-9-yl}-acetic acid;
(3S)-[3-(1,3-Dibenzyl-ureido)-6-fluoro-1,2,3,4-tetrahydro-9H-carbazol-9-yl]-acetic acid;
(3S)-(3-{Acetyl-[2-(2-fluoro-phenyl)-ethyl]-amino}-6-fluoro-1,2,3,4-tetrahydro-9H-carbazol-9-yl)-acetic acid;
(3S)-(3-{Acetyl-[2-(3-fluoro-phenyl)-ethyl]-amino}-6-fluoro-1,2,3,4-tetrahydro-9H-carbazol-9-yl)-acetic acid;
(3S)-[3-(3-Benzyl-1-cyclohexylmethyl-ureido)-6-fluoro-1,2,3,4-tetrahydro-9H-carbazol-9-yl]-acetic acid; and
(3S)-(3-{Cyclohexylmethyl-[3-(2-methoxy-phenyl)-propionyl]-amino}-6-fluoro-1,2,3,4-tetrahydro-9H-carbazol-9-yl)-acetic acid.

Unless explicitly stated otherwise, the general terms and names used hereinbefore and hereinafter preferably have within the context of this disclosure the following meanings Where the plural form is used for compounds, salts, pharmaceutical compositions, diseases and the like, this is intended to mean also a single compound, salt, or the like.

Any reference to a compound of Formula I is to be understood as referring also to salts (especially pharmaceutically acceptable salts) of a compound of Formula I, as appropriate and expedient.

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

The term "bridging group" or "bridging atom" as used herein means a group or atom that is placed between two distinct moieties of the molecule.

Examples for such bridging groups are the bridging $C_{1-6}$-alkyl group in an aryl-$C_{1-6}$-alkylcarbonyl group which is placed between the aryl and the carbonyl moiety; the bridging $C_{1-4}$-alkyl group in an aryl-$C_{1-4}$-alkyl group, which is placed between the aryl moiety and the parent molecular moiety; or the bridging $C_{1-4}$-alkyl group in an $R^7$—$C_{1-4}$-alkylcarbonyl group which is placed between the $R^7$-group and the carbonyl moiety.

An example for such bridging atoms is the bridging carbon atom of a methylene (—$CH_2$—) group in a benzyloxy or benzylamino group, which is placed between the phenyl ring and the oxygen atom, or the phenyl ring and the nitrogen atom, respectively.

The term "alkyl" as used herein, alone or in any combination, refers to a saturated aliphatic group including a straight or branched hydrocarbon chain containing the indicated number of carbon atoms, for example $C_{1-9}$-alkyl, i.e. an alkyl having 1-9 carbon atoms. Representative examples of alkyl groups include, but are not limited to, methyl, ethyl, n-propyl, iso-propyl, n-butyl, tent-butyl, iso-butyl (or also referred to as "2-methylpropyl"), n-pentyl (also referred to as "n-amyl"), iso-pentyl (also referred to as "iso-amyl"), n-hexyl, n-heptyl, and n-octyl. Preferred are methyl, ethyl, n-propyl, iso-propyl, n-butyl, and iso-butyl. Most preferred are methyl, ethyl, n-propyl, and iso-propyl.

A bridging $C_{1-6}$-alkyl group as used in "aryl-$C_{1-6}$-alkylcarbonyl" as defined for $R^6$ preferably means a $C_{2-4}$-alkyl group, whereby the aryl moiety and the carbonyl moiety are preferably attached to two different carbon atoms of the bridging $C_{2-4}$-alkyl group. Preferred examples of bridging $C_{1-6}$-alkyl groups as used in $R^6$ being aryl-$C_{1-6}$-alkylcarbonyl are ethane-1,2-diyl, propane-1,2-diyl, propane-1,3-diyl, and 2-methyl-propane-1,2-diyl.

In another embodiment a bridging $C_{1-6}$-alkyl group as used in "aryl-$C_{1-6}$-alkylcarbonyl" as defined for $R^6$ means the respective $C_{1-6}$-alkyl group, whereby the aryl moiety and the carbonyl moiety preferably are attached to the same carbon atom of the bridging $C_{1-6}$-alkyl group. Examples of such bridging $C_{1-6}$-alkyl groups as used in $R^6$ being aryl-$C_{1-6}$-alkylcarbonyl are a methylene group (preferred) and ethane-1,1-diyl.

A bridging $C_{1-3}$-alkyl group as used in "diaryl-$C_{1-3}$-alkylcarbonyl" as defined for $R^6$ preferably means a $C_{2-3}$-alkyl group, whereby the carbonyl moiety and at least one of the aryl groups are preferably attached to two different carbon atoms of the bridging $C_{2-3}$-alkyl group. Preferred examples of such bridging $C_{1-3}$-alkyl groups as used in $R^6$ being diaryl-$C_{1-3}$-alkylcarbonyl are ethane-1,2,2-triyl, and ethane-1,1,2-triyl.

A bridging $C_{1-4}$-alkyl group as used in "$R^7$—$C_{1-4}$-alkylcarbonyl, wherein the bridging $C_{1-4}$-alkyl group may additionally be mono-substituted with aryl" as defined for $R^6$ preferably means a $C_{2-4}$-alkyl group (particularly, if the additional aryl substituent is present, it means propane-1,2,3-triyl) whereby the group $R^7$, the carbonyl moiety, and the aryl substituent (if present) preferably are attached to two (three, if the additional aryl substituent is present) different carbon atoms of the bridging $C_{2-4}$-alkyl group. Examples of bridging $C_{1-4}$-alkyl groups as used in $R^6$ being "$R^7$—$C_{1-4}$-alkylcarbonyl, wherein the bridging $C_{1-4}$-alkyl group may additionally be mono-substituted with aryl" are ethane-1,2-diyl, propane-1,2-diyl, propane-1,3-diyl, 2-phenyl-propane-1,3-diyl, and 1-phenyl-propane-2,3-diyl; preferred are 2-phenyl-propane-1,3-diyl, and 1-phenyl-propane-2,3-diyl, especially 1-phenyl-propane-2,3-diyl.

An example of a bridging $C_{1-4}$-alkyl group as used in $R^6$ being "$R^7$—$C_{1-4}$-alkylcarbonyl, wherein the bridging $C_{1-4}$-alkyl group may additionally be disubstituted with hydroxy" is 1,2-dihydroxyethane-1,2-diyl.

The term "alkenyl" as used herein, alone or in any combination, refers to a straight or branched hydrocarbon chain containing 2-7, preferably 2-4, carbon atoms with at least one carbon-carbon double bond ($R_aR_bC=CR_cR_d$). $R_a$—$R_d$ refer to substituents, each individually and independently selected from hydrogen and alkyl. Representative examples of alkenyl include, but are not limited to, ethenyl (also referred to as "vinyl"), 2-propenyl (also referred to as "allyl"), 2-methyl-2-propenyl, 3-butenyl, 4-pentenyl, and 5-hexenyl, especially ethenyl or 2-propenyl.

The term "$C_{1-2}$-alkylendioxy" as used herein, alone or in any combination, refers to an —O(CH$_2$)$_n$O— group, wherein n is 1 or 2, and wherein the oxygen atoms are attached to two adjacent carbon atoms of the parent molecular moiety, preferably the two adjacent carbon atoms of a phenyl ring.

The term "alkoxy" as used herein, alone or in any combination, refers to an alkyl group attached to the parent molecular moiety through an oxygen bridge. Representative examples of alkoxy include, but are not limited to, methoxy, ethoxy, propoxy, 2-propoxy, butoxy, tent-butoxy, pentoxy, and hexyloxy, especially methoxy.

The term "alkoxycarbonyl", as used herein, alone or in any combination, refers to an alkoxy group attached to the parent molecular moiety through a carbonyl group. Representative examples of alkoxycarbonyl include, but are not limited to, methoxycarbonyl, ethoxycarbonyl, n-propoxycarbonyl, and iso-butoxycarbonyl, especially methoxy. $R^6$ representing alkoxycarbonyl preferably means n-propoxycarbonyl, and iso-butoxycarbonyl.

The term "alkylcarbonyl" as used herein, alone or in any combination, refers to an alkyl group attached to the parent molecular moiety through a carbonyl group. Representative examples of alkylcarbonyl include, but are not limited to, acetyl, 1-oxopropyl, 2,2-dimethyl-1-oxopropyl, 1-oxobutyl, and 1-oxopentyl. Further examples are 1-oxo-2-methyl-butyl, and 3,3-dimethyl-1-oxopropyl. Preferred are acetyl, 1-oxopropyl, 1-oxobutyl, 1-oxo-2-methyl-butyl, and 3,3-dimethyl-1-oxopropyl.

The term "alkylsulfonyl", as used herein, alone or in any combination, refers to an alkyl group attached to the parent molecular moiety through a sulfonyl group. Representative examples of alkylsulfonyl include, but are not limited to, methanesulfonyl and ethanesulfonyl, preferably methanesulfonyl.

The term "aminocarbonyl" (also referred to as "carbamoyl") as used herein, alone or in any combination, refers to an amino group attached to the parent molecular moiety through a carbonyl group.

The term "aryl" or "aryl group", as used herein, alone or in any combination, refers to an aromatic carbocyclic group from 6 to 14 carbon atoms having a single ring or multiple condensed rings, and preferably refers to a phenyl or naphthyl, very preferably to a phenyl group. An aryl group is preferably unsubstituted. In another embodiment the aryl group may be substituted as specifically described in the embodiments of the present invention. If an aryl group is mono- or di-substituted, preferred but not limiting examples are 4-trifluoromethyl-phenyl, 3-trifluoromethyl-phenyl, 2,5-bis-trifluoromethyl-phenyl, 3,5-bis-trifluoromethyl-phenyl, 3-trifluoromethoxy-phenyl, 4-chlorophenyl, 3-chlorophenyl, 2-chlorophenyl, 2,6-dichlorophenyl, 2,4-dichlorophenyl, 4-methylphenyl, 3-methylphenyl, 2-methylphenyl, 2,4-dimethylphenyl, 4-ethylphenyl, 4-isopropylphenyl, 4-tert.-butylphenyl, 4-fluorophenyl, 3-fluorophenyl, 2-fluorophenyl, 3,4-difluorophenyl, 4-iodophenyl, 3-bromophenyl, 2-bromophenyl, 4-methoxyphenyl, 3-methoxyphenyl, 2-methoxyphenyl, 2,3-dimethoxyphenyl, 2,4-dimethoxyphenyl, 2,5-dimethoxyphenyl, 4-hydroxyphenyl, 3-hydroxyphenyl, 2-hydroxyphenyl, 4-methylthio-phenyl, 4-methanesulfonyl-phenyl, and 3-tert.-butoxycarbonylamino-phenyl.

The term "arylalkenyl", as used herein, alone or in any combination, refers to an aryl group attached to the parent molecular moiety through an alkenyl group. Representative examples of arylalkenyl include, but are not limited to, 2-phenylethenyl, 3-phenylpropen-2-yl, and 2-naphth-2-ylethenyl.

The term "aryloxy", as used herein, alone or in any combination, refers to an aryl group attached to the parent molecular moiety through an oxygen bridge.

The term "arylsulfonyl", as used herein, alone or in any combination, refers to an aryl group attached to the parent molecular moiety through a sulfonyl group.

The term "carbonyl", as used herein, alone or in any combination, refers to a —C(O)— group.

The term "thiocarbonyl", as used herein, alone or in any combination, refers to a —C(S)— group.

The term "carboxy", as used herein, alone or in any combination, refers to a —CO$_2$H group.

The term "cyano", as used herein, alone or in any combination, refers to a —C≡N group.

The term "cycloalkyl", as used herein, alone or in any combination, refers to a saturated cyclic hydrocarbon moiety containing 3-10 carbon atoms (for example $C_{3-6}$-cycloalkyl means a cycloalkyl having 3 to 6 carbon atoms), preferably a cyclopentyl or cyclohexyl radical, whereby said radicals, especially the cyclopentyl radical, may be substituted with an annellated benzene ring. In another embodiment said benzene ring may be mono-, or di-substituted, wherein the substituent(s) are independently selected from $C_{1-4}$-alkyl, $C_{1-4}$-alkoxy, and halogen (especially $C_{1-4}$-alkoxy). In case the cycloalkyl group is used as a bridging group as for example in an "aryl-$C_{3-6}$-cycloalkylcarbonyl" group as defined for $R^6$, it is preferably a cyclopropane-diyl, cyclopentane-diyl or cyclohexane-diyl radical (especially cyclopropane-1,2-diyl) said radical being preferably unsubstituted.

The term "formyl", as used herein, alone or in any combination, refers to a —C(O)H group.

The term "halo" or "halogen", as used herein, alone or in any combination, refers to fluorine, bromine, chlorine, or iodine, and unless specifically indicated otherwise, it refers to especially fluorine or chlorine.

The term "haloalkyl", as used herein, alone or in any combination, refers to an alkyl group having at least one hydrogen atom replaced with a halogen atom. Representative examples of haloalkyl include, but are not limited to, chloromethyl, 2-fluoroethyl, trifluoromethyl, pentafluoroethyl, and 2-chloro-3-fluoropentyl, preferably trifluoromethyl.

The term "haloalkoxy", as used herein, alone or in any combination, refers to an alkoxy group having at least one hydrogen atom replaced with a halogen atom. Representative examples of haloalkoxy include, but are not limited to, chloromethoxy, 2-fluoroethoxy, trifluoromethoxy, and pentafluoroethoxy, preferably trifluoromethoxy.

The term "heterocyclyl", as used herein, alone or in any combination, refers to a monocyclic, bicyclic or polycyclic non-aromatic ring system containing up to 15 ring atoms (preferably 5 to 10 ring atoms), at least one of these being a heteroatom, preferably one to three heteroatoms, independently selected from nitrogen, oxygen or sulfur, preferably nitrogen. This ring system may be saturated, partially saturated, or unsaturated, and preferably contains one or two ring heteroatoms selected from nitrogen. Representative examples of heterocyclyl include, but are not limited to, dihydroindolyl (especially dihydroindol-2-yl) and chromane (especially chroman-3-yl).

The term "heteroaryl", as used herein, alone or in any combination, has the meaning as defined for heterocyclyl above, with the difference that the ring system is aromatic.

The term "heteroarylalkyl", as used herein, alone or in any combination, refers to a heteroaryl group attached to the parent molecular moiety through an alkyl group. Representative examples of heteroarylalkyl include, but are not limited to, thienylalkyl (especially thien-2-ylalkyl), isoxazolylalkyl (especially 3-chloro-isoxazole-5-ylalkyl), pyridylalkyl (especially pyridine-3-ylalkyl), pyrimidylalkyl (especially pyrimidine-2-ylalkyl), indolylalkyl (especially indol-3-ylalkyl), and benzoimidazolylalkyl (especially benzoimidazol-2-ylalkyl).

The term "heteroarylcarbonyl", as used herein, alone or in any combination, refers to a heteroaryl group attached to the parent molecular moiety through a carbonyl group. A representative example of heteroarylcarbonyl includes, but is not limited to, indolylcarbonyl (especially indol-2-ylcarbonyl).

The term "heteroarylamino", as used herein, alone or in any combination, refers to a heteroaryl group attached to the parent molecular moiety through an amino group. A representative example of heteroarylamino includes, thiadiazolylamino (especially 1,3,4-thiadiazol-2-yl-amino).

The term "heterocyclylcarbonyl", as used herein, alone or in any combination, refers to a heterocyclyl group attached to the parent molecular moiety through a carbonyl group. A representative example of heterocyclylcarbonyl includes, dihydroindolylcarbonyl (especially dihydroindol-2-ylcarbonyl) and chromanecarbonyl (especially chroman-3-ylcarbonyl).

The term "hydroxy" or "hydroxyl" as used herein, alone or in any combination, refers to an —OH group The term "nitro", as used herein, alone or in any combination, refers to a —NO$_2$ group.

The term "oxo", as used herein, alone or in any combination, refers to an =O group.

The term "oxy", as used herein, alone or in any combination, refers to an —O— group.

The terms "sulfonyl", as used herein, alone or in any combination, refer to an —S(O)$_2$— group.

The term "acyl" as used herein refers to groups containing a carbonyl group that is linked to a carbon atom such as $C_{1-9}$-alkylcarbonyl, arylalkenylcarbonyl, aryl-$C_{1-6}$-alkylcarbonyl, aryl-$C_{1-3}$-alkoxy-$C_{1-3}$-alkylcarbonyl, arylcarbonyl, arylcarbonyl-$C_{1-4}$-alkylcarbonyl, aryloxy-$C_{1-3}$-alkylcarbonyl, cycloalkyl-$C_{1-3}$-alkylcarbonyl, diaryl-$C_{1-3}$-alkylcarbonyl, heterocyclylcarbonyl, heteroaryl-$C_{1-3}$-alkylcarbonyl, heteroarylcarbonyl, aryl-$C_{3-6}$-cycloalkylcarbonyl, cycloalkylcarbonyl, or $R^7$—$C_{1-4}$-alkylcarbonyl groups as used in $R^6$ of Formula I.

In analogy, the term "acylamino" as used herein refers to an acyl group as described before that is linked to the parent molecular moiety through a nitrogen atom.

The term "ureido" as used herein refers to groups such as $C_{1-9}$-alkylaminocarbonyl, arylaminocarbonyl, or aryl-$C_{1-3}$-alkylaminocarbonyl that are linked to the parent molecular moiety through a nitrogen atom.

The term "oxycarbonylamino" as used herein refers to groups such as $C_{1-9}$-alkoxycarbonyl, aryl-$C_{1-3}$-alkoxycarbonyl, or aryl-$C_{1-3}$-alkoxy-$C_{1-3}$-alkoxycarbonyl that are linked to the parent molecular moiety through a nitrogen atom.

The compounds of Formula I may contain one or more stereogenic or asymmetric centers, such as one or more asymmetric carbon atoms. Substituents at a double bond or a ring may be present in cis-(=Z-) or trans (=E-) form unless indicated otherwise. The compounds of Formula I may thus be present as mixtures of stereoisomers or preferably as pure stereoisomers. Mixtures of stereoisomers may be separated in a manner known to a person skilled in the art.

The compounds of the present invention have useful, in particular pharmacologically useful, properties. They bind to the CRTH2 receptor and thus modulate the effects of endogenous PGD$_2$. The compounds according to Formula I may be used for the preparation of a medicament, and are suitable, for the prevention and/or treatment of diseases selected from the group consisting of chronic and acute allergic/immune diseases/disorders, comprising allergic asthma, rhinitis, allergic rhinitis, chronic obstructive pulmonary disease (COPD), dermatitis, inflammatory bowel disease, rheumatoid arthritis, allergic nephritis, conjunctivitis, atopic dermatitis, bronchial asthma, food allergy, systemic mast cell disorders, anaphylactic shock, urticaria, eczema, itching, inflammation, ischemia-reperfusion injury, cerebrovascular disorders, pleuritis, ulcerative colitis, eosinophil-related diseases comprising Churg-Strauss syndrome and sinusitis, and basophil-related diseases, comprising basophilic leukemia and basophilic leukocytosis, in humans and other mammals.

A compound of Formula I or a pharmaceutical composition comprising a compound of Formula I may be used for the preparation of a medicament, and is suitable, for the prevention and/or treatment of diseases selected from the group consisting of both chronic and acute allergic/immune diseases/disorders such as those mentioned in the paragraph before, such as especially allergic asthma, rhinitis, allergic rhinitis, COPD, dermatitis, inflammatory bowel disease, and rheumatoid arthritis.

In another aspect, the compounds of Formula I may be used as standard or reference compounds in tests or assays involving the modulation of the CRTH2 receptor. Such compounds could be made commercially available for use as a reference, quality standard or control, for example in pharmaceutical research when developing new assays or protocols related to CRTH2 receptor activity.

As mentioned earlier, compounds of Formula I modulate the PGD$_2$ activation of the CRTH2 receptor. The biological effect of such compounds may be tested in a variety of in vitro, ex vivo and in vivo assays. The ability of the compounds of Formula I to bind to the CRTH2 receptor may be measured by methods similar to those described in the literature (Arimura A. et al., *J. Pharmacol. Exp. Ther.* 2001, 298(2), 411-419; and Sawyer N. et al., *Br. J. Pharmacol,* 2002, 137, 1163-1172, respectively) and by the assays described below in the experimental part.

A functional assay with cells expressing the human CRTH2 (hCRTH2) receptor may be used to detect changes in the levels of intracellular calcium concentration following compound treatment. After addition of the compound, the cells are challenged with PGD$_2$. In a Fluorescent Imaging Plate Reader (FLIPR™, Molecular Devices, Sunnyvale, Calif.), fluorescence emission is recorded during both additions, emission peak values above base level after $PGD_2$ addition are exported, and normalized to low controls (no $PGD_2$) and high controls (no active compound). The relative values of the remaining activity are used to determine $IC_{50}$ values by curve fitting the data to a single site to a four-parameter logistic sigmoid dose response curve of the equation $(A+((B-A)/(1+((C/x)^{\wedge}D))))$.

The ability of the compounds to modulate $PGD_2$ induced changes of intracellular calcium levels via CRTH2 receptor activation may be measured by methods known to one skilled in the art or by the assay described below in the experimental part.

The present invention relates also to pharmaceutical compositions comprising a compound of Formula I, or a pharmaceutically acceptable salt thereof, and a pharmaceutically acceptable carrier; to the use of such pharmaceutical compositions for the therapeutic, in a broader aspect of the invention also prophylactic, treatment of the diseases/disorders mentioned herein; to the compounds of Formula I, or pharmaceutically acceptable salts thereof, for use as a medicament; and to the use of a compound of Formula I, or a pharmaceutically acceptable salt thereof, for the preparation of a pharmaceutical composition for the prevention and/or treatment of the diseases/disorders mentioned herein.

The pharmaceutical compositions according to the invention are those for enteral administration, such as nasal, buccal, rectal, dermal or, especially oral administration, and for parenteral administration, such as intramuscular, intravenous or subcutaneous, intrasternal, intravitreal, injection or infusion, to warm-blooded animals, especially humans. Such compositions comprise an effective dose of the pharmaceutically active ingredient, alone or together with a pharmaceutically acceptable carrier. The dosage of the active ingredient depends on the species of warm-blooded animal, the body weight, the age and the individual conditions, individual pharmacokinetic data, the disease/disorder to be treated and the mode of administration.

The production of the pharmaceutical compositions can be effected in a manner which will be familiar to any person skilled in the art (see for example Mark Gibson, Editor, Pharmaceutical Preformulation and Formulation, IHS Health Group, Englewood, Colo., USA, 2001; Remington, *The Science and Practice of Pharmacy,* 20th Edition, Philadelphia College of Pharmacy and Science) by bringing the described compounds of Formula I or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

In one embodiment, the invention also relates to a method for the prevention or treatment of diseases/disorders that respond to an inhibition of the CRTH2 receptor in particular to a method for the prevention or treatment of the diseases/disorders mentioned herein, said methods comprising administering to a patient a pharmaceutically active amount of a compound of Formula I, or a pharmaceutically acceptable salt thereof.

A further aspect of the invention is a process for the preparation of compounds of Formula I. Compounds according to Formula I of the present invention can be prepared according to the sequence of reactions outlined in the schemes below wherein $R^1$, $R^2$, $R^3$, $R^4$, $R^5$, $R^6$ and $R^7$ are as defined for Formula I. Other abbreviations used are defined in the experimental section. In some instances the generic groups $R^1$, $R^2$, $R^3$, $R^4$, $R^5$, $R^6$ and $R^7$ might be incompatible with the assembly illustrated in the schemes below and, therefore, will require the use of protecting groups (PG). For example it may be necessary to protect reactive functional groups such as hydroxy, amino, imino, thio or carboxy groups, where these are desired in the final product, to avoid their unwanted participation in the reactions. The use of protecting groups is well known in the art (see for example "Protective Groups in Organic Synthesis", T. W. Greene, P. G. M. Wuts, Wiley-Interscience, 1999). It will be assumed that such protecting groups are as necessary in place. In the following description, for example, PG, when used as amino-protecting group, preferably refers to a group such as tert-butoxycarbonyl, benzyloxycarbonyl, or allyloxycarbonyl, most preferably tert-butoxycarbonyl. Further, L refers to a leaving group, such as activated (for examples as mesylate, active ester etc.) or non-activated hydroxy, or halo, in particular chloro or bromo. Further, R and R' independently refer to a $C_{1-4}$-alkyl group, preferably ethyl or tert-butyl, whereby when R' is present R is preferably ethyl and R' is preferably tert.-butyl.

In general, all chemical transformations can be performed according to well-known standard methodologies as described in the literature, for example those described by Larock R. C. in "*Comprehensive organic transformations: a guide to functional group preparations*", VCH publishers, 1999, or as described in the procedures below. The compounds obtained may also be converted into pharmaceutically acceptable salts thereof in a manner known per se.

Generally, compounds of Formula I are obtained from an ester of Structure 1, wherein R represents $C_{1-4}$-alkyl, preferably ethyl, or tert-butyl, by hydrolysis of the ester group using routine procedures, for example stirring an intermediate of Structure 1 with aq. lithium, sodium or potassium hydroxide in an organic co-solvent such as an alcohol, like MeOH or EtOH; THF; acetone; MeCN; or TFA, respectively.

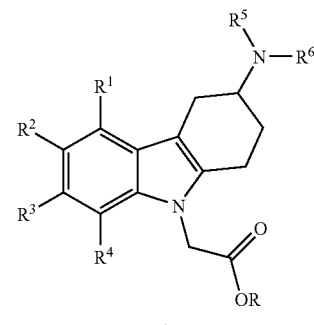

Structure 1, wherein R represents $C_{1-4}$-alkyl

An intermediate of Structure 1 is obtained by reacting an intermediate of Structure 2a or 2b, or a salt thereof, such as the hydrochloride salt, with a reagent of Formula L-$R^6$, wherein $R^6$ is as defined for Formula I and L is a leaving group as defined before. $R^6$ transferring reagent of Structure L-$R^6$ may be a chloroformate; or an acyl halide, preferably an acid chloride, or acid bromide, used as such; or generated in situ from the corresponding commercially available or well known carboxylic acid with an activating reagent, such as a halogenating reagent under conditions known to a skilled person, preferably by means of oxalyl chloride or phosphorous oxychloride; or an acyl anhydride, transferring $R^6$ in the presence of a base, such as $Et_3N$, DIEA, N-ethyl-morpholine, N-methylpiperidine, or pyridine, in a suitable solvent, such as THF, or DCM.

In another aspect, an intermediate of Structure 2a or 2b is condensed with a commercially available or well known carboxylic acid in the presence of a coupling reagent, such as DCC, diisopropylcarbodiimide, HATU and the like, in the presence of a base described hereinabove, to form an intermediate of Structure 1.

In a further aspect, an intermediate of Structure 2a or 2b is reacted with a commercially available isocyanate or isothiocyanate in the presence of a base to form an intermediate of Structure 1.

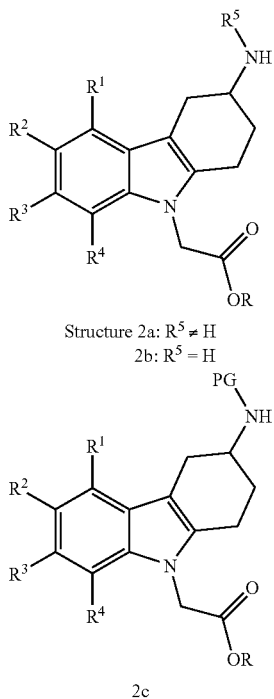

Structure 2a: $R^5 \neq H$
2b: $R^5 = H$

2c

In a specific case, intermediates of Structure 1, wherein $R^4$ represents an $C_{1-5}$-alkyl, allyl, vinyl, or a methanesulfonyl group, is obtained by reacting intermediates of Structure 2c wherein $R^4$ represents halogen, preferably I or Br, or a methanesulfonyloxy, or a toluenesulfonyloxy group, with reagents such as tetramethyltin, allyltributyltin, a complex of vinylboronic anhydride and pyridine together with a base, such as $K_2CO_3$, in the presence of a palladium catalyst such as tetrakis(triphenylphosphine)palladium(0), or the like, or sodium methanesulfinate in the presence of copper (I) iodide, respectively, in a polar aprotic solvent such as DMF, or DME, or NMP, at a temperature between 60° C. and 130° C.

A substituent $R^5$ in an intermediate of Structure 2a is obtained by reacting an intermediate of Structure 2b with the respective aldehyde in a solvent such as DCM or the like in presence of a reducing agent, such as sodium triacetoxyborohydride, and a base, such as DIEA.

Alternatively, an intermediate of Structure 2a, wherein $R^5$ is not hydrogen, is obtained from an intermediate of Structure 2b via a sulfonamide of Structure 3a. First, an intermediate of Structure 2b is reacted with p-nitrobenzenesulfonyl chloride in a solvent such as DCM, THF or another suitable organic solvent, in the presence of a base, such as DIEA, with or without a catalytic amount of N,N-dimethyl-aminopyridine, to afford the desired sulfonamide of Structure 3a. In a second step, in order to afford a sulfonamide of Structure 3b, the sulfonamide of Structure 3a is easily alkylated with the respective commercially available or well known alkylating agent $R^5$-L, with $K_2CO_3$ or any other suitable base, in an organic solvent, such as toluene, preferably in the presence of a phase transfer agent, such as tetrabutylammonium bromide in accordance to a procedure described in the literature (C. Peña et al., *Tetrahedron Lett.* 2005, 46, 2783-2787). Specifically, a methyl group is introduced by reaction of a sulfonamide of Structure 3a either with methyl iodide or with diazomethane dissolved in diethylether.

Subsequently, the sulfonamide of Structure 3b is treated in a typical procedure according to S. C. Miller and coworker (*J. Am. Chem. Soc.* 1997, 119, 2301-2302) with a thiol, such as thiophenol, or thioacetic acid, in the presence of a base, such as DBU or the like, in a suitable organic solvent, such as DMF, to remove the sulfonamido group, furnishing an intermediate of Structure 2a.

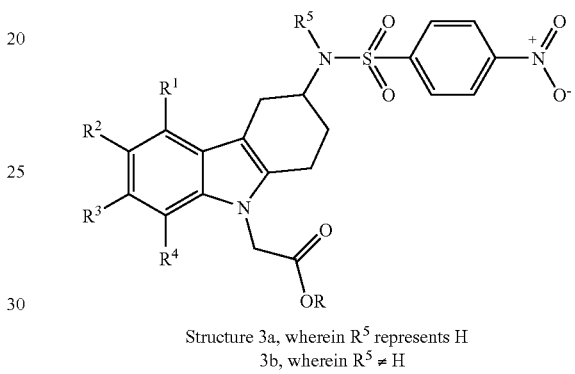

Structure 3a, wherein $R^5$ represents H
3b, wherein $R^5 \neq H$

An intermediate of Structure 2b is obtained after removal of the protective group (PG) from an intermediate of Structure 2c, applying reaction conditions known to a skilled person. Preferably, the PG is a group such as tert-butoxycarbonyl, benzyloxycarbonyl, or allyloxycarbonyl, most preferably tert-butoxycarbonyl.

An intermediate of Structure 2c is generated by reacting an intermediate of Structure 4 with a compound of Formula L-$CH_2CO_2R$ wherein R and L are as defined before, in the presence of a base, such as cesium carbonate, sodium hydride, potassium tert-butanolate or the like, in a suitable solvent, such as acetone, MeCN, THF or dioxane. Suitable L is a leaving group such as halo, in particular bromo or chloro; mesyloxy or tosyloxy. Preferably, the compound of Formula L-$CH_2CO_2R$ is ethyl bromoacetate.

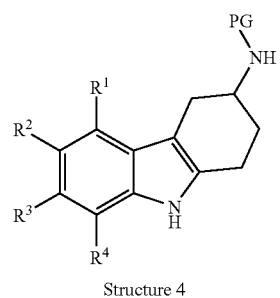

Structure 4

An intermediate of Structure 4, with PG as described hereinabove, is obtained in a Fischer-type indole synthesis according to the literature (J. D. Ha et al., *Bulletin of the Korean Soc. Chem.* 2004, 25, 1784-1790): reaction of a commercially available or well known hydrazine of Structure 5 (either as a free base or as a salt) and a cyclohexanone of Structure 6, which is commercially available or whose synthesis is as described in the above mentioned literature, furnishes the desired intermediate of Structure 4 as a racemate.

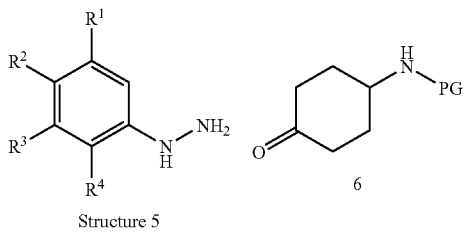

Structure 5

In another aspect, an intermediate of Structure 4 is obtained through protection of the amino group in a tetrahydrocarbazol-3-ylamine of Structure 7 with a hereinabove described PG applying methods known to a skilled person.

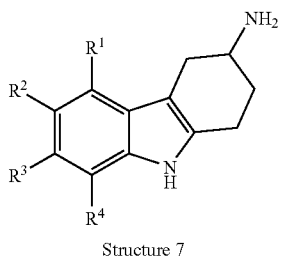

Structure 7

Both, the (R)- and the (S)-enantiomer of starting tetrahydrocarbazol-3-ylamine of Structure 7 are obtained in a stereospecific reaction following a procedure described in literature (Rosentreter U. et al., *Arzneim.-Forsch.* 1989, 39(12), 1519-1521; and EP 0242518).

A synthesis of racemic ethyl (3RS)-(3-amino-1,2,3,4-tetrahydro-9H-carbazol-9-yl)-acetate hydrochloride is described in the literature (Ulven, T.; Kostenis, E. *J. Med. Chem.* 2005, 48, 897-900).

A stereoselective synthesis of methyl (3R)-(3-tert-butoxycarbonylamino-1,2,3,4-tetrahydro-9H-carbazol-9-yl)-acetate is described in WO 03/097598.

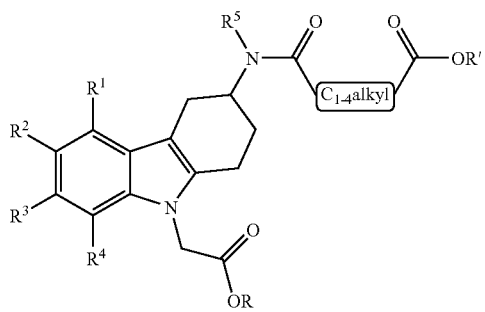

Structure 8a, wherein R' represents H and R represents $C_{1-4}$-alkyl
8b, wherein R' and R independently represent $C_{1-4}$-alkyl In a particular case, a compound of Structure 1, wherein $R^6$ represents "$R^7$—$C_{1-4}$-alkylcarbonyl, wherein the bridging $C_{1-4}$-alkyl group may additionally be mono-substituted with aryl, and $R^7$ represents arylaminocarbonyl, heteroarylaminocarbonyl, $C_{1-6}$-alkylaminocarbonyl, or aryl-$C_{1-3}$-alkylaminocarbonyl", is obtained by reaction of the respective compound of Structure 8a with the respective amine, in the presence of a coupling reagent, such as DCC, diisopropylcarbodiimide, HATU or the like, in the presence $Et_3N$, DIEA, or the like, in a solvent such as DCM or DMF.

A compound of Structure 8a wherein the bridging $C_{1-4}$-alkyl group may additionally be mono-substituted with aryl is obtained by treating a respective compound of Structure 8b, wherein R' represents $C_{1-4}$-alkyl, preferentially tent-butyl, as a protecting group, with reaction with TFA in DCM or hydrochloric acid in an organic solvent, such as dioxane, diethylether, AcOEt, or the like, at room temperature.

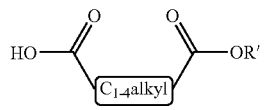

Structure 9, wherein R' represents $C_{1-4}$-alkyl

A compound of Structure 8b, is obtained by reacting a compound of Structure 2a or 2b with the corresponding compound of Structure 9, wherein the bridging $C_{1-4}$-alkyl group may additionally be mono-substituted with aryl, which are commercially available or synthesized according to well known methods such as enolate alkylation (see for example: J. Org. Chem. 1986, 51(6), 938-940), in the presence of a coupling reagent, such as DCC, diisopropylcarbodiimide, HATU, or the like, in the presence of a base such as $Et_3N$, DIEA, or the like, in a solvent such as DCM or DMF.

Whenever the compounds of Formula I are obtained in the form of mixtures of enantiomers, the enantiomers can be separated using methods known to the one skilled in the art: e.g. by formation and separation of diastereomeric salts or by HPLC over a chiral stationary phase such as a Regis Whelk-O1(R,R) (10 μm) column, a Daicel ChiralCel OD-H (5-10 μm) column, or a Daicel ChiralPak IA (10 μm) or AD-H (5 μm) column. Typical conditions of chiral HPLC are an isocratic mixture of eluent A (EtOH, in presence or absence of an amine such as $Et_3N$, diethylamine) and eluent B (hexane), at a flow rate of 0.8 to 150 mL/min.

EXPERIMENTAL SECTION

Abbreviations (as Used Herein)

AcOEt Ethyl acetate
AcOH Acetic acid
aq. aqueous
Bdg Binding
BSA Bovine Serum Albumin
CC Column chromatography on silica gel
DBU 1,8-Diazabicyclo[5.4.0]undec-7-ene
DCC 1,3-Dicyclohexylcarbodiimide
DCM Dichloromethane
DIEA N,N-Diisopropylethylamine
DMAP N,N-Dimethyl-4-aminopyridine
DME Dimethoxyethane
DMF Dimethylformamide
DMSO Dimethylsulfoxide
EDTA Ethylene Diamine Tetraacetic Acid
ESI-MS Electrospray Ionization Mass Spectroscopy
$Et_3N$ Triethylamine
FC Flash chromatography on silica gel h hour(s)
HATU O-(7-Aza-1H-benzotriazole-1-yl)-1,1,3,3-tetramethyluronium hexafluorophosphate
HPLC High Performance Liquid Chromatography
l liter(s)
LC-MS Liquid Chromatography-Mass Spectroscopy
Me Methyl
MeCN Acetonitrile
MeI Methyl iodide
MeOH Methanol
mesyl Methanesulfonyl
Meth. Method
min minute(s)
MS Mass Spectroscopy
MW Molecular Weight
N Normality of solution
$NaBH(OAc)_3$ Sodium triacetoxyborohydride
NMP N-Methylpyrrolidinone
org. organic
PBS Phosphate Buffered Saline
PG Protecting Group
$PGD_2$ Prostaglandin $D_2$
PMSF Phenylmethylsulfonyl fluoride
rt room temperature
s second(s)
sat. saturated
subst. substituted
TFA Trifluoroacetic acid
THF Tetrahydrofuran
tlc thin layer chromatography
tosyl Toluenesulfonyl
$t_R$ retention time
Tris Tris-(hydroxymethyl)aminomethane buffer
Chemistry
General Remarks All solvents and reagents are used as obtained from commercial sources unless otherwise indicated.

Temperatures are indicated in degrees Celsius (° C.). Unless otherwise indicated, the reactions take place at room temperature (rt).

In mixtures, relations of parts of solvent or eluent or reagent mixtures in liquid form are given as volume relations (v/v), unless indicated otherwise.

Analytical HPLC conditions as used in the Examples below:

HPLC/MS analyses are performed on a Waters 2795 Alliance HPLC instrument, equipped with a Waters 996 Photodiode Array Detector and a Micromass ZQ™ Waters mass spectrometer (electron spray ionization), detection at 200-400 nm (LC-1 and LC-2), or on a Agilent 1100 system, equipped with a Dionex P580 binary pump, a Dionex PDA-100 Photodiode Array Detector and a Finnigan AQA mass spectrometer (LC-3).

The LC retention times are obtained using the following elution conditions:

LC-1: Analytical HPLC on a Xterra™ MS C18 column (4.6×50 mm, 5 μm, Waters); Linear gradient of water/ 0.06% formic acid (A) and MeCN/0.06% formic acid (B) from 5% to 95% B over 1 min; flow rate 3 ml/min, detection at 215 nm.

LC-2: Analytical HPLC on a Zorbax® SB-AQ column (4.6×50 mm, 5 μm, Agilent); Linear gradient of water/ 0.06% formic acid (A) and MeCN/0.06% formic acid (B) from 5% to 95% B over 1 min; flow rate 3 ml/min, detection at 215 nm.

LC-3: Analytical HPLC on a Zorbax® SB-AQ column (4.6×50 mm, 5 μm, Agilent); Linear gradient of water/ 0.05% TFA (A) and MeCN (B) from 5% to 95% B over 1 min; flow rate 4.5 ml/min, detection at 215 nm.

Preparative HPLC/MS purifications are performed on a Waters HPLC system, equipped with a Waters 600 controller, a Waters 2767 sample manager, a Waters 996 Photodiode Array Detector, and a Micromass ZQ™ Waters mass spectrometer (electron spray ionization), detection at 200-400 nm, using a Zorbax® PrepHT SB.Aq (5 μm, 21.2×50 mm) or a Phenomenex® Gemini column (10 μm, 21.2×50 mm), with a linear gradient of water/0.02% formic acid (A) and MeCN/ 0.02% formic acid (B) over 5 min; flow rate 4 ml/min, detection at 215 nm.

$^1$H NMR spectra are recorded either on a Varian Mercury 300VX FT-NMR spectrometer or on a Bruker Advance II 400 spectometer. Chemical shifts (δ) are reported in parts per million (ppm) relative to proton resonances resulting from incomplete deuteration of the NMR solvent, e.g. for dimethylsulfoxide δ(H) 2.49 ppm, for chloroform δ(H) 7.24 ppm, and the abbreviations s, d, t, q, m and br refer to singlet, doublet, triplet, quartet, multiplet, and broad, respectively.

Synthesis of Compounds of Formula I:

The following examples illustrate the preparation of pharmacologically active compounds of the invention but do not at all limit the scope thereof. First the synthesis of Example compounds is described, followed by the description of the synthesis of intermediates and starting materials. Whenever used in the experimental part, generic Structures 1 to 9 refer to the Structures described in preceeding general description of the preparation of compounds of Formula I.

General Method for Saponification of Intermediates of Structure 1:

Aq. 1N LiOH or 1N NaOH (1 ml, 1 mmol) is added to a stirred solution of the appropriate compound of Structure 1 (0.105 mmol) in THF (1 ml) and the resulting biphasic mixture is continued to stir overnight. DCM (2 ml) and AcOH (1 ml), or 2N HCl, are added to the reaction mixture. The aq. layer, obtained after phase separation, is extracted three times with DCM (1 ml). The combined org. phases are washed with brine and dried over $Na_2SO_4$ and the solvent is evaporated. Purification is performed by CC with a 1:1 mixture of AcOEt/ heptane containing 1% AcOH, or by preparative HPLC to give the desired compound of Formula I in 6 to 98% yield.

Listed in Table 1 below are examples of compounds of Formula I, prepared according to the above-mentioned method with the corresponding compound of Structure 1 as starting material.

TABLE 1

| Example | Compound of Formula I | Formula MW | $t_R$ [min] LC-MS Method | MS Data m/z $[M + H]^+$ |
|---|---|---|---|---|
| 1 | (3R)-[3-(3-Butyl-ureido)-1,2,3,4-tetrahydro-9H-carbazol-9-yl]-acetic acid | C19H25N3O3 343.426 | 1.01 LC-1 | 344.08 |
| 2 | (3R)-[3-(3-Benzyl-ureido)-1,2,3,4-tetrahydro-9H-carbazol-9-yl]-acetic acid | C22H23N3O3 377.443 | 1.15 LC-1 | 378.04 |

TABLE 1-continued

| Example | Compound of Formula I | Formula MW | $t_R$ [min] LC-MS Method | MS Data m/z [M + H]⁺ |
|---|---|---|---|---|
| 3 | (3R)-[3-(3-Phenethyl-ureido)-1,2,3,4-tetrahydro-9H-carbazol-9-yl]-acetic acid | C23H25N3O3 391.47 | 1.32 LC-1 | 392.05 |
| 4 | (3R)-[3-(3-Naphthalen-1-yl-ureido)-1,2,3,4-tetrahydro-9H-carbazol-9-yl]-acetic acid | C25H23N3O3 413.476 | 1.7 LC-1 | 413.97 |
| 5 | (3R)-[3-(3-Phenylsulfonyl-ureido)-1,2,3,4-tetrahydro-9H-carbazol-9-yl]-acetic acid | C21H21N3O5S 427.48 | 1.13 LC-1 | [M + Na]⁺ 449.90 |
| 6 | (3R)-(3-tert-Butoxycarbonylamino-1,2,3,4-tetrahydro-9H-carbazol-9-yl)-acetic acid | C19H24N2O4 344.10 | 1.05 LC-1 | [M + Na]⁺ 367.07 |
| 7 | (3R)-(3-Propoxycarbonylamino-1,2,3,4-tetrahydro-9H-carbazol-9-yl)-acetic acid | C18H22N2O4 330.383 | 1.35 LC-1 | 331.03 |
| 8 | (3R)-(3-Isobutoxycarbonylamino-1,2,3,4-tetrahydro-9H-carbazol-9-yl)-acetic acid | C19H24N2O4 344.41 | 1.69 LC-1 | 345.03 |
| 9 | (3R)-(3-Benzyloxycarbonylamino-1,2,3,4-tetrahydro-9H-carbazol-9-yl)-acetic acid | C22H22N2O4 378.427 | 1.82 LC-1 | [M + Na]⁺ 400.96 |
| 10 | (3R)-[3-(2-Benzyloxy-ethoxycarbonylamino)-1,2,3,4-tetrahydro-9H-carbazol-9-yl]-acetic acid | C24H26N2O5 422.479 | 1.77 LC-1 | [M + Na]⁺ 444.94 |
| 11 | (3R)-(3-Benzoylamino-1,2,3,4-tetrahydro-9H-carbazol-9-yl)-acetic acid | C21H20N2O3 348.401 | 1.00 LC-2 | 349.00 |
| 12 | (3R)-[3-(2-Phenoxy-acetylamino)-1,2,3,4-tetrahydro-9H-carbazol-9-yl]-acetic acid | C22H22N2O4 378.427 | 1.43 LC-1 | 379.04 |
| 13 | (3R)-(3-Phenylacetylamino-1,2,3,4-tetrahydro-9H-carbazol-9-yl)-acetic acid | C22H22N2O3 362.428 | 1.21 LC-1 | 363.02 |
| 14 | (3R)-[3-(2-Thiophen-2-yl-acetylamino)-1,2,3,4-tetrahydro-9H-carbazol-9-yl]-acetic acid | C20H20N2O3S 368.456 | 1.11 LC-1 | 368.96 |
| 15 | (3R)-[3-(3-Phenyl-propionylamino)-1,2,3,4-tetrahydro-9H-carbazol-9-yl]-acetic acid | C23H24N2O3 376.455 | 1.36 LC-1 | 377.04 |
| 16 | (3R)-[3-(2-Benzyloxy-acetylamino)-1,2,3,4-tetrahydro-9H-carbazol-9-yl]-acetic acid | C23H24N2O4 392.454 | 1.44 LC-1 | 392.98 |
| 17 | (3R)-[3-(3-Methyl-butyrylamino)-1,2,3,4-tetrahydro-9H-carbazol-9-yl]-acetic acid | C19H24N2O3 328.411 | 0.97 LC-1 | 329.08 |
| 18 | (3R)-[3-(3-Cyclopentyl-propionylamino)-1,2,3,4-tetrahydro-9H-carbazol-9-yl]-acetic acid | C22H28N2O3 368.475 | 1.77 LC-1 | 369.07 |
| 19 | (3R)-(3-Decanoylamino-1,2,3,4-tetrahydro-9H-carbazol-9-yl)-acetic acid | C24H34N2O3 398.545 | 2.77 LC-1 | 399.10 |
| 20 | (3S)-[3-(3-Butyl-ureido)-1,2,3,4-tetrahydro-9H-carbazol-9-yl]-acetic acid | C19H25N3O3 343.426 | 0.98 LC-2 | 344.18 |
| 21 | (3S)-[3-(3-Benzyl-ureido)-1,2,3,4-tetrahydro-9H-carbazol-9-yl]-acetic acid | C22H23N3O3 377.443 | 0.99 LC-2 | 378.18 |
| 22 | (3S)-[3-(3-Phenethyl-ureido)-1,2,3,4-tetrahydro-9H-carbazol-9-yl]-acetic acid | C23H25N3O3 391.47 | 1.01 LC-2 | 392.17 |
| 23 | (3S)-[3-(3-Phenylsulfonyl-ureido)-1,2,3,4-tetrahydro-9H-carbazol-9-yl]-acetic acid | C21H21N3O5S 427.48 | 0.99 LC-2 | 428.05 |
| 24 | (3S)-[3-(3-Phenyl-ureido)-1,2,3,4-tetrahydro-9H-carbazol-9-yl]-acetic acid | C21H21N3O3 363.416 | 1.00 LC-2 | 364.13 |
| 25 | (3S)-(3-Propoxycarbonylamino-1,2,3,4-tetrahydro-9H-carbazol-9-yl)-acetic acid | C18H22N2O4 330.383 | 1.01 LC-2 | 331.17 |
| 26 | (3S)-(3-Isobutoxycarbonylamino-1,2,3,4-tetrahydro-9H-carbazol-9-yl)-acetic acid | C19H24N2O4 344.41 | 1.04 LC-2 | 345.15 |
| 27 | (3S)-(3-Benzyloxycarbonylamino-1,2,3,4-tetrahydro-9H-carbazol-9-yl)-acetic acid | C22H22N2O4 378.427 | 1.06 LC-2 | 379.15 |
| 28 | (3S)-[3-(2-Benzyloxy-ethoxycarbonylamino)-1,2,3,4-tetrahydro-9H-carbazol-9-yl]-acetic acid | C24H26N2O5 422.479 | 1.06 LC-2 | 423.20 |
| 29 | (3S)-[3-(2-Phenoxy-acetylamino)-1,2,3,4-tetrahydro-9H-carbazol-9-yl]-acetic acid | C22H22N2O4 378.427 | 1.02 LC-2 | 379.08 |
| 30 | (3S)-(3-Phenylacetylamino-1,2,3,4-tetrahydro-9H-carbazol-9-yl)-acetic acid | C22H22N2O3 362.428 | 1.00 LC-2 | 363.16 |
| 31 | (3S)-[3-(2-Thiophen-2-yl-acetylamino)-1,2,3,4-tetrahydro-9H-carbazol-9-yl]-acetic acid | C20H20N2O3S 368.456 | 0.99 LC-2 | 369.11 |
| 32 | (3S)-[3-(3-Phenyl-propionylamino)-1,2,3,4-tetrahydro-9H-carbazol-9-yl]-acetic acid | C23H24N2O3 376.455 | 1.02 LC-2 | 377.08 |
| 33 | (3S)-[3-(2-Benzyloxy-acetylamino)-1,2,3,4-tetrahydro-9H-carbazol-9-yl]-acetic acid | C23H24N2O4 392.454 | 1.03 LC-2 | 393.14 |
| 34 | (3S)-[3-(3-Methyl-butyrylamino)-1,2,3,4-tetrahydro-9H-carbazol-9-yl]-acetic acid | C19H24N2O3 328.411 | 0.97 LC-2 | 329.16 |
| 35 | (3S)-[3-(3-Cyclopentyl-propionylamino)-1,2,3,4-tetrahydro-9H-carbazol-9-yl]-acetic acid | C22H28N2O3 368.475 | 1.01 LC-2 | 369.18 |
| 36 | (3S)-(3-Decanoylamino-1,2,3,4-tetrahydro-9H-carbazol-9-yl)-acetic acid | C24H34N2O3 398.545 | 1.16 LC-2 | 398.82 |

TABLE 1-continued

| Example | Compound of Formula I | Formula MW | $t_R$ [min] LC-MS Method | MS Data m/z [M + H]⁺ |
|---------|----------------------|------------|--------------------------|----------------------|
| 37 | (3S)-(3-Butyrylamino-1,2,3,4-tetrahydro-9H-carbazol-9-yl)-acetic acid | C18H22N2O3 314.384 | 0.94 LC-2 | 315.18 |
| 38 | (3S)-(3-Heptanoylamino-1,2,3,4-tetrahydro-9H-carbazol-9-yl)-acetic acid | C21H28N2O3 356.464 | 1.06 LC-2 | 357.20 |
| 39 | (3R)-[6-Fluoro-3-(2-phenoxy-acetylamino)-1,2,3,4-tetrahydro-9H-carbazol-9-yl]-acetic acid | C22H21N2O4F 396.417 | 1.04 LC-2 | 397.16 |
| 40 | (3R)-(6-Fluoro-3-phenylacetylamino-1,2,3,4-tetrahydro-9H-carbazol-9-yl)-acetic acid | C22H21N2O3F 380.418 | 1.01 LC-2 | 381.16 |
| 41 | (3R)-[6-Fluoro-3-(3-phenyl-propionylamino)-1,2,3,4-tetrahydro-9H-carbazol-9-yl]-acetic acid | C23H23N2O3F 394.445 | 1.03 LC-2 | 395.22 |
| 42 | (3R)-{3-[2-(4-Chloro-phenyl)-acetylamino]-6-fluoro-1,2,3,4-tetrahydro-9H-carbazol-9-yl}-acetic acid | C22H20N2O3ClF 414.863 | 1.05 LC-2 | 415.16 |
| 43 | (3R)-{6-Fluoro-3-[2-(4-methoxy-phenyl)-acetylamino]-1,2,3,4-tetrahydro-9H-carbazol-9-yl}-acetic acid | C23H23N2O4F 410.444 | 1.01 LC-2 | 411.22 |
| 44 | (3R)-[6-Fluoro-3-(2-p-tolyl-acetylamino)-1,2,3,4-tetrahydro-9H-carbazol-9-yl]-acetic acid | C23H23N2O3F 394.445 | 1.04 LC-2 | 395.22 |
| 45 | (3R)-{3-[2-(3,4-Dichloro-phenyl)-acetylamino]-6-fluoro-1,2,3,4-tetrahydro-9H-carbazol-9-yl}-acetic acid | C22H19N2O3Cl2F 449.308 | 1.09 LC-2 | 447.16 |
| 46 | (3R)-{3-[2-(3-Chloro-phenyl)-acetylamino]-6-fluoro-1,2,3,4-tetrahydro-9H-carbazol-9-yl}-acetic acid | C22H20N2O3ClF 414.863 | 1.06 LC-2 | 415.16 |
| 47 | (3R)-{6-Fluoro-3-[2-(4-trifluoromethyl-phenyl)-acetylamino]-1,2,3,4-tetrahydro-9H-carbazol-9-yl}-acetic acid | C23H20N2O3F4 448.415 | 1.08 LC-2 | 449.17 |
| 48 | (3R)-{3-[2-(4-Chloro-phenoxy)-acetylamino]-6-fluoro-1,2,3,4-tetrahydro-9H-carbazol-9-yl}-acetic acid | C22H20N2O4ClF 430.862 | 1.08 LC-2 | 431.16 |
| 49 | (3R)-[6-Fluoro-3-(2-p-tolyloxy-acetylamino)-1,2,3,4-tetrahydro-9H-carbazol-9-yl]-acetic acid | C23H23N2O4F 410.444 | 1.08 LC-2 | 411.22 |
| 50 | (3R)-{3-[2-(2-Chloro-phenoxy)-acetylamino]-6-fluoro-1,2,3,4-tetrahydro-9H-carbazol-9-yl}-acetic acid | C22H20N2O4ClF 430.862 | 1.07 LC-2 | 431.16 |
| 51 | (3R)-{3-[2-(3-Chloro-phenoxy)-acetylamino]-6-fluoro-1,2,3,4-tetrahydro-9H-carbazol-9-yl}-acetic acid | C22H20N2O4ClF 430.862 | 1.08 LC-2 | 431.16 |
| 52 | (3R)-{6-Fluoro-3-[3-(4-methoxy-phenyl)-propionylamino]-1,2,3,4-tetrahydro-9H-carbazol-9-yl}-acetic acid | C24H25N2O4F 424.471 | 1.03 LC-2 | 425.28 |
| 53 | (3R)-[6-Fluoro-3-(3-p-tolyl-propionylamino)-1,2,3,4-tetrahydro-9H-carbazol-9-yl]-acetic acid | C24H25N2O3F 408.472 | 1.06 LC-2 | 409.21 |
| 54 | (3R)-{3-[3-(4-Chloro-phenyl)-propionylamino]-6-fluoro-1,2,3,4-tetrahydro-9H-carbazol-9-yl}-acetic acid | C23H22N2O3ClF 428.89 | 1.07 LC-2 | 429.15 |
| 55 | (3R)-{3-[3-(2-Chloro-phenyl)-propionylamino]-6-fluoro-1,2,3,4-tetrahydro-9H-carbazol-9-yl}-acetic acid | C23H22N2O3ClF 428.89 | 1.07 LC-2 | 429.15 |
| 56 | (3R)-{3-[3-(3-Chloro-phenyl)-propionylamino]-6-fluoro-1,2,3,4-tetrahydro-9H-carbazol-9-yl}-acetic acid | C23H22N2O3ClF 428.89 | 1.07 LC-2 | 429.15 |
| 57 | (3S)-{3-[2-(4-Chloro-phenyl)-acetylamino]-6-fluoro-1,2,3,4-tetrahydro-9H-carbazol-9-yl}-acetic acid | C22H20N2O3ClF 414.863 | 1.05 LC-2 | 415.23 |
| 58 | (3S)-{6-Fluoro-3-[2-(4-methoxy-phenyl)-acetylamino]-1,2,3,4-tetrahydro-9H-carbazol-9-yl}-acetic acid | C23H23N2O4F 410.444 | 1.01 LC-2 | 411.22 |
| 59 | (3S)-[6-Fluoro-3-(2-p-tolyl-acetylamino)-1,2,3,4-tetrahydro-9H-carbazol-9-yl]-acetic acid | C23H23N2O3F 394.445 | 1.01 LC-2 | 395.15 |
| 60 | (3S)-[6-Fluoro-3-(2-phenoxy-acetylamino)-1,2,3,4-tetrahydro-9H-carbazol-9-yl]-acetic acid | C22H21N2O4F 396.417 | 1.04 LC-2 | 397.23 |
| 61 | (3S)-[6-Fluoro-3-(3-phenyl-propionylamino)-1,2,3,4-tetrahydro-9H-carbazol-9-yl]-acetic acid | C23H23N2O3F 394.445 | 1.03 LC-2 | 395.22 |
| 62 | (3S)-{3-[2-(4-Chloro-phenoxy)-acetylamino]-6-fluoro-1,2,3,4-tetrahydro-9H-carbazol-9-yl}-acetic acid | C22H20N2O4ClF 430.862 | 1.08 LC-2 | 431.16 |

TABLE 1-continued

| Example | Compound of Formula I | Formula MW | $t_R$ [min] LC-MS Method | MS Data m/z [M + H]$^+$ |
|---|---|---|---|---|
| 63 | (3S)-[6-Fluoro-3-(2-p-tolyloxy-acetylamino)-1,2,3,4-tetrahydro-9H-carbazol-9-yl]-acetic acid | C23H23N2O4F 410.444 | 1.07 LC-2 | 411.22 |
| 64 | (3S)-{6-Fluoro-3-[3-(4-methoxy-phenyl)-propionylamino]-1,2,3,4-tetrahydro-9H-carbazol-9-yl}-acetic acid | C24H25N2O4F 424.471 | 1.03 LC-2 | 425.21 |
| 65 | (3S)-[6-Fluoro-3-(3-p-tolyl-propionylamino)-1,2,3,4-tetrahydro-9H-carbazol-9-yl]-acetic acid | C24H25N2O3F 408.472 | 1.06 LC-2 | 409.21 |
| 66 | (3S)-{3-[3-(4-Chloro-phenyl)-propionylamino]-6-fluoro-1,2,3,4-tetrahydro-9H-carbazol-9-yl}-acetic acid | C23H22N2O3ClF 428.89 | 1.07 LC-2 | 429.15 |
| 67 | (3S)-{3-[3-(2-Chloro-phenyl)-propionylamino]-6-fluoro-1,2,3,4-tetrahydro-9H-carbazol-9-yl}-acetic acid | C23H22N2O3ClF 428.89 | 1.07 LC-2 | 429.15 |
| 68 | (3S)-{3-[3-(3-Chloro-phenyl)-propionylamino]-6-fluoro-1,2,3,4-tetrahydro-9H-carbazol-9-yl}-acetic acid | C23H22N2O3ClF 428.89 | 1.07 LC-2 | 429.15 |
| 69 | (3S)-{3-[3-(3,4-Difluoro-phenyl)-propionylamino]-6-fluoro-1,2,3,4-tetrahydro-9H-carbazol-9-yl}-acetic acid | C23H21N2O3F3 430.425 | 1.05 LC-2 | 431.26 |
| 70 | (3S)-{6-Fluoro-3-[3-(3-methoxy-phenyl)-propionylamino]-1,2,3,4-tetrahydro-9H-carbazol-9-yl}-acetic acid | C24H25N2O4F 424.471 | 1.03 LC-2 | 425.21 |
| 71 | (3S)-{6-Fluoro-3-[3-(2-methoxy-phenyl)-propionylamino]-1,2,3,4-tetrahydro-9H-carbazol-9-yl}-acetic acid | C24H25N2O4F 424.471 | 1.04 LC-2 | 425.21 |
| 72 | (3S)-[3-(2,3-Diphenyl-propionylamino)-6-fluoro-1,2,3,4-tetrahydro-9H-carbazol-9-yl]-acetic acid | C29H27N2O3F 470.542 | 1.12 LC-2 | 471.27 |
| 73 | (3S)-[3-(3,3-Diphenyl-propionylamino)-6-fluoro-1,2,3,4-tetrahydro-9H-carbazol-9-yl]-acetic acid | C29H27N2O3F 470.542 | 1.1 LC-2 | 471.20 |
| 74 | (3S)-{3-[4-(4-Bromo-phenyl)-4-oxo-butyrylamino]-6-fluoro-1,2,3,4-tetrahydro-9H-carbazol-9-yl}-acetic acid | C24H22N2O4BrF 501.351 | 1.07 LC-2 | 503.06 |
| 75 | (3S)-[6-Fluoro-3-(4-oxo-4-phenyl-butyrylamino)-1,2,3,4-tetrahydro-9H-carbazol-9-yl]-acetic acid | C24H23N2O4F 422.455 | 1.02 LC-2 | 423.20 |
| 76 | (3S)-{6-Fluoro-3-[4-(4-methanesulfonyl-phenyl)-4-oxo-butyrylamino]-1,2,3,4-tetrahydro-9H-carbazol-9-yl}-acetic acid | C25H25N2O6FS 500.545 | 0.97 LC-2 | 501.19 |
| 77 | (3S)-[6-Fluoro-3-(2-indan-2-yl-acetylamino)-1,2,3,4-tetrahydro-9H-carbazol-9-yl]-acetic acid | C25H25N2O3F 420.483 | 1.07 LC-2 | 421.19 |
| 78 | (3S)-{6-Fluoro-3-[3-(4-hydroxy-3-methoxy-phenyl)-propionylamino]-1,2,3,4-tetrahydro-9H-carbazol-9-yl}-acetic acid | C24H25N2O5F 440.47 | 0.98 LC-2 | 441.00 |
| 79 | (3S)-{6-Fluoro-3-[3-(4-hydroxy-phenyl)-propionylamino]-1,2,3,4-tetrahydro-9H-carbazol-9-yl}-acetic acid | C23H23N2O4F 410.444 | 0.97 LC-2 | 411.02 |
| 80 | (3S)-{6-Fluoro-3-[3-(3-hydroxy-phenyl)-propionylamino]-1,2,3,4-tetrahydro-9H-carbazol-9-yl}-acetic acid | C23H23N2O4F 410.444 | 0.99 LC-2 | 411.02 |
| 81 | (3S)-{6-Fluoro-3-[3-(2-hydroxy-phenyl)-propionylamino]-1,2,3,4-tetrahydro-9H-carbazol-9-yl}-acetic acid | C23H23N2O4F 410.444 | 1.02 LC-2 | 411.02 |
| 82 | (3S)-{3-[(2,3-Dihydro-1H-indole-2-carbonyl)-amino]-6-fluoro-1,2,3,4-tetrahydro-9H-carbazol-9-yl}-acetic acid | C23H22N3O3F 407.444 | 1.04 LC-2 | 408.04 |
| 83 | (3S)-[6-Fluoro-3-(3-1H-indol-3-yl-propionylamino)-1,2,3,4-tetrahydro-9H-carbazol-9-yl]-acetic acid | C25H24N3O3F 433.482 | 1.04 LC-2 | 434.07 |
| 84 | (3S)-[3-(3-1H-Benzoimidazol-2-yl-propionylamino)-6-fluoro-1,2,3,4-tetrahydro-9H-carbazol-9-yl]-acetic acid | C24H23N4O3F 434.47 | 0.79 LC-2 | 435.04 |
| 85 | (3S)-[3-(3-Benzo[1,3]dioxol-5-yl-propionylamino)-6-fluoro-1,2,3,4-tetrahydro-9H-carbazol-9-yl]-acetic acid | C24H23N2O5F 438.454 | 1.04 LC-2 | 438.99 |
| 86 | (3S)-{6-Fluoro-3-[(1H-indole-2-carbonyl)-amino]-1,2,3,4-tetrahydro-9H-carbazol-9-yl}-acetic acid | C23H20N3O3F 405.428 | 1.07 LC-2 | 406.03 |
| 87 | (3S)-[6-Fluoro-3-(3-pyridin-3-yl-propionylamino)-1,2,3,4-tetrahydro-9H-carbazol-9-yl]-acetic acid | C22H22N3O3F 395.433 | 0.7 LC-3 | 396.11 |

TABLE 1-continued

| Example | Compound of Formula I | Formula MW | $t_R$ [min] LC-MS Method | MS Data m/z [M + H]+ |
|---|---|---|---|---|
| 88 | (3S)-{3-[2-(4-tert-Butyl-phenyl)-acetylamino]-6-fluoro-1,2,3,4-tetrahydro-9H-carbazol-9-yl}-acetic acid | C26H29N2O3F 436.525 | 1.02 LC-3 | 437.17 |
| 89 | (3S)-{6-Fluoro-3-[2-(4-trifluoromethyl-phenyl)-acetylamino]-1,2,3,4-tetrahydro-9H-carbazol-9-yl}-acetic acid | C23H20N2O3F4 448.415 | 0.98 LC-3 | 449.14 |
| 90 | (3S)-{6-Fluoro-3-[2-(3-trifluoromethyl-phenyl)-acetylamino]-1,2,3,4-tetrahydro-9H-carbazol-9-yl}-acetic acid | C23H20N2O3F4 448.415 | 0.98 LC-3 | 449.09 |
| 91 | (3S)-{6-Fluoro-3-[2-(4-trifluoromethyl-phenoxy)-acetylamino]-1,2,3,4-tetrahydro-9H-carbazol-9-yl}-acetic acid | C23H20N2O4F4 464.414 | 1.00 LC-3 | 465.15 |
| 92 | (3S)-[6-Fluoro-3-(3-naphthalen-2-yl-acryloylamino)-1,2,3,4-tetrahydro-9H-carbazol-9-yl]-acetic acid | C27H23N2O3F 442.489 | 1.01 LC-3 | 443.07 |
| 93 | (3S)-[6-Fluoro-3-(3-naphthalen-2-yl-propionylamino)-1,2,3,4-tetrahydro-9H-carbazol-9-yl]-acetic acid | C27H25N2O3F 444.505 | 0.99 LC-3 | 445.15 |
| 94 | (3S)-{6-Fluoro-3-[methyl-(3-phenyl-propionyl)-amino]-1,2,3,4-tetrahydro-9H-carbazol-9-yl}-acetic acid | C24H25N2O3F 408.472 | 0.98 LC-3 | 409.16 |
| 95 | (3S)-(3-{[2-(4-Chloro-phenyl)-acetyl]-methyl-amino}-6-fluoro-1,2,3,4-tetrahydro-9H-carbazol-9-yl)-acetic acid | C23H22N2O3ClF 428.89 | 0.99 LC-3 | 429.10 |
| 96 | (3S)-{6-Fluoro-3-[ethyl-(3-phenyl-propionyl)-amino]-1,2,3,4-tetrahydro-9H-carbazol-9-yl}-acetic acid | C25H27N2O3F 422.498 | 0.99 LC-3 | 423.10 |
| 97 | (3S)-(3-{[2-(4-Chloro-phenyl)-acetyl]-ethyl-amino}-6-fluoro-1,2,3,4-tetrahydro-9H-carbazol-9-yl)-acetic acid | C24H24N2O3ClF 442.917 | 1.01 LC-3 | 443.06 |
| 98 | (3S)-{6-Fluoro-3-[propyl-(3-phenyl-propionyl)-amino]-1,2,3,4-tetrahydro-9H-carbazol-9-yl}-acetic acid | C26H29N2O3F 436.525 | 1.02 LC-3 | 437.20 |
| 99 | (3S)-(3-{[2-(4-Chloro-phenyl)-acetyl]-propyl-amino}-6-fluoro-1,2,3,4-tetrahydro-9H-carbazol-9-yl)-acetic acid | C25H26N2O3ClF 456.943 | 1.03 LC-3 | 457.21 |
| 100 | (3RS)-(3-Benzyloxycarbonylamino-6-fluoro-1,2,3,4-tetrahydro-9H-carbazol-9-yl)-acetic acid | C22H21N2O4F 396.410 | 0.98 LC-3 | 397.11 |
| 101 | (3RS)-(3-Benzyloxycarbonylamino-8-chloro-6-fluoro-1,2,3,4-tetrahydro-9H-carbazol-9-yl)-acetic acid | C22H20N2O4ClF 430.862 | 1.01 LC-3 | 431.05 |
| 102 | (3RS)-(3-Benzyloxycarbonylamino-8-chloro-5-fluoro-1,2,3,4-tetrahydro-9H-carbazol-9-yl)-acetic acid | C22H20N2O4ClF 430.862 | 1.01 LC-3 | 431.04 |

Listed in Table 1a below are further compounds of Formula I, prepared according to the abovementioned general method with the corresponding compound of Structure 1 as starting material.

TABLE 1a

| Example | Compound of Formula I | Formula MW | $t_R$ [min] LCMS Method | MS Data m/z [M + H]+ |
|---|---|---|---|---|
| 103 | (3RS)-[3-(3-Benzyl-ureido)-6-fluoro-1,2,3,4-tetrahydro-9H-carbazol-9-yl]-acetic acid | C22H22N3O3F 395.433 | 0.92 LC-3 | 396.17 |
| 104 | (3S)-[6-Fluoro-3-(3-phenethyl-ureido)-1,2,3,4-tetrahydro-9H-carbazol-9-yl]-acetic acid | C23H24N3O3F 409.46 | 0.92 LC-3 | 410.52 |
| 105 | (3RS)-[3-(3-Benzyl-ureido)-8-chloro-6-fluoro-1,2,3,4-tetrahydro-9H-carbazol-9-yl]-acetic acid | C22H21N3O3ClF 429.878 | 0.95 LC-3 | 430.07 |
| 106 | (3RS)-[8-Chloro-6-fluoro-3-(3-phenethyl-ureido)-1,2,3,4-tetrahydro-9H-carbazol-9-yl]-acetic acid | C23H23N3O3ClF 443.905 | 0.97 LC-3 | 444.07 |
| 107 | (3RS)-(3-Benzyloxycarbonylamino-6-trifluoromethyl-1,2,3,4-tetrahydro-9H-carbazol-9-yl)-acetic acid | C23H21N2O4F3 446.424 | 1.02 LC-3 | 447.25 |

TABLE 1a-continued

| Example | Compound of Formula I | Formula MW | $t_R$ [min] LCMS Method | MS Data m/z [M + H]+ |
|---|---|---|---|---|
| 108 | (3RS)-(3-Benzyloxycarbonylamino-8-bromo-6-fluoro-1,2,3,4-tetrahydro-9H-carbazol-9-yl)-acetic acid | C22H20N2O4BrF 475.313 | 1.02 LC-3 | 474.98 |
| 109 | (3RS)-(3-Benzyloxycarbonylamino-6-fluoro-8-vinyl-1,2,3,4-tetrahydro-9H-carbazol-9-yl)-acetic acid | C24H23N2O4F 422.455 | 1.01 LC-3 | 423.15 |
| 110 | (3RS)-(3-Benzyloxycarbonylamino-6-fluoro-8-methanesulfonyl-1,2,3,4-tetrahydro-9H-carbazol-9-yl)-acetic acid | C23H23N2O6FS 474.508 | 0.95 LC-3 | 475.15 |
| 111 | (3S)-(3-Benzyloxycarbonylamino-6-fluoro-8-methyl-1,2,3,4-tetrahydro-9H-carbazol-9-yl)-acetic acid | C23H23N2O4F 410.444 | 0.99 LC-3 | 411.14 |
| 112 | (3S)-(3-Benzyloxycarbonylamino-7-chloro-6-fluoro-1,2,3,4-tetrahydro-9H-carbazol-9-yl)-acetic acid | C22H20N2O4ClF 430.862 | 1.01 LC-3 | 431.16 |
| 113 | (3S)-(8-Allyl-3-benzyloxycarbonylamino-6-fluoro-1,2,3,4-tetrahydro-9H-carbazol-9-yl)-acetic acid | C25H25N2O4F 436.482 | 1.02 LC-3 | 437.1 |
| 114 | (3R)-(3-Benzyloxycarbonylamino-8-chloro-1,2,3,4-tetrahydro-9H-carbazol-9-yl)-acetic acid | C22H21N2O4Cl 412.872 | 1 LC-3 | 413.03 |
| 115 | (3S)-{3-[3-(2,4-Dimethoxy-phenyl)-propionylamino]-6-fluoro-1,2,3,4-tetrahydro-9H-carbazol-9-yl}-acetic acid | C25H27N2O5F 454.496 | 0.95 LC-3 | 455.11 |
| 116 | (3S)-[6-Fluoro-3-(3-naphthalen-1-yl-propionylamino)-1,2,3,4-tetrahydro-9H-carbazol-9-yl]-acetic acid | C27H25N2O3F 444.505 | 0.99 LC-3 | 445.14 |
| 117 | (3RS)-{6-Fluoro-3-[2-(2-methoxy-phenoxy)-acetylamino]-1,2,3,4-tetrahydro-9H-carbazol-9-yl}-acetic acid | C23H23N2O5F 426.443 | 0.94 LC-3 | 427.16 |
| 118 | (3RS)-{6-Fluoro-3-[3-(2-methylphenyl)-propionylamino]-1,2,3,4-tetrahydro-9H-carbazol-9-yl}-acetic acid | C24H25N2O3F 408.472 | 0.97 LC-3 | 409.08 |
| 119 | (3RS)-{6-Fluoro-3-[3-(3-methylphenyl)-propionylamino]-1,2,3,4-tetrahydro-9H-carbazol-9-yl}-acetic acid | C24H25N2O3F 408.472 | 0.97 LC-3 | 409.11 |
| 120 | (3RS)-{6-Fluoro-3-[3-(3-methoxy-phenyl)-propionylamino]-1,2,3,4-tetrahydro-9H-carbazol-9-yl}-acetic acid | C24H25N2O4F 424.471 | 0.94 LC-3 | 425.1 |
| 121 | (3RS)-{6-Fluoro-3-[2-(3-methoxy-phenoxy)-acetylamino]-1,2,3,4-tetrahydro-9H-carbazol-9-yl}-acetic acid | C23H23N2O5F 426.443 | 0.95 LC-3 | 427.12 |
| 122 | (3RS)-{6-Fluoro-3-[2-(2-methylphenoxy)-acetylamino]-1,2,3,4-tetrahydro-9H-carbazol-9-yl}-acetic acid | C23H23N2O4F 410.444 | 0.98 LC-3 | 411 |
| 123 | (3S)-{3-[3-(2,5-Dimethoxy-phenyl)-propionylamino]-6-fluoro-1,2,3,4-tetrahydro-9H-carbazol-9-yl}-acetic acid | C25H27N2O5F 454.496 | 0.94 LC-3 | 455.19 |
| 124 | (3S)-{6-Fluoro-3-[3-(4-trifluoromethyl-phenyl)-propionylamino]-1,2,3,4-tetrahydro-9H-carbazol-9-yl}-acetic acid | C24H22N2O3F4 462.442 | 0.99 LC-3 | 463.15 |
| 125 | (3S)-{3-[3-(2,6-Dichloro-phenyl)-propionylamino]-6-fluoro-1,2,3,4-tetrahydro-9H-carbazol-9-yl}-acetic acid | C23H21N2O3Cl2F 463.335 | 0.99 LC-3 | 463.07 |
| 126 | (3S)-{3-[3-(2,5-Bis-trifluoromethyl-phenyl)-propionylamino]-6-fluoro-1,2,3,4-tetrahydro-9H-carbazol-9-yl}-acetic acid | C25H21N2O3F7 530.439 | 1.04 LC-3 | 530.97 |
| 127 | (3S)-{6-Fluoro-3-[3-(4-methylsulfanyl-phenyl)-propionylamino]-1,2,3,4-tetrahydro-9H-carbazol-9-yl}-acetic acid | C24H25N2O3FS 440.538 | 0.97 LC-3 | 441.1 |

TABLE 1a-continued

| Example | Compound of Formula I | Formula MW | $t_R$ [min] LCMS Method | MS Data m/z [M + H]+ |
|---|---|---|---|---|
| 128 | (3S)-{6-Fluoro-3-[3-(4-iodo-phenyl)-propionylamino]-1,2,3,4-tetrahydro-9H-carbazol-9-yl}-acetic acid | C23H22N2O3FI 520.337 | 0.99 LC-3 | 521.03 |
| 129 | (3S)-{6-Fluoro-3-[3-(4-isopropyl-phenyl)-propionylamino]-1,2,3,4-tetrahydro-9H-carbazol-9-yl}-acetic acid | C26H29N2O3F 436.525 | 1.01 LC-3 | 437.17 |
| 130 | (3S)-{6-Fluoro-3-[3-(3-trifluoromethyl-phenyl)-propionylamino]-1,2,3,4-tetrahydro-9H-carbazol-9-yl}-acetic acid | C24H22N2O3F4 462.442 | 0.99 LC-3 | 463.13 |
| 131 | (3S)-{3-[3-(2,4-Dichloro-phenyl)-propionylamino]-6-fluoro-1,2,3,4-tetrahydro-9H-carbazol-9-yl}-acetic acid | C23H21N2O3Cl2F 463.335 | 1.01 LC-3 | 463.08 |
| 132 | (3S)-{6-Fluoro-3-[3-(4-fluoro-phenyl)-propionylamino]-1,2,3,4-tetrahydro-9H-carbazol-9-yl}-acetic acid | C23H22N2O3F2 412.435 | 0.95 LC-3 | 413.08 |
| 133 | (3S)-{3-[3-(3,5-Bis-trifluoromethyl-phenyl)-propionylamino]-6-fluoro-1,2,3,4-tetrahydro-9H-carbazol-9-yl}-acetic acid | C25H21N2O3F7 530.439 | 1.03 LC-3 | 530.99 |
| 134 | (3S)-{3-[3-(4-Ethyl-phenyl)-propionylamino]-6-fluoro-1,2,3,4-tetrahydro-9H-carbazol-9-yl}-acetic acid | C25H27N2O3F 422.498 | 0.99 LC-3 | 423.12 |
| 135 | (3S)-{6-Fluoro-3-[3-(3-iodo-phenyl)-propionylamino]-1,2,3,4-tetrahydro-9H-carbazol-9-yl}-acetic acid | C23H22N2O3FI 520.337 | 0.97 LC-3 | 521.41 |
| 136 | (3S)-{6-Fluoro-3-[3-(4-methanesulfonyl-phenyl)-propionylamino]-1,2,3,4-tetrahydro-9H-carbazol-9-yl}-acetic acid | C24H25N2O5FS 472.536 | 0.87 LC-3 | 473.12 |
| 137 | (3S)-{3-[3-(2,3-Dimethoxy-phenyl)-propionylamino]-6-fluoro-1,2,3,4-tetrahydro-9H-carbazol-9-yl}-acetic acid | C25H27N2O5F 454.496 | 0.94 LC-3 | 455.16 |
| 138 | (3S)-{3-[3-(2-Bromo-phenyl)-propionylamino]-6-fluoro-1,2,3,4-tetrahydro-9H-carbazol-9-yl}-acetic acid | C23H22N2O3BrF 473.341 | 0.98 LC-3 | 474.97 |
| 139 | (3S)-{6-Fluoro-3-[3-(3-trifluoromethoxy-phenyl)-propionylamino]-1,2,3,4-tetrahydro-9H-carbazol-9-yl}-acetic acid | C24H22N2O4F4 478.441 | 1 LC-3 | 479.11 |
| 140 | (3S)-{3-[3-(2,4-Dimethyl-phenyl)-propionylamino]-6-fluoro-1,2,3,4-tetrahydro-9H-carbazol-9-yl}-acetic acid | C25H27N2O3F 422.498 | 0.99 LC-3 | 423.14 |
| 141 | (3S)-{3-[3-(3-Bromo-phenyl)-propionylamino]-6-fluoro-1,2,3,4-tetrahydro-9H-carbazol-9-yl}-acetic acid | C23H22N2O3BrF 473.341 | 0.98 LC-3 | 474.93 |
| 142 | (3S)-{3-[3-(3-tert-Butoxycarbonylamino-phenyl)-propionylamino]-6-fluoro-1,2,3,4-tetrahydro-9H-carbazol-9-yl}-acetic acid | C28H32N3O5F 509.576 | 0.98 LC-3 | 510.17 |
| 143 | (3S)-{6-Fluoro-3-[(S)-3-(4-fluoro-phenyl)-2-phenyl-propionylamino]-1,2,3,4-tetrahydro-9H-carbazol-9-yl}-acetic acid | C29H26N2O3F2 488.532 | 1.02 LC-3 | 489.15 |
| 144 | (3S)-{6-Fluoro-3-[(S)-3-(4-methoxy-phenyl)-2-phenyl-propionylamino]-1,2,3,4-tetrahydro-9H-carbazol-9-yl}-acetic acid | C30H29N2O4F 500.568 | 1.01 LC-3 | 501.16 |
| 145 | (3S)-{6-Fluoro-3-[3-(2-fluoro-phenyl)-propionylamino]-1,2,3,4-tetrahydro-9H-carbazol-9-yl}-acetic acid | C23H22N2O3F2 412.435 | 0.95 LC-3 | 413.09 |
| 146 | (3S)-(6-Fluoro-3-{[(2RS)-1,2,3,4-tetrahydro-naphthalene-2-carbonyl]-amino}-1,2,3,4-tetrahydro-9H-carbazol-9-yl)-acetic acid | C25H25N2O3F 420.483 | 0.98 LC-3 | 421.11 |

TABLE 1a-continued

| Example | Compound of Formula I | Formula MW | $t_R$ [min] LCMS Method | MS Data m/z $[M + H]^+$ |
|---|---|---|---|---|
| 147 | (3S)-(6-Fluoro-3-{[(2RS)-8-methoxy-1,2,3,4-tetrahydro-naphthalene-2-carbonyl]-amino}-1,2,3,4-tetrahydro-9H-carbazol-9-yl)-acetic acid | C26H27N2O4F 450.508 | 0.98 LC-3 | 451.08 |
| 148 | (3S)-(6-Fluoro-3-{(2RS)-2-[(4-fluoro-phenylcarbamoyl)-methyl]-3-phenyl-propionylamino}-1,2,3,4-tetrahydro-9H-carbazol-9-yl)-acetic acid | C31H29N3O4F2 545.584 | 0.98 LC-3 | 546.06 |
| 149 | (3S)-{3-[(2RS)-2-Benzyl-3,3-dimethyl-butyrylamino]-6-fluoro-1,2,3,4-tetrahydro-9H-carbazol-9-yl}-acetic acid | C27H31N2O3F 450.552 | 1.02 LC-3 | 451.12 |
| 150 | (3S)-(6-Fluoro-3-{[(2RS)-8-methoxy-1,2,3,4-tetrahydro-naphthalene-2-carbonyl]-amino}-1,2,3,4-tetrahydro-9H-carbazol-9-yl)-acetic acid | C24H23N2O4F 422.455 | 0.95 LC-3 | 423.11 |
| 151 | (3S)-{6-Fluoro-3-[3-(3-fluoro-phenyl)-propionylamino]-1,2,3,4-tetrahydro-9H-carbazol-9-yl}-acetic acid | C23H22N2O3F2 412.435 | 0.94 LC-3 | 413.08 |
| 152 | (3S)-(6-Fluoro-3-{[(2RS)-8-methoxy-1,2,3,4-tetrahydro-naphthalene-2-carbonyl]-amino}-1,2,3,4-tetrahydro-9H-carbazol-9-yl)-acetic acid | C24H23N2O3F 406.456 | 0.96 LC-3 | 407.1 |
| 153 | (3S)-{6-Fluoro-3-[(2R)-2-methyl-3-phenyl-propionylamino]-1,2,3,4-tetrahydro-9H-carbazol-9-yl}-acetic acid | C24H25N2O3F 408.472 | 0.95 LC-3 | 409.11 |
| 154 | (3S)-[3-(2,2-Dimethyl-3-phenyl-propionylamino)-6-fluoro-1,2,3,4-tetrahydro-9H-carbazol-9-yl]-acetic acid | C25H27N2O3F 422.498 | 0.99 LC-3 | 423.19 |
| 155 | (3S)-[6-Fluoro-3-(3-methyl-3-phenyl-butyrylamino)-1,2,3,4-tetrahydro-9H-carbazol-9-yl]-acetic acid | C25H27N2O3F 422.498 | 1 LC-3 | 423.2 |
| 156 | (3S)-{6-Fluoro-3-[(3S)-3-phenyl-butyrylamino]-1,2,3,4-tetrahydro-9H-carbazol-9-yl}-acetic acid | C24H25N2O3F 408.472 | 0.95 LC-3 | 409.2 |
| 157 | (3S)-[3-(2-Benzyloxy-acetylamino)-6-fluoro-1,2,3,4-tetrahydro-9H-carbazol-9-yl]-acetic acid | C23H23N2O4F 410.444 | 0.94 LC-3 | 411.06 |
| 158 | (3S)-[6-Fluoro-3-(4-phenyl-butyrylamino)-1,2,3,4-tetrahydro-9H-carbazol-9-yl]-acetic acid | C24H25N2O3F 408.472 | 0.96 LC-3 | 409.16 |
| 159 | (3S)-{3-[(2R,3R)-2,3-Dihydroxy-3-(2-methoxy-phenylcarbamoyl)-propionylamino]-6-fluoro-1,2,3,4-tetrahydro-9H-carbazol-9-yl}-acetic acid | C25H26N3O7F 499.493 | 0.86 LC-3 | 500.19 |
| 160 | (3RS)-{8-Chloro-6-fluoro-3-[3-(2-methylphenyl)-propionylamino]-1,2,3,4-tetrahydro-9H-carbazol-9-yl}-acetic acid | C24H24N2O3ClF 442.917 | 1 LC-3 | 443.11 |
| 161 | (3RS)-{8-Chloro-6-fluoro-3-[2-(2-methoxy-phenoxy)-acetylamino]-1,2,3,4-tetrahydro-9H-carbazol-9-yl}-acetic acid | C23H22N2O5ClF 460.888 | 0.98 LC-3 | 461.18 |
| 162 | (3RS)-{8-Chloro-6-fluoro-3-[3-(3-hydroxy-phenyl)-propionylamino]-1,2,3,4-tetrahydro-9H-carbazol-9-yl}-acetic acid | C23H22N2O4ClF 444.889 | 0.88 LC-3 | 445.32 |
| 163 | (3RS)-{8-Chloro-6-fluoro-3-[3-(3-methoxy-phenyl)-propionylamino]-1,2,3,4-tetrahydro-9H-carbazol-9-yl}-acetic acid | C24H24N2O4ClF 458.916 | 0.98 LC-3 | 459.04 |
| 164 | (3RS)-{8-Chloro-6-fluoro-3-[3-(3-methylphenyl)-propionylamino]-1,2,3,4-tetrahydro-9H-carbazol-9-yl}-acetic acid | C24H24N2O3ClF 442.917 | 1.01 LC-3 | 443.01 |
| 165 | (3RS)-{8-Chloro-6-fluoro-3-[3-(2-hydroxy-phenyl)-propionylamino]-1,2,3,4-tetrahydro-9H-carbazol-9-yl}-acetic acid | C23H22N2O4ClF 444.889 | 0.92 LC-3 | 486.38 |
| 166 | (3RS)-[8-Chloro-6-fluoro-3-(3-phenyl-propionylamino)-1,2,3,4-tetrahydro-9H-carbazol-9-yl]-acetic acid | C23H22N2O3ClF 428.89 | 0.98 LC-3 | 429.13 |

TABLE 1a-continued

| Example | Compound of Formula I | Formula MW | $t_R$ [min] LCMS Method | MS Data m/z [M + H]+ |
|---|---|---|---|---|
| 167 | (3RS)-{8-Chloro-6-fluoro-3-[3-(2-methoxy-phenyl)-propionylamino]-1,2,3,4-tetrahydro-9H-carbazol-9-yl}-acetic acid | C24H24N2O4ClF 458.916 | 0.99 LC-3 | 459.03 |
| 168 | (3RS)-{8-Chloro-3-[3-(3-chloro-phenyl)-propionylamino]-6-fluoro-1,2,3,4-tetrahydro-9H-carbazol-9-yl}-acetic acid | C23H21N2O3Cl2F 463.335 | 1.01 LC-3 | 463.11 |
| 169 | (3RS)-[8-Chloro-6-fluoro-3-(3-1H-indol-3-yl-propionylamino)-1,2,3,4-tetrahydro-9H-carbazol-9-yl]-acetic acid | C25H23N3O3ClF 467.927 | 0.97 LC-3 | 468.11 |
| 170 | (3RS)-{8-Chloro-3-[2-(2-chloro-phenoxy)-acetylamino]-6-fluoro-1,2,3,4-tetrahydro-9H-carbazol-9-yl}-acetic acid | C22H19N2O4Cl2F 465.307 | 1.01 LC-3 | 465.09 |
| 171 | (3RS)-{8-Chloro-6-fluoro-3-[2-(2-methylphenyl)-oxy-acetylamino]-1,2,3,4-tetrahydro-9H-carbazol-9-yl}-acetic acid | C23H22N2O4ClF 444.889 | 1.02 LC-3 | 445.11 |
| 172 | (3RS)-[3-(3-Benzo[1,3]dioxol-5-yl-propionylamino)-8-chloro-6-fluoro-1,2,3,4-tetrahydro-9H-carbazol-9-yl]-acetic acid | C24H22N2O5ClF 472.899 | 0.93 LC-3 | 473.17 |
| 173 | (3RS)-{8-Chloro-6-fluoro-3-[2-(3-methoxy-phenoxy)-acetylamino]-1,2,3,4-tetrahydro-9H-carbazol-9-yl}-acetic acid | C23H22N2O5ClF 460.888 | 0.99 LC-3 | 461.09 |
| 174 | (3RS)-{8-Chloro-3-[2-(3-chloro-phenoxy)-acetylamino]-6-fluoro-1,2,3,4-tetrahydro-9H-carbazol-9-yl}-acetic acid | C22H19N2O4Cl2F 465.307 | 1.02 LC-3 | 465 |
| 175 | (3RS)-{8-Chloro-3-[3-(2-chloro-phenyl)-propionylamino]-6-fluoro-1,2,3,4-tetrahydro-9H-carbazol-9-yl}-acetic acid | C23H21N2O3Cl2F 463.335 | 1.01 LC-3 | 463.07 |
| 176 | (3RS)-[8-Chloro-6-fluoro-3-(2-indan-2-yl-acetylamino)-1,2,3,4-tetrahydro-9H-carbazol-9-yl]-acetic acid | C25H24N2O3ClF 454.928 | 1.01 LC-3 | 455.16 |
| 177 | (3S)-[6-Fluoro-3-(1-methyl-3-phenethyl-ureido)-1,2,3,4-tetrahydro-9H-carbazol-9-yl]-acetic acid | C24H26N3O3F 423.486 | 0.98 LC-3 | 429.13 |
| 178 | (3S)-{3-[3-(2-Chloro-benzyl)-1-methyl-ureido]-6-fluoro-1,2,3,4-tetrahydro-9H-carbazol-9-yl}-acetic acid | C23H23N3O3ClF 443.905 | 0.97 LC-3 | 444.16 |
| 179 | (3S)-[3-(3-Benzyl-1-methyl-ureido)-6-fluoro-1,2,3,4-tetrahydro-9H-carbazol-9-yl]-acetic acid | C23H24N3O3F 409.46 | 0.94 LC-3 | 410.12 |
| 180 | (3S)-[3-(Benzyloxycarbonyl-methyl-amino)-6-fluoro-1,2,3,4-tetrahydro-9H-carbazol-9-yl]-acetic acid | C23H23N2O4F 410.444 | 1.01 LC-3 | 411.07 |
| 181 | {(3S)-3-[(2-Chloro-benzyloxycarbonyl)-methyl-amino]-6-fluoro-1,2,3,4-tetrahydro-9H-carbazol-9-yl}-acetic acid | C23H22N2O4ClF 444.889 | 1.03 LC-3 | 445.15 |
| 182 | (3S)-(6-Fluoro-3-{[2-(4-methoxy-phenyl)-acetyl]-methyl-amino}-1,2,3,4-tetrahydro-9H-carbazol-9-yl)-acetic acid | C24H25N2O4F 424.471 | 0.95 LC-3 | 425.19 |
| 183 | (3S)-(6-Fluoro-3-{methyl-[2-(4-methylphenyl)-acetyl]-amino}-1,2,3,4-tetrahydro-9H-carbazol-9-yl)-acetic acid | C24H25N2O3F 408.472 | 0.98 LC-3 | 409.18 |
| 184 | (3S)-(6-Fluoro-3-{[2-(2-methoxy-phenyl)-acetyl]-methyl-amino}-1,2,3,4-tetrahydro-9H-carbazol-9-yl)-acetic acid | C24H25N2O4F 424.471 | 0.96 LC-3 | 425.18 |
| 185 | (3S)-{6-Fluoro-3-[(2-indan-2-yl-acetyl)-methyl-amino]-1,2,3,4-tetrahydro-9H-carbazol-9-yl}-acetic acid | C26H27N2O3F 434.509 | 1.01 LC-3 | 435.16 |
| 186 | (3S)-(3-{[2-(3-Chloro-phenyl)-acetyl]-methyl-amino}-6-fluoro-1,2,3,4-tetrahydro-9H-carbazol-9-yl)-acetic acid | C23H22N2O3ClF 428.89 | 0.99 LC-3 | 429.13 |

TABLE 1a-continued

| Example | Compound of Formula I | Formula MW | $t_R$ [min] LCMS Method | MS Data m/z $[M + H]^+$ |
|---|---|---|---|---|
| 187 | (3S)-(6-Fluoro-3-{methyl-[2-(3-methylphenyl)-acetyl]-amino}-1,2,3,4-tetrahydro-9H-carbazol-9-yl)-acetic acid | C24H25N2O3F 408.472 | 0.98 LC-3 | 409.1 |
| 188 | (3S)-(6-Fluoro-3-{[2-(3-methoxy-phenyl)-acetyl]-methyl-amino}-1,2,3,4-tetrahydro-9H-carbazol-9-yl)-acetic acid | C24H25N2O4F 424.471 | 0.95 LC-3 | 425.08 |
| 189 | (3S)-(3-{[2-(2-Chloro-phenoxy)-acetyl]-methyl-amino}-6-fluoro-1,2,3,4-tetrahydro-9H-carbazol-9-yl)-acetic acid | C23H22N2O4ClF 444.889 | 0.97 LC-3 | 445.38 |
| 190 | (3S)-(3-{[2-(4-Chloro-phenoxy)-acetyl]-methyl-amino}-6-fluoro-1,2,3,4-tetrahydro-9H-carbazol-9-yl)-acetic acid | C23H22N2O4ClF 444.889 | 0.98 LC-3 | 445.39 |
| 191 | (3S)-(6-Fluoro-3-{[3-(3-methoxy-phenyl)-propionyl]-methyl-amino}-1,2,3,4-tetrahydro-9H-carbazol-9-yl)-acetic acid | C25H27N2O4F 438.497 | 0.96 LC-3 | 439.47 |
| 192 | (3S)-(6-Fluoro-3-{methyl-[2-(2-methylphenyl)-acetyl]-amino}-1,2,3,4-tetrahydro-9H-carbazol-9-yl)-acetic acid | C24H25N2O3F 408.472 | 0.96 LC-3 | 409.48 |
| 193 | (3S)-{3-[(3,3-Diphenyl-propionyl)-methyl-amino]-6-fluoro-1,2,3,4-tetrahydro-9H-carbazol-9-yl}-acetic acid | C30H29N2O3F 484.569 | 1.02 LC-3 | 485.52 |
| 194 | (3S)-(6-Fluoro-3-{[3-(2-methoxy-phenyl)-propionyl]-methyl-amino}-1,2,3,4-tetrahydro-9H-carbazol-9-yl)-acetic acid | C25H27N2O4F 438.497 | 0.97 LC-3 | 439.45 |
| 195 | (3S)-{6-Fluoro-3-[(3-1H-indol-3-yl-propionyl)-methyl-amino]-1,2,3,4-tetrahydro-9H-carbazol-9-yl}-acetic acid | C26H26N3O3F 447.508 | 0.94 LC-3 | 448.44 |
| 196 | (3S)-{3-[(2-Benzyloxy-acetyl)-methyl-amino]-6-fluoro-1,2,3,4-tetrahydro-9H-carbazol-9-yl}-acetic acid | C24H25N2O4F 424.471 | 0.94 LC-3 | 425.44 |
| 197 | (3S)-{3-[(2,3-Diphenyl-propionyl)-methyl-amino]-6-fluoro-1,2,3,4-tetrahydro-9H-carbazol-9-yl}-acetic acid | C30H29N2O3F 484.569 | 1.04 LC-3 | 485.53 |
| 198 | (3S)-{6-Fluoro-3-[[3-(2-methoxy-phenyl)-propionyl]-(3-phenyl-propyl)-amino]-1,2,3,4-tetrahydro-9H-carbazol-9-yl}-acetic acid | C33H35N2O4F 542.649 | 1.07 LC-3 | 543.18 |
| 199 | (3S)-{3-[Acetyl-(3-phenyl-propyl)-amino]-6-fluoro-1,2,3,4-tetrahydro-9H-carbazol-9-yl}-acetic acid | C25H27N2O3F 422.498 | 1.01 LC-3 | 423.14 |
| 200 | (3S)-{3-[3-Benzyl-(1-cyclopropylmethyl)-ureido]-6-fluoro-1,2,3,4-tetrahydro-9H-carbazol-9-yl}-acetic acid | C26H28N3O3F 449.524 | 0.99 LC-3 | 450.2 |
| 201 | (3S)-[3-(Benzyloxycarbonyl-cyclopropylmethyl-amino)-6-fluoro-1,2,3,4-tetrahydro-9H-carbazol-9-yl]-acetic acid | C26H27N2O4F 450.508 | 1.05 LC-3 | 451.15 |
| 202 | (3S)-{3-[Cyclopropylmethyl-(3-phenyl-propionyl)-amino]-6-fluoro-1,2,3,4-tetrahydro-9H-carbazol-9-yl}-acetic acid | C27H29N2O3F 448.536 | 1.02 LC-3 | 449.25 |
| 203 | (3S)-{3-[Cyclopropylmethyl-((S)-2-methyl-3-phenyl-propionyl)-amino]-6-fluoro-1,2,3,4-tetrahydro-9H-carbazol-9-yl}-acetic acid | C28H31N2O3F 462.563 | 1.03 LC-3 | 463.27 |
| 204 | (3S)-(3-{Cyclopropylmethyl-[3-(2-methoxy-phenyl)-propionyl]-amino}-6-fluoro-1,2,3,4-tetrahydro-9H-carbazol-9-yl)-acetic acid | C28H31N2O4F 478.562 | 1.02 LC-3 | 479.28 |
| 205 | (3S)-(3-{[2-(3-Chloro-phenoxy)-acetyl]-cyclopropylmethyl-amino}-6-fluoro-1,2,3,4-tetrahydro-9H-carbazol-9-yl)-acetic acid | C26H26N2O4ClF 484.953 | 1.03 LC-3 | 485.2 |

TABLE 1a-continued

| Example | Compound of Formula I | Formula MW | $t_R$ [min] LCMS Method | MS Data m/z [M + H]+ |
|---|---|---|---|---|
| 206 | (3S)-{3-[Cyclopropylmethyl-(3,3-diphenyl-propionyl)-amino]-6-fluoro-1,2,3,4-tetrahydro-9H-carbazol-9-yl}-acetic acid | C33H33N2O3F 524.634 | 1.07 LC-3 | 525.26 |
| 207 | (3S)-{3-[Cyclopropylmethyl-(2-naphthalen-1-yl-acetyl)-amino]-6-fluoro-1,2,3,4-tetrahydro-9H-carbazol-9-yl}-acetic acid | C30H29N2O3F 484.569 | 1.04 LC-3 | 485.26 |
| 208 | (3S)-(3-{Benzyloxycarbonyl-[2-(4-trifluoromethyl-phenoxy)-ethyl]-amino}-6-fluoro-1,2,3,4-tetrahydro-9H-carbazol-9-yl)-acetic acid | C31H28N2O5F4 584.564 | 1.15 LC-3 | 585.14 |
| 209 | (3S)-(3-{Acetyl-[2-(4-trifluoromethyl-phenoxy)-ethyl]-amino}-6-fluoro-1,2,3,4-tetrahydro-9H-carbazol-9-yl)-acetic acid | C25H24N2O4F4 492.468 | 1.07 LC-3 | 493.17 |
| 210 | (3S)-(6-Fluoro-3-{propionyl-[2-(4-trifluoromethyl-phenoxy)-ethyl]-amino}-1,2,3,4-tetrahydro-9H-carbazol-9-yl)-acetic acid | C26H26N2O4F4 506.494 | 1.08 LC-3 | 507.18 |
| 211 | (3S)-(6-Fluoro-3-{(3-phenyl-propionyl)-[2-(4-trifluoromethyl-phenoxy)-ethyl]-amino}-1,2,3,4-tetrahydro-9H-carbazol-9-yl)-acetic acid | C32H30N2O4F4 582.592 | 1.13 LC-3 | 583.14 |
| 212 | (3S)-(6-Fluoro-3-{[3-(2-methoxy-phenyl)-propionyl]-[2-(4-trifluoromethyl-phenoxy)-ethyl]-amino}-1,2,3,4-tetrahydro-9H-carbazol-9-yl)-acetic acid | C33H32N2O5F4 612.618 | 1.13 LC-3 | 613.26 |
| 213 | (3S)-{6-Fluoro-3-[(2-phenoxy-ethyl)-(3-phenyl-propionyl)-amino]-1,2,3,4-tetrahydro-9H-carbazol-9-yl}-acetic acid | C31H31N2O4F 514.595 | 1.06 LC-3 | 515.17 |
| 214 | (3S)-{6-Fluoro-3-[((S)-2-methyl-3-phenyl-propionyl)-(2-phenoxy-ethyl)-amino]-1,2,3,4-tetrahydro-9H-carbazol-9-yl}-acetic acid | C32H33N2O4F 528.622 | 1.07 LC-3 | 529.26 |
| 215 | (3S)-{6-Fluoro-3-[[3-(2-methoxy-phenyl)-propionyl]-(2-phenoxy-ethyl)-amino]-1,2,3,4-tetrahydro-9H-carbazol-9-yl}-acetic acid | C32H33N2O5F 544.621 | 1.06 LC-3 | 545.25 |
| 216 | (3S)-{3-[Acetyl-(2-phenoxy-ethyl)-amino]-6-fluoro-1,2,3,4-tetrahydro-9H-carbazol-9-yl}-acetic acid | C24H25N2O4F 424.471 | 0.98 LC-3 | 425.19 |
| 217 | (3S)-{3-[3-Benzyl-1-(2-methoxy-ethyl)-ureido]-6-fluoro-1,2,3,4-tetrahydro-9H-carbazol-9-yl}-acetic acid | C25H28N3O4F 453.512 | 0.97 LC-3 | 454.26 |
| 218 | (3S)-{3-[Benzyloxycarbonyl-(2-methoxy-ethyl)-amino]-6-fluoro-1,2,3,4-tetrahydro-9H-carbazol-9-yl}-acetic acid | C25H27N2O5F 454.496 | 0.97 LC-3 | 454.26 |
| 219 | (3S)-{6-Fluoro-3-[(2-methoxy-ethyl)-(3-phenyl-propionyl)-amino]-1,2,3,4-tetrahydro-9H-carbazol-9-yl}-acetic acid | C26H29N2O4F 452.524 | 0.98 LC-3 | 453.25 |
| 220 | (3S)-{6-Fluoro-3-[(2-methoxy-ethyl)-((S)-2-methyl-3-phenyl-propionyl)-amino]-1,2,3,4-tetrahydro-9H-carbazol-9-yl}-acetic acid | C27H31N2O4F 466.551 | 1 LC-3 | 467.18 |
| 221 | (3S)-(6-Fluoro-3-{(2-methoxy-ethyl)-[3-(2-methoxy-phenyl)-propionyl]-amino}-1,2,3,4-tetrahydro-9H-carbazol-9-yl)-acetic acid | C27H31N2O5F 482.55 | 0.98 LC-3 | 483.19 |
| 222 | (3S)-{3-[[2-(3-Chloro-phenoxy)-acetyl]-(2-methoxy-ethyl)-amino]-6-fluoro-1,2,3,4-tetrahydro-9H-carbazol-9-yl}-acetic acid | C25H26N2O5ClF 488.941 | 1 LC-3 | 489.17 |
| 223 | (3S)-{3-[(3,3-Diphenyl-propionyl)-(2-methoxy-ethyl)-amino]-6-fluoro-1,2,3,4-tetrahydro-9H-carbazol-9-yl}-acetic acid | C32H33N2O4F 528.622 | 1.04 LC-3 | 529.28 |

TABLE 1a-continued

| Example | Compound of Formula I | Formula MW | $t_R$ [min] LCMS Method | MS Data m/z $[M + H]^+$ |
|---|---|---|---|---|
| 224 | (3S)-{6-Fluoro-3-[(2-methoxy-ethyl)-(2-naphthalen-1-yl-acetyl)-amino]-1,2,3,4-tetrahydro-9H-carbazol-9-yl}-acetic acid | C29H29N2O4F 488.557 | 1.01 LC-3 | 489.24 |
| 225 | (3S)-(6-Fluoro-3-{[(2S)-2-methyl-3-phenyl-propionyl]-phenethyl-amino}-1,2,3,4-tetrahydro-9H-carbazol-9-yl)-acetic acid | C32H33N2O3F 512.623 | 1.07 LC-3 | 513.27 |
| 226 | (3S)-(6-Fluoro-3-{[3-(2-methoxy-phenyl)-propionyl]-phenethyl-amino}-1,2,3,4-tetrahydro-9H-carbazol-9-yl)-acetic acid | C32H33N2O4F 528.622 | 1.06 LC-3 | 529.27 |
| 227 | (3S)-[3-(Acetyl-phenethyl-amino)-6-fluoro-1,2,3,4-tetrahydro-9H-carbazol-9-yl]-acetic acid | C24H25N2O3F 408.472 | 0.98 LC-3 | 409.16 |
| 228 | (3S)-{6-Fluoro-3-[(2-naphthalen-1-yl-acetyl)-phenethyl-amino]-1,2,3,4-tetrahydro-9H-carbazol-9-yl}-acetic acid | C34H31N2O3F 534.629 | 1.08 LC-3 | 535.27 |
| 229 | (3S)-{6-Fluoro-3-[phenethyl-(3-phenyl-propionyl)-amino]-1,2,3,4-tetrahydro-9H-carbazol-9-yl}-acetic acid | C31H31N2O3F 498.596 | 1.06 LC-3 | 499.2 |
| 230 | (3S)-[3-(3-Benzyl-1-naphthalen-1-ylmethyl-ureido)-6-fluoro-1,2,3,4-tetrahydro-9H-carbazol-9-yl]-acetic acid | C33H30N3O3F 535.617 | 1.05 LC-3 | 536.25 |
| 231 | (3S)-[3-(Benzyloxycarbonyl-naphthalen-1-ylmethyl-amino)-6-fluoro-1,2,3,4-tetrahydro-9H-carbazol-9-yl]-acetic acid | C33H29N2O4F 536.601 | 1.09 LC-3 | 537.24 |
| 232 | (3S)-{6-Fluoro-3-[naphthalen-1-ylmethyl-(3-phenyl-propionyl)-amino]-1,2,3,4-tetrahydro-9H-carbazol-9-yl}-acetic acid | C34H31N2O3F 534.629 | 1.07 LC-3 | 535.25 |
| 233 | (3S)-{6-Fluoro-3-[((S)-2-methyl-3-phenyl-propionyl)-naphthalen-1-ylmethyl-amino]-1,2,3,4-tetrahydro-9H-carbazol-9-yl}-acetic acid | C35H33N2O3F 548.656 | 1.09 LC-3 | 549.26 |
| 234 | (3S)-(6-Fluoro-3-{[3-(2-methoxy-phenyl)-propionyl]-naphthalen-1-ylmethyl-amino}-1,2,3,4-tetrahydro-9H-carbazol-9-yl)-acetic acid | C35H33N2O4F 564.655 | 1.07 LC-3 | 565.26 |
| 235 | (3S)-{3-[(3,3-Diphenyl-propionyl)-naphthalen-1-ylmethyl-amino]-6-fluoro-1,2,3,4-tetrahydro-9H-carbazol-9-yl}-acetic acid | C40H35N2O3F 610.727 | 1.11 LC-3 | 611.21 |
| 236 | (3S)-[3-(Acetyl-naphthalen-1-ylmethyl-amino)-6-fluoro-1,2,3,4-tetrahydro-9H-carbazol-9-yl]-acetic acid | C27H25N2O3F 444.505 | 1 LC-3 | 445.24 |
| 237 | (3S)-[6-Fluoro-3-(naphthalen-1-ylmethyl-propionyl-amino)-1,2,3,4-tetrahydro-9H-carbazol-9-yl]-acetic acid | C28H27N2O3F 458.531 | 1.01 LC-3 | 459.15 |
| 238 | (3S)-{3-[(RS)-2-Benzyl-3-(2-methylphenyl)-carbamoyl-propionylamino]-6-fluoro-1,2,3,4-tetrahydro-9H-carbazol-9-yl}-acetic acid | C32H32N3O4F 541.621 | 0.97 LC-3 | 542.22 |
| 239 | (3S)-{3-[(RS)-2-Benzyl-3-(3-methoxy-phenylcarbamoyl)-propionylamino]-6-fluoro-1,2,3,4-tetrahydro-9H-carbazol-9-yl}-acetic acid | C32H32N3O5F 557.620 | 0.97 LC-3 | 558.24 |
| 240 | (3S)-{3-[(RS)-2-Benzyl-3-(4-chloro-phenylcarbamoyl)-propionylamino]-6-fluoro-1,2,3,4-tetrahydro-9H-carbazol-9-yl}-acetic acid | C31H29N3O4ClF 562.039 | 1.01 LC-3 | 562.09 |
| 241 | (3S)-{3-[(RS)-2-Benzyl-3-(4-fluoro-benzylcarbamoyl)-propionylamino]-6-fluoro-1,2,3,4-tetrahydro-9H-carbazol-9-yl}-acetic acid | C32H31N3O4F2 559.611 | 0.96 LC-3 | 560.21 |

TABLE 1a-continued

| Example | Compound of Formula I | Formula MW | $t_R$ [min] LCMS Method | MS Data m/z [M + H]+ |
|---|---|---|---|---|
| 242 | [(3S)-3-((RS)-2-Benzyl-3-propylcarbamoyl-propionylamino)-6-fluoro-1,2,3,4-tetrahydro-9H-carbazol-9-yl]-acetic acid | C28H32N3O4F 493.577 | 0.91 LC-3 | 494.25 |
| 243 | (3S)-[6-Fluoro-3-(3-thiophen-2-yl-propionylamino)-1,2,3,4-tetrahydro-9H-carbazol-9-yl]-acetic acid | C21H21FN2O3S 400.47 | 0.93 LC-3 | 400.61 |
| 244 | (3S)-{3-[3-(3-Chloro-isoxazol-5-yl)-propionylamino]-6-fluoro-1,2,3,4-tetrahydro-9H-carbazol-9-yl}-acetic acid | C20H19ClFN3O4 419.83 | 0.91 LC-3 | 420.09 |
| 245 | (3S)-[6-Fluoro-3-(3-pyrimidin-2-yl-propionylamino)-1,2,3,4-tetrahydro-9H-carbazol-9-yl]-acetic acid | C21H21FN4O3 396.41 | 0.8 LC-3 | 397.11 |
| 246 | (3S)-{6-Fluoro-3-[3-phenyl-4-([1,3,4]thiadiazol-2-ylcarbamoyl)-butyrylamino]-1,2,3,4-tetrahydro-9H-carbazol-9-yl}-acetic acid | C27H26FN5O4S 535.59 | 0.87 LC-3 | 536.14 |
| 247 | (3S)-[3-(1,3-Dibenzyl-ureido)-6-fluoro-1,2,3,4-tetrahydro-9H-carbazol-9-yl]-acetic acid | C29H28FN3O3 485.55 | 1.02 LC.3 | 486.22 |
| 248 | (3S)-(3-{Acetyl-[2-(2-fluoro-phenyl)-ethyl]-amino}-6-fluoro-1,2,3,4-tetrahydro-9H-carbazol-9-yl)-acetic acid | C24H24F2N2O3 426.46 | 0.99 LC-3 | 427.07 |
| 249 | (3S)-(3-{Acetyl-[2-(3-fluoro-phenyl)-ethyl]-amino}-6-fluoro-1,2,3,4-tetrahydro-9H-carbazol-9-yl)-acetic acid | C24H24F2N2O3 426.46 | 0.99 LC-3 | 427.07 |
| 250 | (3S)-[3-(3-Benzyl-1-cyclohexylmethyl-ureido)-6-fluoro-1,2,3,4-tetrahydro-9H-carbazol-9-yl]-acetic acid | C29H34N3O3F 491.605 | 1.06 LC-3 | 492.26 |
| 251 | (3S)-(3-{Cyclohexylmethyl-[3-(2-methoxy-phenyl)-propionyl]-amino}-6-fluoro-1,2,3,4-tetrahydro-9H-carbazol-9-yl)-acetic acid | C31H37N2O4F 520.643 | 1.10 LC-3 | 521.25 |

Synthesis of Precursors and Intermediates

General Methods for the Synthesis of Intermediates of Structure 1

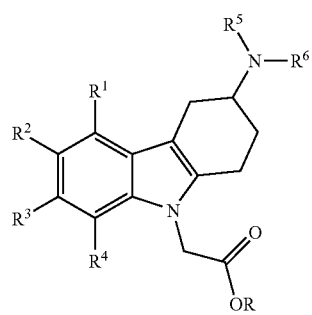

Structure 1, wherein R represents $C_{1-4}$-alkyl

1) N-Carbamoylation of an Intermediate of Structure 2a or 2b

The appropriate isocyanate (0.132 mmol) and a catalytical amount of DMAP are added to a 0° C. cold solution of a hydrochloride of the appropriate intermediate of Structure 2a or 2b (0.11 mmol) and Et$_3$N (0.034 ml, 0.242 mmol) in DCM (2 ml). The reaction mixture is stirred at rt overnight. Then, a 1:4 mixture (1 ml) of sat. NaHCO$_3$ solution and H$_2$O is added. After phase separation, the aq. layer is extracted three times with DCM. The combined org. phases are washed with 10% citric acid. The solvent is evaporated and the pure [3-ureido-1,2,3,4-tetrahydro-9H-carbazol-9-yl]-acetate derivative of Structure 1 is obtained by preparative HPLC with 8 to 98% yield.

Listed in Table 2 below are ethyl [3-ureido-1,2,3,4-tetrahydro-9H-carbazol-9-yl]-acetate derivatives of Structure 1, prepared according to the above mentioned method, with the corresponding compound of Structure 2a or 2b as starting material.

TABLE 2

| Intermediates of Structure 1: Ethyl [3-ureido-1,2,3,4-tetrahydro-9H-carbazol-9-yl]-acetate derivatives | Formula MW | $t_R$ [min] LC-MS Method | MS Data m/z [M + H]+ |
|---|---|---|---|
| Ethyl (3R)-[3-(3-butyl-ureido)-1,2,3,4-tetrahydro-9H-carbazol-9-yl]-acetate | C21H29N3O3 371.47 | 1.1 LC-2 | 372.05 |

TABLE 2-continued

| Intermediates of Structure 1: Ethyl [3-ureido-1,2,3,4-tetrahydro-9H-carbazol-9-yl]-acetate derivatives | Formula MW | $t_R$ [min] LC-MS Method | MS Data m/z [M + H]$^+$ |
|---|---|---|---|
| Ethyl (3R)-[3-(3-benzyl-ureido)-1,2,3,4-tetrahydro-9H-carbazol-9-yl]-acetate | C24H27N3O3 405.496 | 1.99 LC-1 | 406.06 |
| Ethyl (3R)-[3-(3-phenethyl-ureido)-1,2,3,4-tetrahydro-9H-carbazol-9-yl]-acetate | C25H29N3O3 419.523 | 2.15 LC-1 | 420.04 |
| Ethyl (3R)-[3-(3-naphthalen-1-yl-ureido)-1,2,3,4-tetrahydro-9H-carbazol-9-yl]-acetate | C27H27N3O3 441.52 | 1.19 LC-2 | 441.95 |
| Ethyl (3R)-[3-(3-phenylsulfonyl-ureido)-1,2,3,4-tetrahydro-9H-carbazol-9-yl]-acetate | C23H25N3O5S 455.534 | 1.96 LC-1 | 454.1 |
| Ethyl (3S)-[3-(3-butyl-ureido)-1,2,3,4-tetrahydro-9H-carbazol-9-yl]-acetate | C21H29N3O3 371.479 | 1.08 LC-2 | 372.16 |
| Ethyl (3S)-[3-(3-benzyl-ureido)-1,2,3,4-tetrahydro-9H-carbazol-9-yl]-acetate | C24H27N3O3 405.496 | 1.1 LC-2 | 406.16 |
| Ethyl (3S)-[3-(3-phenethyl-ureido)-1,2,3,4-tetrahydro-9H-carbazol-9-yl]-acetate | C25H29N3O3 419.523 | 1.12 LC-2 | 420.15 |
| Ethyl (3S)-[3-(3-phenylsulfonyl-ureido)-1,2,3,4-tetrahydro-9H-carbazol-9-yl]-acetate | C23H25N3O5S 455.534 | 1.09 LC-2 | 454.16 |
| Ethyl (3S)-[3-(3-phenyl-ureido)-1,2,3,4-tetrahydro-9H-carbazol-9-yl]-acetate | C23H25N3O3 391.47 | 1.11 LC-2 | 392.17 |

Listed in Table 2a below are further ethyl [3-ureido-1,2,3,4-tetrahydro-9H-carbazol-9-yl]-acetate derivatives of Structure 1, prepared according to the above mentioned method, with the corresponding compound of Structure 2a or 2b as starting material.

TABLE 2a

| Intermediates of Structure 1: Ethyl [3-ureido-1,2,3,4-tetrahydro-9H-carbazol-9-yl]-acetate derivatives | Formula MW |
|---|---|
| Ethyl (3RS)-[3-(3-benzyl-ureido)-6-fluoro-1,2,3,4-tetrahydro-9H-carbazol-9-yl]-acetate | C25H28FN3O3 437.51 |
| Ethyl (3S)-[6-fluoro-3-(3-phenethyl-ureido)-1,2,3,4-tetrahydro-9H-carbazol-9-yl]-acetate | C25H28N3O3F 437.51 |
| Ethyl (3RS)-[3-(3-benzyl-ureido)-8-chloro-6-fluoro-1,2,3,4-tetrahydro-9H-carbazol-9-yl]-acetate | C24H25ClFN3O3 457.93 |
| Ethyl (3RS)-[8-chloro-6-fluoro-3-(3-phenethyl-ureido)-1,2,3,4-tetrahydro-9H-carbazol-9-yl]-acetate | C25H27ClFN3O3 471.95 |
| Ethyl (3S)-[6-fluoro-3-(1-methyl-3-phenethyl-ureido)-1,2,3,4-tetrahydro-9H-carbazol-9-yl]-acetate | C26H30FN3O3 451.53 |
| Ethyl (3S)-{3-[3-(2-chloro-benzyl)-1-methyl-ureido]-6-fluoro-1,2,3,4-tetrahydro-9H-carbazol-9-yl}-acetate | C25H27ClFN3O3 471.95 |
| Ethyl (3S)-[3-(3-benzyl-1-methyl-ureido)-6-fluoro-1,2,3,4-tetrahydro-9H-carbazol-9-yl]-acetate | C25H28FN3O3 437.51 |
| Ethyl (3S)-{3-[3-benzyl-1-(1-cyclopropylmethyl)-ureido]-6-fluoro-1,2,3,4-tetrahydro-9H-carbazol-9-yl}-acetate | C28H32FN3O3 477.57 |
| Ethyl (3S)-{3-[3-benzyl-1-(2-methoxy-ethyl)-ureido]-6-fluoro-1,2,3,4-tetrahydro-9H-carbazol-9-yl}-acetate | C27H32FN3O4 481.56 |

TABLE 2a-continued

| Intermediates of Structure 1: Ethyl [3-ureido-1,2,3,4-tetrahydro-9H-carbazol-9-yl]-acetate derivatives | Formula MW |
|---|---|
| Ethyl (3S)-[3-(3-benzyl-1-cyclohexylmethyl-ureido)-6-fluoro-1,2,3,4-tetrahydro-9H-carbazol-9-yl]-acetate | C31H37N3O3F 519.655 |
| Ethyl (3S)-[3-(1,3-Dibenzyl-ureido)-6-fluoro-1,2,3,4-tetrahydro-9H-carbazol-9-yl]-acetate | C29H28FN3O3 513.60 |

2) Reaction of Intermediates of Structure 2a or 2b with Chloroformates

The appropriate chloroformate (neat) and a catalytical amount of DMAP is added to a 0° C. cold solution of a hydrochloride of the appropriate intermediate of Structure 2a or 2b (0.132 mmol) and Et$_3$N (0.034 ml, 0.242 mmol) in DCM (2 ml). The reaction mixture is stirred at rt overnight. Then, a 1:4 mixture (1 ml) of sat. NaHCO$_3$ solution and H$_2$O is added. After phase separation, the aq. layer is extracted three times with DCM. The combined org. phases are washed with 10% citric acid. The solvent is evaporated and the pure (3-oxycarbonylamino-1,2,3,4-tetrahydro-9H-carbazol-9-yl)-acetate derivative of Structure 1 is obtained by preparative HPLC with 5 to 96% yield.

Listed in Table 3 below are ethyl (3-oxycarbonylamino-1,2,3,4-tetrahydro-9H-carbazol-9-yl)-acetate derivatives of Structure 1, prepared according to the above mentioned method, with the corresponding compound of Structure 2a or 2b as starting material.

TABLE 3

| Intermediates of Structure 1: Ethyl (3-oxycarbonylamino-1,2,3,4-tetrahydro-9H-carbazol-9-yl)-acetate derivatives | Formula MW | $t_R$ [min] LC-MS Method | MS Data m/z |
|---|---|---|---|
| Ethyl (3R)-(3-propoxycarbonylamino-1,2,3,4-tetrahydro-9H-carbazol-9-yl)-acetate | C20H26N2O4 358.436 | 1.14 LC-2 | 380.98 [M + Na]$^+$ |
| Ethyl (3R)-(3-isobutoxycarbonylamino-1,2,3,4-tetrahydro-9H-carbazol-9-yl)-acetate | C21H28N2O4 372.463 | 1.20 LC-2 | 395.04 [M + Na]$^+$ |

TABLE 3-continued

| Intermediates of Structure 1:<br>Ethyl (3-oxycarbonylamino-1,2,3,4-tetrahydro-9H-carbazol-9-yl)-acetate derivatives | Formula MW | $t_R$ [min] LC-MS Method | MS Data m/z |
|---|---|---|---|
| Ethyl (3R)-(3-benzyloxycarbonylamino-1,2,3,4-tetrahydro-9H-carbazol-9-yl)-acetate | C24H26N2O4 406.48 | 1.17 LC-2 | 407.02 [M + H]+ |
| Ethyl (3R)-[3-(2-benzyloxy-ethoxycarbonylamino)-1,2,3,4-tetrahydro-9H-carbazol-9-yl]-acetate | C26H30N2O5 450.533 | 1.17 LC-2 | 473.01 [M + Na]+ |
| Ethyl (3S)-(3-propoxycarbonylamino-1,2,3,4-tetrahydro-9H-carbazol-9-yl)-acetate | C20H26N2O4 358.436 | 1.12 LC-2 | 381.09 [M + Na]+ |
| Ethyl (3S)-(3-isobutoxycarbonylamino-1,2,3,4-tetrahydro-9H-carbazol-9-yl)-acetate | C21H28N2O4 372.463 | 1.15 LC-2 | 373.13 [M + H]+ |
| Ethyl (3S)-(3-benzyloxycarbonylamino-1,2,3,4-tetrahydro-9H-carbazol-9-yl)-acetate | C24H26N2O4 406.48 | 1.16 LC-2 | 407.2 [M + H]+ |
| Ethyl (3S)-[3-(2-benzyloxy-ethoxycarbonylamino)-1,2,3,4-tetrahydro-9H-carbazol-9-yl]-acetate | C26H30N2O5 450.533 | 1.17 LC-2 | 473.14 [M + Na]+ |

Listed in Table 3a below are further ethyl (3-oxycarbonylamino-1,2,3,4-tetrahydro-9H-carbazol-9-yl)-acetate derivatives of Structure 1, prepared according to the above mentioned method, with the corresponding intermediate of Structure 2a or 2b as starting material.

TABLE 3a

| Intermediates of Structure 1:<br>Ethyl (3-oxycarbonylamino-1,2,3,4-tetrahydro-9H-carbazol-9-yl)-acetate derivatives | Formula MW |
|---|---|
| Ethyl (3RS)-(3-benzyloxycarbonylamino-6-trifluoromethyl-1,2,3,4-tetrahydro-9H-carbazol-9-yl)-acetate | C25H25N2O4F3 474.478 |
| Ethyl (3RS)-(3-benzyloxycarbonylamino-8-bromo-6-fluoro-1,2,3,4-tetrahydro-9H-carbazol-9-yl)-acetate | C24H24N2O4BrF 503.367 |
| Ethyl (3RS)-(3-benzyloxycarbonylamino-6-fluoro-8-vinyl-1,2,3,4-tetrahydro-9H-carbazol-9-yl)-acetate | C26H27N2O4F 450.508 |
| Ethyl (3RS)-(3-benzyloxycarbonylamino-6-fluoro-8-methanesulfonyl-1,2,3,4-tetrahydro-9H-carbazol-9-yl)-acetate | C25H27N2O6FS 502.561 |
| Ethyl (3S)-(3-benzyloxycarbonylamino-6-fluoro-8-methyl-1,2,3,4-tetrahydro-9H-carbazol-9-yl)-acetate | C25H27N2O4F 438.497 |
| Ethyl (3S)-(3-benzyloxycarbonylamino-7-chloro-6-fluoro-1,2,3,4-tetrahydro-9H-carbazol-9-yl)-acetate | C24H24ClFN2O4 458.91 |
| Ethyl (3S)-(8-allyl-3-benzyloxycarbonylamino-6-fluoro-1,2,3,4-tetrahydro-9H-carbazol-9-yl)-acetate | C27H29N2O4F 464.535 |
| Ethyl (3R)-(3-benzyloxycarbonylamino-8-chloro-1,2,3,4-tetrahydro-9H-carbazol-9-yl)-acetate | C24H25N2O4Cl 440.926 |
| Ethyl (3S)-[3-(benzyloxycarbonyl-methyl-amino)-6-fluoro-1,2,3,4-tetrahydro-9H-carbazol-9-yl]-acetate | C25H27N2O4F 438.494 |
| Ethyl {(3S)-3-[(2-chloro-benzyloxycarbonyl)-methyl-amino]-6-fluoro-1,2,3,4-tetrahydro-9H-carbazol-9-yl}-acetate | C25H26N2O4ClF 472.939 |
| Ethyl (3S)-[3-(benzyloxycarbonyl-cyclopropylmethyl-amino)-6-fluoro-1,2,3,4-tetrahydro-9H-carbazol-9-yl]-acetate | C28H31N2O4F 478.558 |
| Ethyl (3S)-(3-{benzyloxycarbonyl-[2-(4-trifluoromethyl-phenoxy)-ethyl]-amino}-6-fluoro-1,2,3,4-tetrahydro-9H-carbazol-9-yl)-acetate | C33H32N2O5F4 612.614 |
| Ethyl (3S)-{3-[benzyloxycarbonyl-(2-methoxy-ethyl)-amino]-6-fluoro-1,2,3,4-tetrahydro-9H-carbazol-9-yl}-acetate | C27H31N2O5F 482.546 |

3) N-Acylation of an Intermediate of Structure 2a or 2b

Method (A)

The appropriate acid chloride (0.132 mmol) and a catalytical amount of DMAP are added to a stirred solution of a hydrochloride of the appropriate intermediate of Structure 2a or 2b (0.11 mmol) and Et₃N (0.034 ml, 0.242 mmol) in DCM (2 ml) at 0° C., and the resulting reaction mixture is kept stirring at rt overnight. Then, a (1:4) mixture (1 ml) of sat. NaHCO₃ and H₂O is added. After phase separation, the aq. layer is extracted three times with DCM, and the combined org. layers are washed with 10% citric acid to remove DMAP. The solvent is evaporated and the pure ethyl (3-acylamido-1,2,3,4-tetrahydro-9H-carbazol-9-yl)-acetate derivative of Structure 1 is isolated by preparative HPLC in 10 to 95% yield.

Method (B)

A solution of a hydrochloride of the appropriate intermediate of Structure 2a or 2b (0.075 mmol) and DIEA (0.15 mmol) in a 4:1 mixture (2 ml) of dry DMF and THF is added dropwise to a stirred solution of the appropriate carboxylic acid (0.113 mmol), HATU (0.15 mmol) and DIEA (0.15 mmol) in a 4:1 mixture (2 ml) of dry DMF and THF at 0° C. The mixture is stirred at rt for 1 h, or overnight, then sat. NaHCO₃ solution is added. After phase separation, the aq. layer is extracted three times with DCM. The combined org. phases are evaporated. The crude ethyl (3-acylamido-1,2,3,4-tetrahydro-9H-carbazol-9-yl)-acetate derivative of Structure 1 is obtained with >50% yield and is either used as such in the next step or purified by preparative HPLC to give the pure ethyl (3-acylamino-1,2,3,4-tetrahydro-9H-carbazol-9-yl)-acetate derivative of Structure 1 with 13 to 95% yield.

Listed in Table 4 below are crude ethyl (3-acylamino-1,2,3,4-tetrahydro-9H-carbazol-9-yl)-acetate derivatives of Structure 1, prepared according to the above mentioned methods (A) or (B), with the corresponding intermediate of Structure 2a or 2b as starting material.

TABLE 4

| Intermediates of Structure 1: Ethyl (3-acylamino-1,2,3,4-tetrahydro-9H-carbazol-9-yl)-acetate derivatives | Formula MW | $t_R$ [min] LC-MS Method | MS Data m/z [M + H]⁺ |
|---|---|---|---|
| Ethyl (3R)-(3-benzoylamino-1,2,3,4-tetrahydro-9H-carbazol-9-yl)-acetate | C23H24N2O3 376.455 | 1.11 LC-2 | 399.00 [M + Na]⁺ |
| Ethyl (3R)-[3-(2-phenoxy-acetylamino)-1,2,3,4-tetrahydro-9H-carbazol-9-yl]-acetate | C24H26N2O4 406.48 | 1.13 LC-2 | 428.93 [M + Na]⁺ |
| Ethyl (3R)-(3-phenylacetylamino-1,2,3,4-tetrahydro-9H-carbazol-9-yl)-acetate | C24H26N2O3 390.481 | 1.11 LC-2 | 412.97 [M + Na]⁺ |
| Ethyl (3R)-[3-(2-thiophen-2-yl-acetylamino)-1,2,3,4-tetrahydro-9H-carbazol-9-yl]-acetate | C22H24N2O3S 396.51 | 1.09 LC-2 | 396.98 |
| Ethyl (3R)-[3-(3-phenyl-propionylamino)-1,2,3,4-tetrahydro-9H-carbazol-9-yl]-acetate | C25H28N2O3 404.508 | 1.13 LC-2 | 427.03 [M + Na]⁺ |
| Ethyl (3R)-[3-(2-benzyloxy-acetylamino)-1,2,3,4-tetrahydro-9H-carbazol-9-yl]-acetate | C25H28N2O4 420.507 | 1.14 LC-2 | 421.07 |
| Ethyl (3R)-[3-(3-methyl-butyrylamino)-1,2,3,4-tetrahydro-9H-carbazol-9-yl]-acetate | C21H28N2O3 356.464 | 1.09 LC-2 | 357.1 |
| Ethyl (3R)-[3-(3-cyclopentyl-propionylamino)-1,2,3,4-tetrahydro-9H-carbazol-9-yl]-acetate | C24H32N2O3 396.529 | 1.17 LC-2 | 397.05 |
| Ethyl (3R)-(3-decanoylamino-1,2,3,4-tetrahydro-9H-carbazol-9-yl)-acetate | C26H38N2O3 426.599 | 1.28 LC-2 | 449.01 [M + Na]⁺ |
| Ethyl (3S)-[3-(2-phenoxy-acetylamino)-1,2,3,4-tetrahydro-9H-carbazol-9-yl]-acetate | C24H26N2O4 406.48 | 1.03 LC-2 | 407.23 |
| Ethyl (3S)-(3-phenylacetylamino-1,2,3,4-tetrahydro-9H-carbazol-9-yl)-acetate | C24H26N2O3 390.481 | 1.1 LC-2 | 391.13 |
| Ethyl (3S)-[3-(2-thiophen-2-yl-acetylamino)-1,2,3,4-tetrahydro-9H-carbazol-9-yl]-acetate | C22H24N2O3S 396.51 | 1.1 LC-2 | 397 |
| Ethyl (3S)-[3-(3-phenyl-propionylamino)-1,2,3,4-tetrahydro-9H-carbazol-9-yl]-acetate | C25H28N2O3 404.508 | 1.13 LC-2 | 405.12 |
| Ethyl (3S)-[3-(2-benzyloxy-acetylamino)-1,2,3,4-tetrahydro-9H-carbazol-9-yl]-acetate | C25H28N2O4 420.507 | 1.14 LC-2 | 421.09 |
| Ethyl (3S)-[3-(3-methyl-butyrylamino)-1,2,3,4-tetrahydro-9H-carbazol-9-yl]-acetate | C21H28N2O3 356.464 | 1.1 LC-2 | 357.13 |
| Ethyl (3S)-[3-(3-cyclopentyl-propionylamino)-1,2,3,4-tetrahydro-9H-carbazol-9-yl]-acetate | C24H32N2O3 396.529 | 1.18 LC-2 | 397.16 |
| Ethyl (3S)-(3-decanoylamino-1,2,3,4-tetrahydro-9H-carbazol-9-yl)-acetate | C26H38N2O3 426.599 | 1.15 LC-2 | 427.32 |
| Ethyl (3S)-(3-butyrylamino-1,2,3,4-tetrahydro-9H-carbazol-9-yl)-acetate | C20H26N2O3 342.437 | 1.07 LC-2 | 343.15 |
| Ethyl (3S)-(3-heptanoylamino-1,2,3,4-tetrahydro-9H-carbazol-9-yl)-acetate | C23H32N2O3 384.518 | 1.18 LC-2 | 385.18 |
| Ethyl (3R)-[6-fluoro-3-(2-phenoxy-acetylamino)-1,2,3,4-tetrahydro-9H-carbazol-9-yl]-acetate | C24H25N2O4F 424.471 | 1.15 LC-2 | 425.28 |
| Ethyl (3R)-(6-fluoro-3-phenylacetylamino-1,2,3,4-tetrahydro-9H-carbazol-9-yl)-acetate | C24H25N2O3F 408.472 | 1.12 LC-2 | 409.28 |
| Ethyl (3R)-[6-Fluoro-3-(3-phenyl-propionylamino)-1,2,3,4-tetrahydro-9H-carbazol-9-yl]-acetate | C25H27N2O3F 422.498 | 1.15 LC-2 | 423.27 |
| Ethyl (3R)-{3-[2-(4-Chloro-phenyl)-acetylamino]-6-fluoro-1,2,3,4-tetrahydro-9H-carbazol-9-yl}-acetate | C24H24N2O3ClF 442.917 | 1.18 LC-2 | 443.21 |
| Ethyl (3R)-{6-fluoro-3-[2-(4-methoxy-phenyl)-acetylamino]-1,2,3,4-tetrahydro-9H-carbazol-9-yl}-acetate | C25H27N2O4F 438.497 | 1.12 LC-2 | 439.2 |
| Ethyl (3R)-[6-fluoro-3-(2-p-tolyl-acetylamino)-1,2,3,4-tetrahydro-9H-carbazol-9-yl]-acetate | C25H27N2O3F 422.498 | 1.14 LC-2 | 423.34 |
| Ethyl (3R)-{3-[2-(3,4-dichloro-phenyl)-acetylamino]-6-fluoro-1,2,3,4-tetrahydro-9H-carbazol-9-yl}-acetate | C24H23N2O3Cl2F 477.362 | 1.18 LC-2 | 477.22 |
| Ethyl (3R)-{3-[2-(3-chloro-phenyl)-acetylamino]-6-fluoro-1,2,3,4-tetrahydro-9H-carbazol-9-yl}-acetate | C24H24N2O3ClF 442.917 | 1.16 LC-2 | 443.28 |
| Ethyl (3R)-{6-fluoro-3-[2-(4-trifluoromethyl-phenyl)-acetylamino]-1,2,3,4-tetrahydro-9H-carbazol-9-yl}-acetate | C25H24N2O3F4 476.469 | 1.17 LC-2 | 477.29 |
| Ethyl (3R)-{3-[2-(4-chloro-phenoxy)-acetylamino]-6-fluoro-1,2,3,4-tetrahydro-9H-carbazol-9-yl}-acetate | C24H24N2O4ClF 458.916 | 1.18 LC-2 | 459.28 |
| Ethyl (3R)-[6-fluoro-3-(2-p-tolyloxy-acetylamino)-1,2,3,4-tetrahydro-9H-carbazol-9-yl]-acetate | C25H27N2O4F 438.497 | 1.18 LC-2 | 439.27 |
| Ethyl (3R)-{3-[2-(2-chloro-phenoxy)-acetylamino]-6-fluoro-1,2,3,4-tetrahydro-9H-carbazol-9-yl}-acetate | C24H24N2O4ClF 458.916 | 1.17 LC-2 | 459.21 |
| Ethyl (3R)-{3-[2-(3-chloro-phenoxy)-acetylamino]-6-fluoro-1,2,3,4-tetrahydro-9H-carbazol-9-yl}-acetate | C24H24N2O4ClF 458.916 | 1.18 LC-2 | 459.21 |
| Ethyl (3R)-{6-fluoro-3-[3-(4-methoxy-phenyl)-propionylamino]-1,2,3,4-tetrahydro-9H-carbazol-9-yl}-acetate | C26H29N2O4F 452.524 | 1.14 LC-2 | 453.26 |
| Ethyl (3R)-[6-fluoro-3-(3-p-tolyl-propionylamino)-1,2,3,4-tetrahydro-9H-carbazol-9-yl]-acetate | C26H29N2O3F 436.525 | 1.17 LC-2 | 437.26 |
| Ethyl (3R)-{3-[3-(4-chloro-phenyl)-propionylamino]-6-fluoro-1,2,3,4-tetrahydro-9H-carbazol-9-yl}-acetate | C25H26N2O3ClF 456.943 | 1.18 LC-2 | 457.2 |

TABLE 4-continued

| Intermediates of Structure 1: Ethyl (3-acylamino-1,2,3,4-tetrahydro-9H-carbazol-9-yl)-acetate derivatives | Formula MW | $t_R$ [min] LC-MS Method | MS Data m/z [M + H]$^+$ |
|---|---|---|---|
| Ethyl (3R)-{3-[3-(2-chloro-phenyl)-propionylamino]-6-fluoro-1,2,3,4-tetrahydro-9H-carbazol-9-yl}-acetate | C25H26N2O3ClF 456.943 | 1.18 LC-2 | 457.2 |
| Ethyl (3R)-{3-[3-(3-chloro-phenyl)-propionylamino]-6-fluoro-1,2,3,4-tetrahydro-9H-carbazol-9-yl}-acetate | C25H26N2O3ClF 456.943 | 1.17 LC-2 | 457.2 |
| Ethyl (3S)-{3-[2-(4-chloro-phenyl)-acetylamino]-6-fluoro-1,2,3,4-tetrahydro-9H-carbazol-9-yl}-acetate | C24H24N2O3ClF 442.917 | 1.15 LC-2 | 443.21 |
| Ethyl (3S)-{6-fluoro-3-[2-(4-methoxy-phenyl)-acetylamino]-1,2,3,4-tetrahydro-9H-carbazol-9-yl}-acetate | C25H27N2O4F 438.497 | 1.12 LC-2 | 439.33 |
| Ethyl (3S)-[6-fluoro-3-(2-p-tolyl-acetylamino)-1,2,3,4-tetrahydro-9H-carbazol-9-yl]-acetate | C25H27N2O3F 422.498 | 1.15 LC-2 | 423.27 |
| Ethyl (3S)-[6-fluoro-3-(2-phenoxy-acetylamino)-1,2,3,4-tetrahydro-9H-carbazol-9-yl]-acetate | C24H25N2O4F 424.471 | 1.15 LC-2 | 425.28 |
| Ethyl (3S)-[6-fluoro-3-(3-phenyl-propionylamino)-1,2,3,4-tetrahydro-9H-carbazol-9-yl]-acetate | C25H27N2O3F 422.498 | 1.14 LC-2 | 423.27 |
| Ethyl (3S)-{3-[2-(4-chloro-phenoxy)-acetylamino]-6-fluoro-1,2,3,4-tetrahydro-9H-carbazol-9-yl}-acetate | C24H24N2O4ClF 458.916 | 1.17 LC-2 | 459.21 |
| Ethyl (3S)-[6-fluoro-3-(2-p-tolyloxy-acetylamino)-1,2,3,4-tetrahydro-9H-carbazol-9-yl]-acetate | C25H27N2O4F 438.497 | 1.18 LC-2 | 439.27 |
| Ethyl (3S)-{6-fluoro-3-[3-(4-methoxy-phenyl)-propionylamino]-1,2,3,4-tetrahydro-9H-carbazol-9-yl}-acetate | C26H29N2O4F 452.524 | 1.14 LC-2 | 453.33 |
| Ethyl (3S)-[6-fluoro-3-(3-p-tolyl-propionylamino)-1,2,3,4-tetrahydro-9H-carbazol-9-yl]-acetate | C26H29N2O3F 436.525 | 1.17 LC-2 | 437.33 |
| Ethyl (3S)-{3-[3-(4-chloro-phenyl)-propionylamino]-6-fluoro-1,2,3,4-tetrahydro-9H-carbazol-9-yl}-acetate | C25H26N2O3ClF 456.943 | 1.17 LC-2 | 457.27 |
| Ethyl (3S)-{3-[3-(2-chloro-phenyl)-propionylamino]-6-fluoro-1,2,3,4-tetrahydro-9H-carbazol-9-yl}-acetate | C25H26N2O3ClF 456.943 | 1.17 LC-2 | 457.27 |
| Ethyl (3S)-{3-[3-(3-chloro-phenyl)-propionylamino]-6-fluoro-1,2,3,4-tetrahydro-9H-carbazol-9-yl}-acetate | C25H26N2O3ClF 456.943 | 1.18 LC-2 | 457.27 |
| Ethyl (3S)-{3-[3-(3,4-difluoro-phenyl)-propionylamino]-6-fluoro-1,2,3,4-tetrahydro-9H-carbazol-9-yl}-acetate | C25H25N2O3F3 458.479 | 1.17 LC-2 | 459.28 |
| Ethyl (3S)-{6-fluoro-3-[3-(3-methoxy-phenyl)-propionylamino]-1,2,3,4-tetrahydro-9H-carbazol-9-yl}-acetate | C26H29N2O4F 452.524 | 1.14 LC-2 | 453.33 |
| Ethyl (3S)-{6-fluoro-3-[3-(2-methoxy-phenyl)-propionylamino]-1,2,3,4-tetrahydro-9H-carbazol-9-yl}-acetate | C26H29N2O4F 452.524 | 1.16 LC-2 | 453.33 |
| Ethyl (3S)-[3-(2,3-diphenyl-propionylamino)-6-fluoro-1,2,3,4-tetrahydro-9H-carbazol-9-yl]-acetate | C31H31N2O3F 498.596 | 1.21 LC-2 | 499.39 |
| Ethyl (3S)-[3-(3,3-diphenyl-propionylamino)-6-fluoro-1,2,3,4-tetrahydro-9H-carbazol-9-yl]-acetate | C31H31N2O3F 498.596 | 1.2 LC-2 | 499.39 |
| Ethyl (3S)-{3-[4-(4-bromo-phenyl)-4-oxo-butyrylamino]-6-fluoro-1,2,3,4-tetrahydro-9H-carbazol-9-yl}-acetate | C26H26N2O4BrF 529.404 | 1.17 LC-2 | 531.25 |
| Ethyl (3S)-[6-fluoro-3-(4-oxo-4-phenyl-butyrylamino)-1,2,3,4-tetrahydro-9H-carbazol-9-yl]-acetate | C26H27N2O4F 450.508 | 1.12 LC-2 | 451.25 |
| Ethyl (3S)-{6-Fluoro-3-[4-(4-methanesulfonyl-phenyl)-4-oxo-butyrylamino]-1,2,3,4-tetrahydro-9H-carbazol-9-yl}-acetate | C27H29N2O6FS 528.599 | 1.07 LC-2 | 529.31 |
| Ethyl (3S)-[6-fluoro-3-(2-indan-2-yl-acetylamino)-1,2,3,4-tetrahydro-9H-carbazol-9-yl]-acetate | C27H29N2O3F 448.536 | 1.18 LC-2 | 449.31 |
| Ethyl (3S)-{6-fluoro-3-[3-(4-hydroxy-3-methoxy-phenyl)-propionylamino]-1,2,3,4-tetrahydro-9H-carbazol-9-yl}-acetate | C26H29FN2O5 468.52 | 1.08 LC-3 | 469.04 |
| Ethyl (3S)-{6-fluoro-3-[3-(4-hydroxy-phenyl)-propionylamino]-1,2,3,4-tetrahydro-9H-carbazol-9-yl}-acetate | C25H27FN2O4 438.49 | 1.07 LC-3 | 439.06 |
| Ethyl (3S)-{6-fluoro-3-[3-(3-hydroxy-phenyl)-propionylamino]-1,2,3,4-tetrahydro-9H-carbazol-9-yl}-acetate | C25H27FN2O5 439.49 | 1.08 LC-3 | 439.06 |
| Ethyl (3S)-{6-fluoro-3-[3-(2-hydroxy-phenyl)-propionylamino]-1,2,3,4-tetrahydro-9H-carbazol-9-yl}-acetate | C25H27FN2O6 440.49 | n.d. LC-3 | n.d. |
| Ethyl (3S)-{3-[(2,3-dihydro-1H-indole-2-carbonyl)-amino]-6-fluoro-1,2,3,4-tetrahydro-9H-carbazol-9-yl}-acetate | C25H26FN3O3 435.49 | 1.14 LC-3 | 436.08 |

TABLE 4-continued

| Intermediates of Structure 1: Ethyl (3-acylamino-1,2,3,4-tetrahydro-9H-carbazol-9-yl)-acetate derivatives | Formula MW | $t_R$ [min] LC-MS Method | MS Data m/z $[M + H]^+$ |
|---|---|---|---|
| Ethyl (3S)-[6-fluoro-3-(3-1H-indol-3-yl-propionylamino)-1,2,3,4-tetrahydro-9H-carbazol-9-yl]-acetate | C27H28FN3O3 461.53 | 1.15 LC-3 | 462.05 |
| Ethyl (3S)-[3-(3-1H-benzoimidazol-2-yl-propionylamino)-6-fluoro-1,2,3,4-tetrahydro-9H-carbazol-9-yl]-acetate | C26H27FN4O3 462.52 | 0.86 LC-3 | 463.09 |
| Ethyl (3S)-[3-(3-benzo[1,3]dioxol-5-yl-propionylamino)-6-fluoro-1,2,3,4-tetrahydro-9H-carbazol-9-yl]-acetate | C26H27FN2O5 466.5 | 1.15 LC-3 | 467.03 |
| Ethyl (3S)-{6-fluoro-3-[(1H-indole-2-carbonyl)-amino]-1,2,3,4-tetrahydro-9H-carbazol-9-yl}-acetate | C25H24FN3O3 433.47 | n.d. LC-3 | n.d. |
| Ethyl (3S)-[6-fluoro-3-(3-pyridin-3-yl-propionylamino)-1,2,3,4-tetrahydro-9H-carbazol-9-yl]-acetate | C24H26FN3O3 423.48 | n.d. LC-3. | n.d. |
| Ethyl (3S)-{3-[2-(4-tert-butyl-phenyl)-acetylamino]-6-fluoro-1,2,3,4-tetrahydro-9H-carbazol-9-yl}-acetate | C28H33FN2O3 464.57 | n.d. LC-3 | n.d. |
| Ethyl (3S)-{6-fluoro-3-[2-(4-trifluoromethyl-phenyl)-acetylamino]-1,2,3,4-tetrahydro-9H-carbazol-9-yl}-acetate | C25H24F4N2O3 476.46 | n.d. LC-3 | n.d. |
| Ethyl (3S)-{6-fluoro-3-[2-(3-trifluoromethyl-phenyl)-acetylamino]-1,2,3,4-tetrahydro-9H-carbazol-9-yl}-acetate | C25H24F4N2O3 476.46 | 1.26 LC-2 | 477.04 |
| Ethyl (3S)-{6-fluoro-3-[2-(4-trifluoromethyl-phenoxy)-acetylamino]-1,2,3,4-tetrahydro-9H-carbazol-9-yl}-acetate | C25H24F4N2O4 492.46 | n.d. LC-3. | n.d. |
| Ethyl (3S)-[6-fluoro-3-(3-naphthalen-2-yl-acryloylamino)-1,2,3,4-tetrahydro-9H-carbazol-9-yl]-acetate | C29H27FN2O3 470.53 | 1.29 LC-2 | 471.05 |
| Ethyl (3S)-[6-fluoro-3-(3-naphthalen-2-yl-propionylamino)-1,2,3,4-tetrahydro-9H-carbazol-9-yl]-acetate | C29H29FN2O3 472.55 | 1.27 LC-2 | 473.08 |
| Ethyl (3S)-{6-fluoro-3-[methyl-(3-phenyl-propionyl)-amino]-1,2,3,4-tetrahydro-9H-carbazol-9-yl}-acetate | C26H29FN2O3 436.52 | 1.08 LC-3 | 437.28 |
| Ethyl (3S)-(3-{[2-(4-chloro-phenyl)-acetyl]-methyl-amino}-6-fluoro-1,2,3,4-tetrahydro-9H-carbazol-9-yl)-acetate | C25H26ClFN2O3 456.94 | 1.09 LC-3 | 473.08 |
| Ethyl (3S)-{6-fluoro-3-[ethyl-(3-phenyl-propionyl)-amino]-1,2,3,4-tetrahydro-9H-carbazol-9-yl}-acetate | C27H31FN2O3 450.55 | 1.09 LC-3 | 451.23 |
| Ethyl (3S)-(3-{[2-(4-chloro-phenyl)-acetyl]-ethyl-amino}-6-fluoro-1,2,3,4-tetrahydro-9H-carbazol-9-yl)-acetate | C26H28ClFN2O3 470.96 | 1.1 LC-3 | 471.22 |
| Ethyl (3S)-{6-fluoro-3-[propyl-(3-phenyl-propionyl)-amino]-1,2,3,4-tetrahydro-9H-carbazol-9-yl}-acetate | C28H33FN2O3 464.57 | 1.11 LC-3 | 465.23 |
| Ethyl (3S)-(3-{[2-(4-chloro-phenyl)-acetyl]-propyl-amino}-6-fluoro-1,2,3,4-tetrahydro-9H-carbazol-9-yl)-acetate | C27H30ClFN2O 484.99 | 1.12 LC-3 | 485.20 |

Listed in Table 4a below are further ethyl (3-acylamino-1,2,3,4-tetrahydro-9H-carbazol-9-yl)-acetate derivatives of Structure 1, prepared according to the above mentioned methods (A) or (B), with the corresponding intermediate of Structure 2a or 2b as starting material.

TABLE 4a

| Intermediates of Structure 1: Ethyl (3-acylamino-1,2,3,4-tetrahydro-9H-carbazol-9-yl)-acetate derivatives | Formula MW |
|---|---|
| (3S)-{3-[3-(2,4-dimethoxy-phenyl)-propionylamino]-6-fluoro-1,2,3,4-tetrahydro-9H-carbazol-9-yl}-acetate | C27H31N2O5F 482.546 |
| Ethyl (3S)-[6-fluoro-3-(3-naphthalen-1-yl-propionylamino)-1,2,3,4-tetrahydro-9H-carbazol-9-yl]-acetate | C29H29N2O3F 472.555 |
| Ethyl (3RS)-{6-fluoro-3-[2-(2-methoxy-phenoxy)-acetylamino]-1,2,3,4-tetrahydro-9H-carbazol-9-yl}-acetate | C25H27N2O5F 454.493 |
| Ethyl (3RS)-{6-fluoro-3-[3-(2-methylphenyl)-propionylamino]-1,2,3,4-tetrahydro-9H-carbazol-9-yl}-acetate | C26H29N2O3F 436.522 |
| Ethyl (3RS)-{6-fluoro-3-[3-(3-methylphenyl)-propionylamino]-1,2,3,4-tetrahydro-9H-carbazol-9-yl}-acetate | C26H29N2O3F 436.522 |
| Ethyl (3RS)-{6-fluoro-3-[3-(3-methoxy-phenyl)-propionylamino]-1,2,3,4-tetrahydro-9H-carbazol-9-yl}-acetate | C26H29N2O4F 452.521 |
| Ethyl (3RS)-{6-fluoro-3-[2-(3-methoxy-phenoxy)-acetylamino]-1,2,3,4-tetrahydro-9H-carbazol-9-yl}-acetate | C25H27N2O5F 454.493 |

TABLE 4a-continued

| Intermediates of Structure 1: Ethyl (3-acylamino-1,2,3,4-tetrahydro-9H-carbazol-9-yl)-acetate derivatives | Formula MW |
|---|---|
| Ethyl (3RS)-{6-fluoro-3-[2-(2-methylphenoxy)-acetylamino]-1,2,3,4-tetrahydro-9H-carbazol-9-yl}-acetate | C25H27N2O4F 438.494 |
| Ethyl (3S)-{3-[3-(2,5-dimethoxy-phenyl)-propionylamino]-6-fluoro-1,2,3,4-tetrahydro-9H-carbazol-9-yl}-acetate | C22H31N2O5F 482.546 |
| Ethyl (3S)-{6-fluoro-3-[3-(4-trifluoromethyl-phenyl)-propionylamino]-1,2,3,4-tetrahydro-9H-carbazol-9-yl}-acetate | C26H26N2O3F4 490.492 |
| Ethyl (3S)-{3-[3-(2,6-dichloro-phenyl)-propionylamino]-6-fluoro-1,2,3,4-tetrahydro-9H-carbazol-9-yl}-acetate | C25H25N2O3Cl2F 491.385 |
| Ethyl (3S)-{3-[3-(2,5-bis-trifluoromethyl-phenyl)-propionylamino]-6-fluoro-1,2,3,4-tetrahydro-9H-carbazol-9-yl}-acetate | C27H25N2O3F7 558.489 |
| Ethyl (3S)-{6-fluoro-3-[3-(4-methylsulfanyl-phenyl)-propionylamino]-1,2,3,4-tetrahydro-9H-carbazol-9-yl}-acetate | C26H29N2O3FS 468.588 |
| Ethyl (3S)-{6-fluoro-3-[3-(4-iodo-phenyl)-propionylamino]-1,2,3,4-tetrahydro-9H-carbazol-9-yl}-acetate | C25H26N2O3FI 548.387 |
| Ethyl (3S)-{6-fluoro-3-[3-(4-isopropyl-phenyl)-propionylamino]-1,2,3,4-tetrahydro-9H-carbazol-9-yl}-acetate | C28H33N2O3F 464.575 |
| Ethyl (3S)-{6-fluoro-3-[3-(3-trifluoromethyl-phenyl)-propionylamino]-1,2,3,4-tetrahydro-9H-carbazol-9-yl}-acetate | C26H26N2O3F4 490.492 |
| Ethyl (3S)-{3-[3-(2,4-dichloro-phenyl)-propionylamino]-6-fluoro-1,2,3,4-tetrahydro-9H-carbazol-9-yl}-acetate | C25H25N2O3Cl2F 491.385 |
| Ethyl (3S)-{6-fluoro-3-[3-(4-fluoro-phenyl)-propionylamino]-1,2,3,4-tetrahydro-9H-carbazol-9-yl}-acetate | C25H26N2O3F2 440.485 |
| Ethyl (3S)-{3-[3-(3,5-bis-trifluoromethyl-phenyl)-propionylamino]-6-fluoro-1,2,3,4-tetrahydro-9H-carbazol-9-yl}-acetate | C27H25N2O3F7 558.489 |
| Ethyl (3S)-{3-[3-(4-ethyl-phenyl)-propionylamino]-6-fluoro-1,2,3,4-tetrahydro-9H-carbazol-9-yl}-acetate | C27H31N2O3F 450.548 |
| Ethyl (3S)-{6-fluoro-3-[3-(3-iodo-phenyl)-propionylamino]-1,2,3,4-tetrahydro-9H-carbazol-9-yl}-acetate | C25H26N2O3FI 548.387 |
| Ethyl (3S)-{6-fluoro-3-[3-(4-methanesulfonyl-phenyl)-propionylamino]-1,2,3,4-tetrahydro-9H-carbazol-9-yl}-acetate | C26H29N2O5FS 500.586 |
| Ethyl (3S)-{3-[3-(2,3-dimethoxy-phenyl)-propionylamino]-6-fluoro-1,2,3,4-tetrahydro-9H-carbazol-9-yl}-acetate | C27H31N2O5F 482.546 |
| Ethyl (3S)-{3-[3-(2-bromo-phenyl)-propionylamino]-6-fluoro-1,2,3,4-tetrahydro-9H-carbazol-9-yl}-acetate | C25H26N2O3BrF 501.391 |
| Ethyl (3S)-{6-fluoro-3-[3-(3-trifluoromethoxy-phenyl)-propionylamino]-1,2,3,4-tetrahydro-9H-carbazol-9-yl}-acetate | C26H26N2O4F4 506.491 |
| Ethyl (3S)-{3-[3-(2,4-dimethyl-phenyl)-propionylamino]-6-fluoro-1,2,3,4-tetrahydro-9H-carbazol-9-yl}-acetate | C27H31N2O3F 450.548 |
| Ethyl (3S)-{3-[3-(3-bromo-phenyl)-propionylamino]-6-fluoro-1,2,3,4-tetrahydro-9H-carbazol-9-yl}-acetate | C25H26N2O3BrF 501.391 |
| Ethyl (3S)-{3-[3-(3-tert-butoxycarbonylamino-phenyl)-propionylamino]-6-fluoro-1,2,3,4-tetrahydro-9H-carbazol-9-yl}-acetate | C30H36N3O5F 537.626 |
| Ethyl (3S)-{6-fluoro-3-[(S)-3-(4-fluoro-phenyl)-2-phenyl-propionylamino]-1,2,3,4-tetrahydro-9H-carbazol-9-yl}-acetate | C31H30N2O3F2 516.582 |
| Ethyl (3S)-{6-fluoro-3-[(S)-3-(4-methoxy-phenyl)-2-phenyl-propionylamino]-1,2,3,4-tetrahydro-9H-carbazol-9-yl}-acetate | C32H33N2O4F 528.618 |
| Ethyl (3S)-{6-fluoro-3-[3-(2-fluoro-phenyl)-propionylamino]-1,2,3,4-tetrahydro-9H-carbazol-9-yl}-acetate | C25H26N2O3F2 440.485 |
| Ethyl (3S)-{(6-fluoro-3-{[(2RS)-1,2,3,4-tetrahydro-naphthalene-2-carbonyl]-amino}-1,2,3,4-tetrahydro-9H-carbazol-9-yl)-acetate | C27H29N2O3F 448.533 |
| Ethyl (3S)-{(6-fluoro-3-{[(2RS)-8-methoxy-1,2,3,4-tetrahydro-naphthalene-2-carbonyl]-amino}-1,2,3,4-tetrahydro-9H-carbazol-9-yl)-acetate | C28H31N2O4F 478.558 |
| Ethyl (3S)-(6-fluoro-3-{(2RS)-2-[(4-fluoro-phenylcarbamoyl)-methyl]-3-phenyl-propionylamino}-1,2,3,4-tetrahydro-9H-carbazol-9-yl)-acetate | C33H33N3O4F2 573.634 |
| Ethyl (3S)-{3-[(2RS)-2-benzyl-3,3-dimethyl-butyrylamino]-6-fluoro-1,2,3,4-tetrahydro-9H-carbazol-9-yl}-acetate | C29H35N2O3F 478.602 |
| Ethyl (3S)-(3-{[(3RS)-chroman-3-carbonyl]-amino}-6-fluoro-1,2,3,4-tetrahydro-9H-carbazol-9-yl)-acetate | C26H27N2O4F 450.505 |
| Ethyl (3S)-{6-fluoro-3-[3-(3-fluoro-phenyl)-propionylamino]-1,2,3,4-tetrahydro-9H-carbazol-9-yl}-acetate | C25H26N2O3F2 440.485 |
| Ethyl (3S)-(6-fluoro-3-{[(1R,2R)-2-phenyl-cyclopropanecarbonyl]-amino}-1,2,3,4-tetrahydro-9H-carbazol-9-yl)-acetate | C26H27N2O3F 434.506 |
| Ethyl (3S)-{6-fluoro-3-[(2R)-2-methyl-3-phenyl-propionylamino]-1,2,3,4-tetrahydro-9H-carbazol-9-yl}-acetate | C26H29N2O3F 436.522 |
| Ethyl (3S)-[3-(2,2-dimethyl-3-phenyl-propionylamino)-6-fluoro-1,2,3,4-tetrahydro-9H-carbazol-9-yl]-acetate | C27H31N2O3F 450.552 |
| Ethyl (3S)-[6-fluoro-3-(3-methyl-3-phenyl-butyrylamino)-1,2,3,4-tetrahydro-9H-carbazol-9-yl]-acetate | C27H31N2O3F 450.548 |
| Ethyl (3S)-{6-fluoro-3-[(3S)-3-phenyl-butyrylamino]-1,2,3,4-tetrahydro-9H-carbazol-9-yl}-acetate | C26H29N2O3F 436.522 |
| Ethyl (3S)-[3-(2-benzyloxy-acetylamino)-6-fluoro-1,2,3,4-tetrahydro-9H-carbazol-9-yl]-acetate | C25H27N2O4F 438.494 |
| Ethyl (3S)-[6-fluoro-3-(4-phenyl-butyrylamino)-1,2,3,4-tetrahydro-9H-carbazol-9-yl]-acetate | C26H29N2O3F 436.522 |
| Ethyl (3S)-{3-[(2R,3R)-2,3-dihydroxy-3-(2-methoxy-phenylcarbamoyl)-propionylamino]-6-fluoro-1,2,3,4-tetrahydro-9H-carbazol-9-yl}-acetate | C27H30N3O7F 527.543 |
| Ethyl (3RS)-{8-chloro-6-fluoro-3-[3-(2-methylphenyl)-propionylamino]-1,2,3,4-tetrahydro-9H-carbazol-9-yl}-acetate | C26H28N2O3ClF 470.967 |
| Ethyl (3RS)-{8-chloro-6-fluoro-3-[2-(2-methoxy-phenoxy)-acetylamino]-1,2,3,4-tetrahydro-9H-carbazol-9-yl}-acetate | C25H26N2O5ClF 488.938 |
| Ethyl (3RS)-{8-chloro-6-fluoro-3-[3-(3-hydroxy-phenyl)-propionylamino]-1,2,3,4-tetrahydro-9H-carbazol-9-yl}-acetate | C25H26N2O4ClF 472.939 |
| Ethyl (3RS)-{8-chloro-6-fluoro-3-[3-(3-methoxy-phenyl)-propionylamino]-1,2,3,4-tetrahydro-9H-carbazol-9-yl}-acetate | C26H28N2O4ClF 486.966 |
| Ethyl (3RS)-{8-chloro-6-fluoro-3-[3-(3-methylphenyl)-propionylamino]-1,2,3,4-tetrahydro-9H-carbazol-9-yl}-acetate | C22H28N2O3ClF 470.967 |
| Ethyl (3RS)-{8-chloro-6-fluoro-3-[3-(2-hydroxy-phenyl)-propionylamino]-1,2,3,4-tetrahydro-9H-carbazol-9-yl}-acetate | C25H26N2O4ClF 472.939 |
| Ethyl (3RS)-[8-chloro-6-fluoro-3-(3-phenyl-propionylamino)-1,2,3,4-tetrahydro-9H-carbazol-9-yl]-acetate | C25H26N2O3ClF 456.94 |
| Ethyl (3RS)-{8-chloro-6-fluoro-3-[3-(2-methoxy-phenyl)-propionylamino]-1,2,3,4-tetrahydro-9H-carbazol-9-yl}-acetate | C26H28N2O4ClF 486.966 |
| Ethyl (3RS)-{8-chloro-3-[3-(3-chloro-phenyl)-propionylamino]-6-fluoro-1,2,3,4-tetrahydro-9H-carbazol-9-yl}-acetate | C25H25N2O3Cl2F 491.385 |
| Ethyl (3RS)-[8-chloro-6-fluoro-3-(3-1H-indol-3-yl-propionylamino)-1,2,3,4-tetrahydro-9H-carbazol-9-yl]-acetate | C27H27N3O3ClF 495.977 |
| Ethyl (3RS)-{8-chloro-3-[2-(2-chloro-phenoxy)-acetylamino]-6-fluoro-1,2,3,4-tetrahydro-9H-carbazol-9-yl}-acetate | C24H23N2O4Cl2F 493.357 |

TABLE 4a-continued

| Intermediates of Structure 1: Ethyl (3-acylamino-1,2,3,4-tetrahydro-9H-carbazol-9-yl)-acetate derivatives | Formula MW |
|---|---|
| Ethyl (3RS)-{8-chloro-6-fluoro-3-[2-(2-methylphenyl)-oxy-acetylamino]-1,2,3,4-tetrahydro-9H-carbazol-9-yl}-acetate | C25H26N2O4ClF 472.939 |
| Ethyl (3RS)-[3-(3-benzo[1,3]dioxol-5-yl-propionylamino)-8-chloro-6-fluoro-1,2,3,4-tetrahydro-9H-carbazol-9-yl]-acetate | C26H26N2O5ClF 500.949 |
| Ethyl (3RS)-{8-chloro-6-fluoro-3-[2-(3-methoxy-phenyl)-acetylamino]-1,2,3,4-tetrahydro-9H-carbazol-9-yl}-acetate | C25H26N2O5ClF 488.938 |
| Ethyl (3RS)-{8-chloro-3-[2-(3-chloro-phenoxy)-acetylamino]-6-fluoro-1,2,3,4-tetrahydro-9H-carbazol-9-yl}-acetate | C24H23N2O4Cl2F 493.357 |
| Ethyl (3RS)-{8-chloro-3-[3-(2-chloro-phenyl)-propionylamino]-6-fluoro-1,2,3,4-tetrahydro-9H-carbazol-9-yl}-acetate | C25H25N2O3Cl2F 491.385 |
| Ethyl (3RS)-[8-chloro-6-fluoro-3-(2-indan-2-yl-acetylamino)-1,2,3,4-tetrahydro-9H-carbazol-9-yl]-acetate | C27H28N2O3ClF 482.978 |
| Ethyl (3S)-(6-fluoro-3-{[2-(4-methoxy-phenyl)-acetyl]-methyl-amino}-1,2,3,4-tetrahydro-9H-carbazol-9-yl)-acetate | C26H29N2O4F 452.521 |
| Ethyl (3S)-(6-fluoro-3-{methyl-[2-(4-methylphenyl)-acetyl]-amino}-1,2,3,4-tetrahydro-9H-carbazol-9-yl)-acetate | C22H29N2O3F 436.522 |
| Ethyl (3S)-(6-fluoro-3-{[2-(2-methoxy-phenyl)-acetyl]-methyl-amino}-1,2,3,4-tetrahydro-9H-carbazol-9-yl)-acetate | C26H29N2O4F 452.521 |
| Ethyl (3S)-{6-fluoro-3-[(2-indan-2-yl-acetyl)-methyl-amino]-1,2,3,4-tetrahydro-9H-carbazol-9-yl}-acetate | C28H31N2O3F 462.559 |
| Ethyl (3S)-(3-{[2-(3-chloro-phenyl)-acetyl]-methyl-amino}-6-fluoro-1,2,3,4-tetrahydro-9H-carbazol-9-yl)-acetate | C25H26N2O3ClF 456.94 |
| Ethyl (3S)-(6-fluoro-3-{methyl-[2-(3-methylphenyl)-acetyl]-amino}-1,2,3,4-tetrahydro-9H-carbazol-9-yl)-acetate | C26H29N2O3F 436.522 |
| Ethyl (3S)-(6-fluoro-3-{[2-(3-methoxy-phenyl)-acetyl]-methyl-amino}-1,2,3,4-tetrahydro-9H-carbazol-9-yl)-acetate | C26H29N2O4F 452.521 |
| Ethyl (3S)-(3-{[2-(2-chloro-phenoxy)-acetyl]-methyl-amino}-6-fluoro-1,2,3,4-tetrahydro-9H-carbazol-9-yl)-acetate | C25H26N2O4ClF 472.939 |
| Ethyl (3S)-(3-{[2-(4-chloro-phenoxy)-acetyl]-methyl-amino}-6-fluoro-1,2,3,4-tetrahydro-9H-carbazol-9-yl)-acetate | C25H26N2O4ClF 472.939 |
| Ethyl (3S)-(6-fluoro-3-{[3-(3-methoxy-phenyl)-propionyl]-methyl-amino}-1,2,3,4-tetrahydro-9H-carbazol-9-yl)-acetate | C27H31N2O4F 466.547 |
| Ethyl (3S)-(6-fluoro-3-{methyl-[2-(2-methylphenyl)-acetyl]-amino}-1,2,3,4-tetrahydro-9H-carbazol-9-yl)-acetate | C26H29N2O3F 436.522 |
| Ethyl (3S)-{3-[(3,3-diphenyl-propionyl)-methyl-amino]-6-fluoro-1,2,3,4-tetrahydro-9H-carbazol-9-yl}-acetate | C32H33N2O3F 512.619 |
| Ethyl (3S)-(6-fluoro-3-{[3-(2-methoxy-phenyl)-propionyl]-methyl-amino}-1,2,3,4-tetrahydro-9H-carbazol-9-yl)-acetate | C27H31N2O4F 466.547 |
| Ethyl (3S)-{6-fluoro-3-[(3-1H-indol-3-yl-propionyl)-methyl-amino]-1,2,3,4-tetrahydro-9H-carbazol-9-yl}-acetate | C28H30N3O3F 475.558 |
| Ethyl (3S)-{3-[(2-benzyloxy-acetyl)-methyl-amino]-6-fluoro-1,2,3,4-tetrahydro-9H-carbazol-9-yl}-acetate | C26H29N2O4F 452.521 |
| Ethyl (3S)-{3-[(2,3-diphenyl-propionyl)-methyl-amino]-6-fluoro-1,2,3,4-tetrahydro-9H-carbazol-9-yl}-acetate | C32H33N2O3F 512.619 |
| Ethyl (3S)-{6-fluoro-3-[[3-(2-methoxy-phenyl)-propionyl]-(3-phenyl-propyl)-amino]-1,2,3,4-tetrahydro-9H-carbazol-9-yl}-acetate | C35H39N2O4F 570.699 |
| Ethyl (3S)-{3-[acetyl-(3-phenyl-propyl)-amino]-6-fluoro-1,2,3,4-tetrahydro-9H-carbazol-9-yl}-acetate | C27H31N2O3F 450.548 |
| Ethyl (3S)-{3-[cyclopropylmethyl-(3-phenyl-propionyl)-amino]-6-fluoro-1,2,3,4-tetrahydro-9H-carbazol-9-yl}-acetate | C29H33N2O3F 476.586 |
| Ethyl (3S)-{3-[cyclopropylmethyl-((S)-2-methyl-3-phenyl-propionyl)-amino]-6-fluoro-1,2,3,4-tetrahydro-9H-carbazol-9-yl}-acetate | C30H35N2O3F 490.613 |
| Ethyl (3S)-(3-{cyclopropylmethyl-[3-(2-methoxy-phenyl)-propionyl]-amino}-6-fluoro-1,2,3,4-tetrahydro-9H-carbazol-9-yl)-acetate | C30H35N2O4F 506.612 |
| Ethyl (3S)-(3-{[2-(3-chloro-phenoxy)-acetyl]-cyclopropylmethyl-amino}-6-fluoro-1,2,3,4-tetrahydro-9H-carbazol-9-yl)-acetate | C28H30N2O4ClF 513.003 |
| Ethyl (3S)-{3-[cyclopropylmethyl-(3,3-diphenyl-propionyl)-amino]-6-fluoro-1,2,3,4-tetrahydro-9H-carbazol-9-yl}-acetate | C35H37N2O3F 552.684 |
| Ethyl (3S)-{3-[cyclopropylmethyl-(2-naphthalen-1-yl-acetyl)-amino]-6-fluoro-1,2,3,4-tetrahydro-9H-carbazol-9-yl}-acetate | C32H33N2O3F 512.619 |
| Ethyl (3S)-(3-{acetyl-[2-(4-trifluoromethyl-phenoxy)-ethyl]-amino}-6-fluoro-1,2,3,4-tetrahydro-9H-carbazol-9-yl)-acetate | C27H28N2O4F4 520.518 |
| Ethyl (3S)-(6-fluoro-3-{propionyl-[2-(4-trifluoromethyl-phenoxy)-ethyl]-amino}-1,2,3,4-tetrahydro-9H-carbazol-9-yl)-acetate | C28H30N2O4F4 534.544 |
| Ethyl (3S)-(6-fluoro-3-{(3-phenyl-propionyl)-[2-(4-trifluoromethyl-phenoxy)-ethyl]-amino}-1,2,3,4-tetrahydro-9H-carbazol-9-yl)-acetate | C34H34N2O4F4 610.642 |
| Ethyl (3S)-(6-fluoro-3-{[3-(2-methoxy-phenyl)-propionyl]-[2-(4-trifluoromethyl-phenoxy)-ethyl]-amino}-1,2,3,4-tetrahydro-9H-carbazol-9-yl)-acetate | C35H36N2O5F4 640.668 |
| Ethyl (3S)-{6-fluoro-3-[(2-phenoxy-ethyl)-(3-phenyl-propionyl)-amino]-1,2,3,4-tetrahydro-9H-carbazol-9-yl}-acetate | C33H35N2O4F 542.645 |
| Ethyl (3S)-{6-fluoro-3-[((S)-2-methyl-3-phenyl-propionyl)-(2-phenoxy-ethyl)-amino]-1,2,3,4-tetrahydro-9H-carbazol-9-yl}-acetate | C34H37N2O4F 556.672 |
| Ethyl (3S)-{6-fluoro-3-[[3-(2-methoxy-phenyl)-propionyl]-(2-phenoxy-ethyl)-amino]-1,2,3,4-tetrahydro-9H-carbazol-9-yl}-acetate | C34H37N2O5F 572.671 |
| Ethyl (3S)-{3-[acetyl-(2-phenoxy-ethyl)-amino]-6-fluoro-1,2,3,4-tetrahydro-9H-carbazol-9-yl}-acetate | C26H29N2O4F 452.521 |
| Ethyl (3S)-{6-fluoro-3-[(2-methoxy-ethyl)-(3-phenyl-propionyl)-amino]-1,2,3,4-tetrahydro-9H-carbazol-9-yl}-acetate | C28H33N2O4F 480.574 |
| Ethyl (3S)-(6-fluoro-3-[(2-methoxy-ethyl)-((S)-2-methyl-3-phenyl-propionyl)-amino]-1,2,3,4-tetrahydro-9H-carbazol-9-yl)-acetate | C29H35N2O4F 494.601 |
| Ethyl (3S)-(6-fluoro-3-{(2-methoxy-ethyl)-[3-(2-methoxy-phenyl)-propionyl]-amino}-1,2,3,4-tetrahydro-9H-carbazol-9-yl)-acetate | C29H35N2O5F 510.6 |
| Ethyl (3S)-{3-[[2-(3-chloro-phenoxy)-acetyl]-(2-methoxy-ethyl)-amino]-6-fluoro-1,2,3,4-tetrahydro-9H-carbazol-9-yl}-acetate | C27H30N2O5ClF 516.991 |
| Ethyl (3S)-{3-[(3,3-diphenyl-propionyl)-(2-methoxy-ethyl)-amino]-6-fluoro-1,2,3,4-tetrahydro-9H-carbazol-9-yl}-acetate | C34H37N2O4F 556.672 |
| Ethyl (3S)-{6-fluoro-3-[(2-methoxy-ethyl)-(2-naphthalen-1-yl-acetyl)-amino]-1,2,3,4-tetrahydro-9H-carbazol-9-yl}-acetate | C31H33N2O4F 516.607 |
| Ethyl (3S)-(6-fluoro-3-{[(2S)-2-methyl-3-phenyl-propionyl]-phenethyl-amino}-1,2,3,4-tetrahydro-9H-carbazol-9-yl)-acetate | C34H37N2O3F 540.673 |
| Ethyl (3S)-(6-fluoro-3-{[3-(2-methoxy-phenyl)-propionyl]-phenethyl-amino}-1,2,3,4-tetrahydro-9H-carbazol-9-yl)-acetate | C34H37N2O4F 556.672 |
| Ethyl (3S)-[3-(acetyl-phenethyl-amino)-6-fluoro-1,2,3,4-tetrahydro-9H-carbazol-9-yl]-acetate | C26H29N2O3F 436.522 |
| Ethyl (3S)-{6-fluoro-3-[(2-naphthalen-1-yl-acetyl)-phenethyl-amino]-1,2,3,4-tetrahydro-9H-carbazol-9-yl}-acetate | C36H35N2O3F 562.679 |
| Ethyl (3S)-{6-fluoro-3-[phenethyl-(3-phenyl-propionyl)-amino]-1,2,3,4-tetrahydro-9H-carbazol-9-yl}-acetate | C33H35N2O3F 526.646 |
| Ethyl (3S)-[3-(3-benzyl-1-naphthalen-1-ylmethyl-ureido)-6-fluoro-1,2,3,4-tetrahydro-9H-carbazol-9-yl]-acetate | C35H34N3O3F 563.667 |

TABLE 4a-continued

| Intermediates of Structure 1: Ethyl (3-acylamino-1,2,3,4-tetrahydro-9H-carbazol-9-yl)-acetate derivatives | Formula MW |
|---|---|
| Ethyl (3S)-[3-(benzyloxycarbonyl-naphthalen-1-ylmethyl-amino)-6-fluoro-1,2,3,4-tetrahydro-9H-carbazol-9-yl]-acetate | C35H31N2O4F 564.651 |
| Ethyl (3S)-{6-fluoro-3-[naphthalen-1-ylmethyl-(3-phenyl-propionyl)-amino]-1,2,3,4-tetrahydro-9H-carbazol-9-yl}-acetate | C36H35N2O3F 562.679 |
| Ethyl (3S)-{6-fluoro-3-[((S)-2-methyl-3-phenyl-propionyl)-naphthalen-1-ylmethyl-amino]-1,2,3,4-tetrahydro-9H-carbazol-9-yl}-acetate | C37H37N2O3F 576.706 |
| Ethyl (3S)-(6-fluoro-3-{[3-(2-methoxy-phenyl)-propionyl]-naphthalen-1-ylmethyl-amino}-1,2,3,4-tetrahydro-9H-carbazol-9-yl)-acetate | C37H37N2O4F 592.705 |
| Ethyl (3S)-{3-[(3,3-diphenyl-propionyl)-naphthalen-1-ylmethyl-amino]-6-fluoro-1,2,3,4-tetrahydro-9H-carbazol-9-yl}-acetate | C42H39N2O3F 638.777 |
| Ethyl (3S)-[3-(acetyl-naphthalen-1-ylmethyl-amino)-6-fluoro-1,2,3,4-tetrahydro-9H-carbazol-9-yl]-acetate | C29H29N2O3F 472.555 |
| Ethyl (3S)-[6-fluoro-3-(naphthalen-1-ylmethyl-propionyl-amino)-1,2,3,4-tetrahydro-9H-carbazol-9-yl]-acetate | C30H31N2O3F 486.581 |
| Ethyl (3S)-{6-fluoro-3-[3-phenyl-4-([1,3,4]thiadiazol-2-ylcarbamoyl)-butyrylamino]-1,2,3,4-tetrahydro-9H-carbazol-9-yl}-acetate | C29H30FN5O4S 563.64 |
| Ethyl (3S)-[6-fluoro-3-(3-thiophen-2-yl-propionylamino)-1,2,3,4-tetrahydro-9H-carbazol-9-yl]-acetate | C23H25FN2O3S 428.012 |
| Ethyl (3S)-{3-[3-(3-chloro-isoxazol-5-yl)-propionylamino]-6-fluoro-1,2,3,4-tetrahydro-9H-carbazol-9-yl}-acetate | C22H23ClFN3O4 447.88 |
| Ethyl (3S)-[6-Fluoro-3-(3-pyrimidin-2-yl-propionylamino)-1,2,3,4-tetrahydro-9H-carbazol-9-yl]-acetate | C23H25FN4O3 424.46 |
| Ethyl (3S)-(3-{acetyl-[2-(2-fluoro-phenyl)-ethyl]-amino}-6-fluoro-1,2,3,4-tetrahydro-9H-carbazol-9-yl)-acetate | C26H28F2N2O3 454.51 |
| Ethyl (3S)-(3-{acetyl-[2-(3-fluoro-phenyl)-ethyl]-amino}-6-fluoro-1,2,3,4-tetrahydro-9H-carbazol-9-yl)-acetate | C26H28F2N2O3 454.51 |
| Ethyl (3S)-(3-{cyclohexylmethyl-[3-(2-methoxy-phenyl)-propionyl]-amino}-6-fluoro-1,2,3,4-tetrahydro-9H-carbazol-9-yl)-acetate | C33H41N2O4F 548.693 |

General Method for the Preparation of Intermediates of Structure 1, Wherein $R^4$ Represents $C_{1-5}$-Alkyl or Allyl To a stirred and degassed solution of an appropriately protected ethyl (3-amino-8-bromo-1,2,3,4-tetrahydro-9H-carbazol-9-yl)-acetate derivative of Structure 2c (0.2 mmol) and Pd(PPh$_3$)$_4$ (0.02 mmol, 0.1 eq.) in dry DMF (1.5 ml) is added under inert atmosphere the appropriate tetraC$_{1-5}$-alkyltin or allyltrialkyltin, respectively (0.22 mmol, 1.1 eq.). The reaction mixture is allowed to stir overnight at 110° C. After cooling to rt, acetonitrile (1 ml) and heptane (1 ml) are added. The acetonitrile-DMF phase is washed three times with heptane. Water is then added and the resulting aq. phase is extracted twice with AcOEt. The combined org. phases are washed with brine and dried over Na$_2$SO$_4$. Evaporation of the solvent in vaccuo yields the protected ethyl (3-amino-8-C$_{1-5}$-alkyl-1,2,3,4-tetrahydro-9H-carbazol-9-yl)-acetate derivative or ethyl (3-amino-8-allyl-1,2,3,4-tetrahydro-9H-carbazol-9-yl)-acetate derivative of Structure 1, respectively.

Intermediates of Structure 1 wherein $R^4$ represents $C_{1-5}$-alkyl or allyl:

Ethyl (3S)-(3-benzyloxycarbonylamino-6-fluoro-8-methyl-1,2,3,4-tetrahydro-9H-carbazol-9-yl)-acetate is obtained in quantative yield as a yellow oil. $t_R$=1.09 min (LC-3), ESI-MS (pos.): m/z 439.15 [M+H]$^+$.

Ethyl (3S)-(3-benzyloxycarbonylamino-6-fluoro-8-allyl-1,2,3,4-tetrahydro-9H-carbazol-9-yl)-acetate is obtained in quantative yield as a yellow oil. $t_R$=1.11 min (LC-3), ESI-MS (pos.): m/z 465.22 [M+H]$^+$.

General Method for the Preparation of Intermediates of Structure 1 Wherein $R^4$ Represents Vinyl A suspension of an appropriately protected ethyl (3-amino-8-bromo-1,2,3,4-tetrahydro-9H-carbazol-9-yl)-acetate derivative of Structure 2c (0.4 mmol), vinylboronic anhydride pyridine complex (0.22 mmol, 0.56 eq.), Pd(PPh$_3$)$_4$ (23 mg, 0.02 mmol, 0.05 eq.), and K$_2$CO$_3$ (55 mg, 0.4 mmol, 1 eq.) in 1 ml (DME/H$_2$O) is stirred for 4 h at reflux. Water is added and the resulting aq. phase is extracted three times with AcOEt. The combined org. phases are dried over Na$_2$SO$_4$, filtered and concentrated in vaccuo. The crude product is purified by FC (heptane/AcOEt, 3:1) to yield protected ethyl (3-amino-8-vinyl-1,2,3,4-tetrahydro-9H-carbazol-9-yl)-acetate derivatives of Structure 1.

Intermediate of Structure 1 wherein $R^4$ represents vinyl:

Ethyl (3S)-(3-benzyloxycarbonylamino-6-fluoro-8-vinyl-1,2,3,4-tetrahydro-9H-carbazol-9-yl)-acetate is obtained in 87% yield as a white solid. $t_R$=1.11 min (LC-3), ESI-MS (pos.): m/z 451.19 [M+H]$^+$.

General Method for the Preparation of Intermediates of Structure 1 Wherein $R^4$ Represents $C_{1-6}$-alkylsulfonyl A solution of an appropriately protected ethyl (3-amino-8-bromo-1,2,3,4-tetrahydro-9H-carbazol-9-yl)-acetate derivative of Structure 2c (0.238 mmol), cuprous iodide (204 mg, 1.073 mmol, 4.5 eq.) and sodium methanesulfinate (129 mg, 1.073 mmol, 4.5 eq.) in degassed NMP (5 ml) is heated under inert atmosphere at 140° C. overnight. Then, the mixture is diluted with heptane (5 ml) and AcOEt (5 ml) and filtered over a pad of silica gel with AcOEt as eluent. The solvent is removed in vaccuo and the residue dissolved in AcOEt and H$_2$O. The phases are separated and the aq. phase is extracted twice with AcOEt. The combined org. phases are washed with brine and H$_2$O, dried over Na$_2$SO$_4$ and concentrated in vacuuo to yield the corresponding ethyl (3-amino-8-methanesulfonyl-1,2,3,4-tetrahydro-9H-carbazol-9-yl)-acetate derivative of Structure 1.

Intermediate of Structure 1 wherein $R^4$ represents $C_{1-6}$-alkylsulfonyl:

Ethyl (3RS)-(3-benzyloxycarbonylamino-6-fluoro-8-methanesulfonyl-1,2,3,4-tetrahydro-9H-carbazol-9-yl)-acetate is obtained in quantitative yield as a brown solid. $t_R$=1.04 min (LC-3), ESI-MS (pos.): m/z 503.12 [M+H]$^+$.

General Methods for the Preparation of Intermediates of Structure 2a

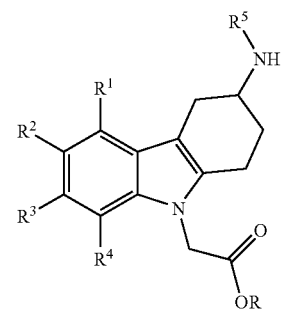

Structure 2a: $R^5 \neq H$
2b: $R^5 = H$

Method (A)

Step A) 4-Nitro-benzenesulfonylation of an Intermediate of Structure 2b to Yield an ethyl [3-(4-nitro-benzenesulfonylamino)-1,2,3,4-tetrahydro-9H-carbazol-9-yl]-acetate Derivative of Structure 3a A catalytical amount of DMAP and p-nitrobenzenesulfonyl chloride (223 mg, 1.01 mmol) are added to an ice cold stirred solution of the appropriate (3-amino-1,2,3,4-tetrahydro-9H-carbazol-9-yl)-acetate derivative hydrochloride of Structure 2b (0.92 mmol) and pyridine (0.96 ml, 11.9 mmol) in DCM. The reaction mixture is allowed to warm up to rt and is continued to stir overnight. The reaction is then quenched by addition of $H_2O$ and sat. $NaHCO_3$ solution. After phase separation the aq. phase is extracted with DCM. The combined org. phases are dried over $Na_2SO_4$, filtered, and the solvent is evaporated to dryness. The crude product is filtered through a plug of silica gel (heptane/AcOEt, 2:1) to give the desired intermediate of Structure 3a.

Intermediate of Structure 3a: Ethyl (3S)-[6-fluoro-3-(4-nitro-benzenesulfonylamino)-1,2,3,4-tetrahydro-9H-carbazol-9-yl]-acetate is obtained in 71% yield as a yellow solid: $t_R$=1.05 min (LC-3), ESI-MS (pos.): m/z 476.12 $[M+H]^+$.

Step B) N-Substitution of a 4-nitro-benzenesulfonamide Intermediate of Structure 3a to Yield Intermediates of Structure 3b Following a procedure described in the literature (Peña, C. et al. *Tetrahedron Lett.* 2005, 46, 2783-2787), a stirred suspension of the appropriate intermediate of Structure 3a (0.21 mmol), $K_2CO_3$ (291 mg, 2.1 mmol) and tetrabutylammonium bromide (6.78 mg, 0.021 mmol) in toluene (2 ml) is heated at 70° C. for 30 min before adding the corresponding alkylating agent $R^5$-L (0.841 mmol). The reaction mixture is continued to stir at 70° C. overnight, cooled to rt, and treated with sat. $NH_4Cl$ solution. After phase separation, the aq. layer is extracted three times with DCM. The combined org. phases are dried over $Na_2SO_4$, filtered, and the solvent evaporated to dryness, affording the corresponding intermediate of Structure 3b in quantitative yield.

Listed in Table 5 below are intermediates of Structure 3b, prepared according to the above-mentioned method.

TABLE 5

| Intermediates of Structure 3b | Formula MW | $t_R$ [min] Meth. | MS Data m/z $[M + H]^+$ |
|---|---|---|---|
| Ethyl (3S)-{6-fluoro-3-[methyl-(4-nitro-benzenesulfonyl)-amino]-1,2,3,4-tetrahydro-9H-carbazol-9-yl}-acetate | C23H24N3O6F 489.52 | 1.09 (LC-3) | 490.05 |
| Ethyl (3S)-{6-fluoro-3-[ethyl-(4-nitro-benzenesulfonyl)-amino]-1,2,3,4-tetrahydro-9H-carbazol-9-yl}-acetate | C24H26N3O6FS 503.549 | 1.11 LC-3 | 504.15 |
| Ethyl (3S)-{6-fluoro-3-[propyl-(4-nitro-benzenesulfonyl)-amino]-1,2,3,4-tetrahydro-9H-carbazol-9-yl}-acetate | C25H28N3O6FS 517.576 | 1.13 LC-3 | 518.23 |

Listed in Table 5a below are further intermediates of Structure 3b, prepared according to the above-mentioned method.

TABLE 5a

| Intermediates of Structure 3b | Formula MW | $t_R$ [min] Method | MS Data m/z $[M + H]^+$ |
|---|---|---|---|
| Ethyl (3S)-{6-fluoro-3-[(4-nitro-benzenesulfonyl)-(3-phenyl-propyl)-amino]-1,2,3,4-tetrahydro-9H-carbazol-9-yl}-acetate | C31H32N3O6FS 593.674 | 1.16 LC-3 | 594.12 |
| Ethyl (3S){-3-[cyclopropylmethyl-(4-nitro-benzenesulfonyl)-amino]-6-fluoro-1,2,3,4-tetrahydro-9H-carbazol-9-yl}-acetate | C26H28N3O6FS 529.587 | 1.12 LC-3 | 530.02 |
| Ethyl (3S)-(6-fluoro-3-{(4-nitro-benzenesulfonyl)-[2-(3-trifluoromethyl-phenoxy)-ethyl]-amino}-1,2,3,4-tetrahydro-9H-carbazol-9-yl)-acetate | C31H29N3O7F4S 663.643 | 1.17 LC-3 | 664.17 |
| Ethyl (3S)-{6-fluoro-3-[(4-nitro-benzenesulfonyl)-(2-phenoxy-ethyl)-amino]-1,2,3,4-tetrahydro-9H-carbazol-9-yl}-acetate | C30H30N3O7FS 595.646 | 1.14 LC-3 | 596.18 |
| Ethyl (3S)-{6-fluoro-3-[(2-methoxy-ethyl)-(4-nitro-benzenesulfonyl)-amino]-1,2,3,4-tetrahydro-9H-carbazol-9-yl}-acetate | C25H28N3O7FS 533.575 | 1.09 LC-3 | 534.16 |

Step C) Cleavage of the 4-nitro-benzenesulfonyl Group to Yield an Intermediate of Structure 2a In analogy to the literature (Miller, S. C.; Scanlan, T. S. *J. Am. Chem. Soc.* 1997, 119, 2301-2302), mercaptoacetic acid (0.019 ml, 0.267 mmol) and DBU (0.081 ml, 0.53 mmol) are added to a stirred solution of an intermediate of Structure 3b (0.179 mmol) in dry DMF (2 ml). The reaction mixture is allowed to stir overnight, then, at rt, sat. $Na_2CO_3$ solution, $H_2O$ and DCM are added. After phase separation, the org. layer is extracted twice with sat. $Na_2CO_3$ solution, and twice with $H_2O$. The combined org. phases are washed with brine and dried over $Na_2SO_4$. After filtration, the solvent is evaporated and the residue is purified by preparative tlc on silica gel (DCM/MeOH/$NH_4OH$, 90:10:1) to give the desired intermediate of Structure 2a in 30-40% yield.

Listed in Table 6 below are intermediates of Structure 2a, prepared according to the above-mentioned method.

TABLE 6

| Intermediates of Structure 2a | Formula MW | $t_R$ [min] Method | MS Data m/z [M + H]$^+$ |
| --- | --- | --- | --- |
| Ethyl (3S)-(6-fluoro-3-methylamino-1,2,3,4-tetrahydro-9H-carbazol-9-yl)-acetate | C17H21FN2O2 304.36 | 0.76 LC-3 | 305.19 |
| Ethyl (3S)-(6-fluoro-3-ethylamino-1,2,3,4-tetrahydro-9H-carbazol-9-yl)-acetate | C18H23FN2O2 318.39 | 0.78 LC-3 | 319.14 |
| Ethyl (3S)-(6-fluoro-3-propylamino-1,2,3,4-tetrahydro-9H-carbazol-9-yl)-acetate | C19H25FN2O2 332.41 | 0.81 LC-3 | 333.15 |

Listed in Table 6a below are further intermediates of Structure 2a, prepared according to the abovementioned method.

TABLE 6a

| Intermediates of Structure 2a | Formula MW | $t_R$ [min] LC-MS Method | MS Data m/z [M + H]$^+$ |
| --- | --- | --- | --- |
| Ethyl (3S)-[6-fluoro-3-(3-phenyl-propylamino)-1,2,3,4-tetrahydro-9H-carbazol-9-yl]-acetate | C25H29N2O2F 408.515 | 0.91 LC-3 | 409.15 |
| Ethyl (3S)-[3-(cyclopropylmethyl-amino)-6-fluoro-1,2,3,4-tetrahydro-9H-carbazol-9-yl]-acetate | C20H25N2O2F 344.428 | 0.82 LC-3 | 345.18 |
| Ethyl (3S)-{6-fluoro-3-[2-(4-trifluoromethyl-phenoxy)-ethylamino]-1,2,3,4-tetrahydro-9H-carbazol-9-yl}-acetate | C25H26N2O3F4 478.484 | 0.95 LC-3 | 479.07 |
| Ethyl (3S)-[6-fluoro-3-(2-phenoxy-ethylamino)-1,2,3,4-tetrahydro-9H-carbazol-9-yl]-acetate | C24H27N2O3F 410.487 | 0.88 LC-3 | 411.10 |
| Ethyl (3S)-[6-fluoro-3-(2-methoxy-ethylamino)-1,2,3,4-tetrahydro-9H-carbazol-9-yl]-acetate | C19H25N2O3F 348.417 | 0.77 LC-3 | 349.15 |

Method (B)

To a stirred suspension of an appropriate ethyl (3-amino-1,2,3,4-tetrahydro-9H-carbazol-9-yl)-acetate derivative hydrochloride of Structure 2b (0.73 mmol) and DIEA (0.769 mmol, 0.132 ml, 1.05 eq.) and the corresponding aldehyde (0.806 mmol, 1.1 eq.) in DCM (10 ml) is added NaBH(OAc)$_3$ (1.62 mmol, 2.2 eq.). The reaction mixture is stirred overnight and diluted with DCM and sat. NaHCO$_3$ solution. The resulting aq. phase is extracted three times with DCM. The combined org. phases are dried over Na$_2$SO$_4$, filtered, and the solvent is evaporated to dryness. The crude product is purified by flash-chromatography on silica gel (DCM/MeOH, 95:5) to give the desired intermediate of Structure 2a in 66 to 95% yield.

Listed in Table 6b below are intermediates of Structure 2a, prepared according to the abovementioned method.

TABLE 6b

| Intermediates of Structure 2a | Formula MW | $t_R$ [min] LC-MS Method | MS Data m/z [M + H]$^+$ |
| --- | --- | --- | --- |
| Ethyl (3S)-(6-fluoro-3-phenethylamino-1,2,3,4-tetrahydro-9H-carbazol-9-yl)-acetate | C24H27N2O2F 394.488 | 0.88 LC-3 | 395.18 |
| Ethyl (3S)-{6-fluoro-3-[(naphthalen-1-ylmethyl)- | C27H27N2O2F | 0.91 | 431.22 |

TABLE 6b-continued

| Intermediates of Structure 2a | Formula MW | $t_R$ [min] LC-MS Method | MS Data m/z $[M + H]^+$ |
|---|---|---|---|
| amino]-1,2,3,4-tetrahydro-9H-carbazol-9-yl}-acetate | 430.521 | LC-3 | |
| Ethyl (3S)-(3-benzylamino-6-fluoro-1,2,3,4-tetrahydro-9H-carbazol-9-yl)-acetate | C23H25N2O2F 380.461 | 0.89 LC-3 | 381.16 |
| Ethyl (3S)-{6-fluoro-3-[2-(2-fluoro-phenyl)-ethylamino]-1,2,3,4-tetrahydro-9H-carbazol-9-yl}-acetate | C24H26N2O2F2 412.478 | 0.88 LC-3 | 413.14 |
| Ethyl (3S)-{6-fluoro-3-[2-(3-fluoro-phenyl)-ethylamino]-1,2,3,4-tetrahydro-9H-carbazol-9-yl}-acetate | C24H26N2O2F2 412.478 | 0.88 LC-3 | 413.14 |
| Ethyl (3S)-[3-(cyclohexylmethyl-amino)-6-fluoro-1,2,3,4-tetrahydro-9H-carbazol-9-yl]-acetate | C23H31N2O2F 386.509 | 0.88 LC-3 | 387.20 |

General Procedures for the Preparation of Intermediates of Structure 2b

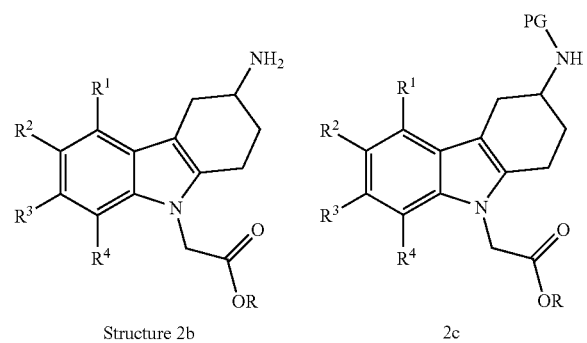

Structure 2b     2c

Cleavage of PG=tert-butoxycarbonyl

To a stirred solution of an ethyl (3-tert-butoxycarbonylamino-1,2,3,4-tetrahydro-9H-carbazol-9-yl)-acetate derivative of Structure 2c (1.61 mmol) in THF (4 ml) is added 2N HCl (2 ml) in diethylether, or in AcOEt. The reaction mixture is stirred overnight, and the formed precipitate is filtered off, rinsed with diethylether and dried to give the desired intermediate of Structure 2b as a white solid in quantitative yield.

Listed in Table 7 below are intermediates of Structure 2b, prepared according to the above-mentioned method, with corresponding intermediate of Structure 2c as starting material.

Cleavage of PG=benzyloxycarbonyl

To a stirred solution of an ethyl (3-benzyloxycarbonylamino-1,2,3,4-tetrahydro-9H-carbazol-9-yl)-acetate derivative of Structure 2c (7.58 mmol) in AcOH (85 ml) and EtOH (20 ml) is added Pd/C (806 mg, 0.76 mmol, 0.1 eq.). The reaction mixture is stirred for 1 h under a $H_2$ atmosphere then diluted with DCM and filtered over a plug of celite. A solution of 4M HCl in dioxane (30 ml, 10 eq.) is added to the filtrate and the solvents are removed in vaccuo to give an intermediate of Structure 2b.

Listed in Table 7a below are further intermediates of Structure 2b, prepared according to the above-mentioned methods, with the corresponding intermediate of Structure 2c as starting material.

TABLE 7a

| Intermediates of Structure 2b | Formula MW | $t_R$ [min] LC-MS Method | MS Data m/z $[M + H]^+$ |
|---|---|---|---|
| Ethyl (3RS)-(3-amino-8-chloro-6-fluoro-1,2,3,4-tetrahydro-carbazol-9-yl)-acetate hydrochloride | C16H19N2O2Cl2F 361.243 | 0.78 LC-3 | 325.05 |
| Ethyl (3RS)-(3-amino-6-fluoro-1,2,3,4-tetrahydro-carbazol-9-yl)-acetate hydrochloride | C20H19N2O2F 338.381 | 1.02 LC-3 | 339.12 |

TABLE 7

| Intermediates of Structure 2b | Formula MW | $t_R$ [min] Method | MS Data m/z $[M + H]^+$ (parent) |
|---|---|---|---|
| Ethyl (3R)-(3-amino-1,2,3,4-tetrahydro-9H-carbazol-9-yl)-acetate hydrochloride | C16H21N2O2Cl 308.807 | 0.74 LC-2 | 273.16 |
| Ethyl (3S)-(3-amino-1,2,3,4-tetrahydro-9H-carbazol-9-yl)-acetate hydrochloride | C16H21N2O2Cl 308.807 | 0.74 LC-2 | 273.16 |
| Ethyl (3R)-(3-amino-6-fluoro-1,2,3,4-tetrahydro-9H-carbazol-9-yl)-acetate hydrochloride | C16H20ClFN2O2 326.79 | 0.74 LC-2 | 291.15 |
| Ethyl (3S)-(3-amino-6-fluoro-1,2,3,4-tetrahydro-9H-carbazol-9-yl)-acetate hydrochloride | C16H20N2O2ClF 326.79 | 0.73 LC-2 | 291.11 |

General Method for the Synthesis of Intermediates of Structure 2c

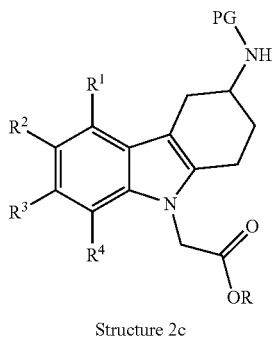

Structure 2c

Alkylation of an Intermediate of Structure 4:

A solution of e.g. ethyl bromoacetate (1.25 ml, 11.25 mmol) in dry DMF (20 ml) is added dropwise to a heated (60° C.) solution of an intermediate of Structure 4 (10.22 mmol) and $Cs_2CO_3$ (9.99 g, 30.67 mmol) in dry DMF (50 ml) over a period of 15 min. The resulting suspension is continued to stir at 60° C. for 1 h, or overnight. After cooled to rt, the reaction mixture is filtered and washed with DCM. The DCM is evaporated and the residue is partitioned between AcOEt and $H_2O$. The aq. layer is extracted three times with AcOEt. The combined org. layers are washed with $H_2O$ and brine, dried over $MgSO_4$ and filtered. The solvent is evaporated and the solid residue is purified by FC with a continuous gradient of eluents from AcOEt/heptane 1:99 to 1:1 to give the desired intermediate of Structure 2c in 40 to 80% yield.

Listed in Table 8 below are intermediates of Structure 2c, prepared according to the above-mentioned method, starting from corresponding intermediate of Structure 4.

TABLE 8

| Intermediates of Structure 2c | Formula MW | $t_R$ [min] LC-MS Method | MS Data m/z $[M + Na]^+$ or $[M + H]^+$ |
|---|---|---|---|
| Ethyl (3R)-(3-tert-butoxycarbonylamino-1,2,3,4-tetrahydro-9H-carbazol-9-yl)-acetate | C21H28N2O4 372.463 | 1.15 LC-2 | 394.95 |
| Ethyl (3S)-(3-tert-butoxycarbonylamino-1,2,3,4-tetrahydro-9H-carbazol-9-yl)-acetate | C21H28N2O4 372.463 | 1.15 LC-2 | 395.15 |
| Ethyl (3R)-(3-tert-butoxycarbonylamino-6-fluoro-1,2,3,4-tetrahydro-9H-carbazol-9-yl)-acetate | C21H27FN2O4 390.45 | 1.15 LC-2 | 413.09 |
| Ethyl (3S)-(3-tert-butoxycarbonylamino-6-fluoro-1,2,3,4-tetrahydro-9H-carbazol-9-yl)-acetate | C21H27FN2O4 390.45 | 1.16 LC-2 | 413.09 |
| Ethyl (3RS)-(3-benzyloxycarbonylamino-8-chloro-5-fluoro-1,2,3,4-tetrahydro-9H-carbazol-9-yl)-acetate | C24H24N2O4ClF 458.916 | 1.11 LC-3 | 458.99 |
| Ethyl (3RS)-(3-benzyloxycarbonylamino-6-fluoro-1,2,3,4-tetrahydro-9H-carbazol-9-yl)-acetate | C24H25N2O4F 424.47 | 1.06 LC-3 | 425.22 |
| Ethyl (3RS)-(3-benzyloxycarbonylamino-8-chloro-6-fluoro-1,2,3,4-tetrahydro-9H-carbazol-9-yl)-acetate | C24H24N2O4ClF 458.916 | 1.11 LC-3 | 459.05 |

Listed in Table 8a below are further intermediates of Structure 2c, prepared according to the above-mentioned method, starting from corresponding intermediate of Structure 4.

TABLE 8a

| Intermediates of Structure 2c | Formula MW | $t_R$ [min] LC-MS Method | MS Data m/z $[M + H]^+$ |
|---|---|---|---|
| Ethyl (3RS)-(3-benzyloxycarbonylamino-6-trifluoromethyl-1,2,3,4-tetrahydro-9H-carbazol-9-yl)-acetate | C25H25N2O4F3 474.478 | 1.11 LC-3 | 475.14 |
| Ethyl (3RS)-(3-benzyloxycarbonylamino-8-bromo-6-fluoro-1,2,3,4-tetrahydro-9H-carbazol-9-yl)-acetate | C24H24N2O4BrF 503.367 | 1.11 LC-3 | 505.11 |
| Ethyl (3S)-(3-benzyloxycarbonylamino-7-chloro-6-fluoro-1,2,3,4-tetrahydro-9H-carbazol-9-yl)-acetate | C24H24ClFN2O4 458.91 | not determined | not determined |

TABLE 8a-continued

| Intermediates of Structure 2c | Formula MW | $t_R$ [min] LC-MS Method | MS Data m/z [M + H]+ |
|---|---|---|---|
| Ethyl (3R)-(3-benzyloxycarbonylamino-8-chloro-1,2,3,4-tetrahydro-9H-carbazol-9-yl)-acetate | C24H25N2O4Cl 440.926 | 1.1 LC-3 | 441.07 |

Listed in Table 9 below are intermediates of Structure 4, prepared in analogy to the procedure described in the literature (Ha, J. D. et al., *Bulletin of the Korean Soc. Chem.* 2004, 25, 1784-1790).

TABLE 9

| Intermediates of Structure 4 | Formula MW | $t_R$ [min] Method | MS Data m/z [M + H]+ |
|---|---|---|---|
| (3RS)-(8-Chloro-5-fluoro-2,3,4,9-tetrahydro-1H-carbazol-3-yl)-carbamic acid benzyl ester | C20H18N2O2ClF 372.825 | 1.07 LC-3 | 373.03 |
| (3RS)-(8-Chloro-6-fluoro-2,3,4,9-tetrahydro-1H-carbazol-3-yl)-carbamic acid benzyl ester | C20H18N2O2ClF 372.825 | 1.06 LC-3 | 372.99 |
| (3RS)-(6-Fluoro-2,3,4,9-tetrahydro-1H-carbazol-3-yl)-carbamic acid benzyl ester | C20H19N2O2F 338.38 | 1.02 LC-3 | 339.12 |

Listed in Table 9a below are further intermediates of Structure 4, prepared according to the abovementioned procedure.

TABLE 9a

| Intermediates of Structure 4 | Formula MW | $t_R$ [min] Method | MS Data m/z [M + H]+ |
|---|---|---|---|
| (3RS)-(6-Trifluoromethyl-2,3,4,9-tetrahydro-1H-carbazol-3-yl)-carbamic acid benzyl ester | C21H19N2O2F3 388.388 | 1.07 LC-3 | 389.08 |
| (3RS)-(8-Bromo-6-fluoro-2,3,4,9-tetrahydro-1H-carbazol-3-yl)-carbamic acid benzyl ester | C20H18N2O2BrF 417.277 | 1.07 LC-3 | 417.03 |
| (3RS)-(7-Chloro-6-fluoro-2,3,4,9-tetrahydro-1H-carbazol-3-yl)-carbamic acid benzyl ester | C20H18N2O2ClF 372.825 | 1.05 LC-3 | 373.07 |
| (3R)-(8-Chloro-2,3,4,9-tetrahydro-1H-carbazol-3-yl)-carbamic acid benzyl ester | C20H19N2O2Cl 354.836 | 1.05 LC-3 | 355.11 |

General Method for the Preparation of Intermediates of Structure 1 from Intermediates of Structure 8a To a solution of the respective amine (0.140 mmol, 1.5 eq.), HATU (0.140 mmol, 1.5 eq.) and DIEA (0.048 ml, 0.280 mmol, 3 eq.) in 0.5 ml (DMF/THF 4:1) is added a solution of an intermediate of Structure 8a in 0.5 ml (DMF/THF 4:1). The reaction mixture is stirred for 20 h, then diluted with DCM and sat. NaHCO$_3$ solution. After stirring for an additional 1 h, H$_2$O is added and the org. phase is separated. The aq. phase is extracted with DCM, the combined org. extracts are concentrated under a stream of air to yield the desired crude intermediate of Structure 1.

Listed in Table 10 below are intermediates of Structure 1, prepared according to the abovementioned method with corresponding intermediate of Structure 8a as starting material.

TABLE 10

| Intermediates of Structure 1 starting from intermediates of Structure 8a | Formula MW | $t_R$ [min] LC-MS Method | MS Data m/z [M + H]+ |
|---|---|---|---|
| Ethyl (3S)-{3-[(RS)-2-benzyl-3-(2-methylbenzyl)-carbamoyl-propionylamino]-6-fluoro-1,2,3,4-tetrahydro-9H-carbazol-9-yl}-acetate | C34H36FN3O4 569.67 | 1.06 LC-3 | 570.21 |
| Ethyl (3S)-{3-[(RS)-2-benzyl-3-(3-methoxy-phenylcarbamoyl)-propionylamino]-6-fluoro-1,2,3,4-tetrahydro-9H-carbazol-9-yl}-acetate | C34H36FN3O5 585.67 | 1.06 LC-3 | 586.21 |
| Ethyl (3S)-{3-[(RS)-2-benzyl-3-(4-chloro-phenylcarbamoyl)-propionylamino]-6-fluoro-1,2,3,4-tetrahydro-9H-carbazol-9-yl}-acetate | C33H33ClFN3O4 590.08 | 1.09 LC-3 | 590.2 |
| Ethyl (3S)-{3-[(RS)-2-benzyl-3-(4-fluoro-benzylcarbamoyl)-propionylamino]-6-fluoro-1,2,3,4-tetrahydro-9H-carbazol-9-yl}-acetate | C34H35F2N3O4 587.66 | 1.05 LC-3 | 588.25 |
| Ethyl [(3S)-3-((RS)-2-benzyl-3-propylcarbamoyl-propionylamino)-6-fluoro-1,2,3,4-tetrahydro-9H-carbazol-9-yl]-acetate | C30H36FN3O4 521.62 | 1 LC-3 | 522.26 |

General Method for the Preparation of Intermediates of Structure 8a from Intermediates of Structure 8b

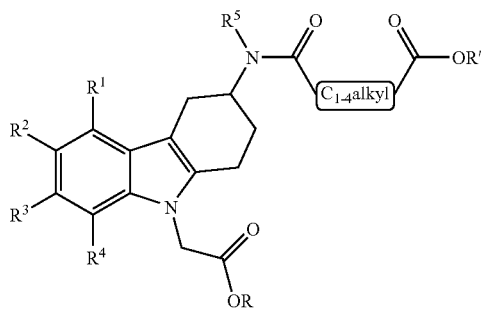

Structure 8a, wherein R' represents H and R represents $C_{1-4}$-alkyl
8b, wherein R' and R independently represent $C_{1-4}$-alkyl A solution of an intermediate of Structure 8b (0.54 mmol) and TFA (0.8 ml, 10 mmol, 20 eq.) in DCM (8 ml) is stirred for 2.5 h. The volatiles are removed under reduced pressure to yield an intermediate of Structure 8a.

Intermediate of Structure 8a: 3-benzyl-N-(9-ethoxycarbonylmethyl-6-fluoro-2,3,4,9-tetrahydro-1H-carbazol-3-yl)-succinamic acid is quantitative yield as light brown foam. $t_R$=0.97 min (LC-3), ESI-MS (pos.): m/z 481.22 [M+H]$^+$.

General Method for the Preparation of Intermediates of Structure 8b from Intermediates of Structure 2a or 2b A solution of an appropriate intermediate of Structure 2a or 2b (2.16 mmol), an appropriate $C_{1-4}$alkanedicarboxylic acid mono-ester of Structure 9 (4.05 mmol, 1.9 eq.), DIEA (1.5 ml, 8.65 mmol, 4 eq.) and HATU (1.64 g, 4.32 mmol, 2 eq.) in 10 ml (DMF/THF, 4:1) is stirred overnight. The reaction mixture is diluted with AcOEt and sat. NaHCO$_3$. The aq. phase is extracted twice with AcOEt. The combined org. extracts are washed with brine, dried over MgSO$_4$, and concentrated in vacuo. The residue is purified by flash-chromatography on silica gel with a gradient of heptane/AcOEt to yield the desired intermediate of Structure 8b.

Intermediate of Structure 8b:
3-Benzyl-N-(9-ethoxycarbonylmethyl-6-fluoro-2,3,4,9-tetrahydro-1H-carbazol-3-yl)-succinamic acid tent-butyl ester is obtained in 25% yield as an orange oil: $t_R$=1.10 min (LC-3), ESI-MS (pos.): m/z 537.28 [M+H]$^+$.

Starting Materials:
Starting Materials of Structure 4:
(3R)-(2,3,4,9-tetrahydro-1H-carbazol-3-yl)-carbamic acid 1,1-dimethylethyl ester,
(3S)-(2,3,4,9-tetrahydro-1H-carbazol-3-yl)-carb amic acid 1,1-dimethylethyl ester,
(3R)-(6-fluoro-2,3,4,9-tetrahydro-1H-carbazol-3-yl)-carb amic acid 1,1-dimethylethyl ester, and
(3S)-(6-fluoro-2,3,4,9-tetrahydro-1H-carbazol-3-yl)-carb amic acid 1,1-dimethylethyl ester; as well as
Starting Materials of Structure 7:
(3R)-(2,3,4,9-tetrahydro-1H-carbazol-3-ylamine),
(3S)-(2,3,4,9-tetrahydro-1H-carbazol-3-ylamine),
(3R)-(6-fluoro-2,3,4,9-tetrahydro-1H-carbazol-3-ylamine), and
(3S)-(6-fluoro-2,3,4,9-tetrahydro-1H-carbazol-3-ylamine),
are prepared according to literature procedures (Rosentreter U. et al., Arzneim.-Forsch. 1989, 39(12), 1519-1521); EP 0242518; Ha J. D. et al., Bulletin of the Korean Soc. Chem. 2004, 25, 1784-1790; WO 03/033099).

Starting Materials of Structure 9:
Starting materials of Structure 9 are commercially available or synthesized according to well known methods (see for example: J. Org. Chem. 1986, 51(6), 938-940).

NMR data of selected compounds are given in Table 11 below.

TABLE 11

| Compound | Chemical shifts (δ) in parts per million (ppm) | Solvent |
|---|---|---|
| (3S)-[3-(3-Cyclopentyl-propionylamino)-1,2,3,4-tetrahydro-9H-carbazol-9-yl]-acetic acid | 0.99 (br.s, 2H), 1.41-1.64 (m, 9H), 1.98 (m, 2H), 2.06 (t, 2H), 2.48-2.72 (m, 4H), 2.99 (m, 1H), 4.33 (m, 1H), 4.63 (s, 2H), 6.03 (d, 1H), 6.94-7.14 (m, 3H), 7.32 (d, 2H). | CDCl$_3$ |
| (3RS)-[3-(3-Benzyl-ureido)-6-fluoro-1,2,3,4-tetrahydro-9H-carbazol-9-yl]-acetic acid | 1.78 (m, 1H), 2.02 (m, 1H), 2.48 (m, 1H), 2.69 (m, 2H), 2.92 (dd, 1H), 3.93 (m, 1H), 4.23 (m, 2H), 4.86 (d, 2H), 6.09 (d, 1H), 6.30 (t, 1H), 6.88 (td, 1H), 7.15 (dd, 1H), 7.24 (m, 3H), 7.32 (m, 3H) | DMSO-d$_6$ |
| (3S)-{6-Fluoro-3-[3-(4-isopropyl-phenyl)-propionylamino]-1,2,3,4-tetrahydro-9H-carbazol-9-yl}-acetic acid | 1.19 (d, 6H), 1.73 (m, 1H), 1.97 (m, 1H), 2.38 (t, 2H), 2.36-2.45 (m, 1H), 2.70 (m, 2H), 2.80 (t, 2H), 2.82-2.90 (m, 2H), 4.01 (m, 1H), 4.87 (m, 2H), 6.88 (dt, 1H), 7.01 (m, 4H), 7.33 (dd, 1H), 7.93 (d, 1H), 12.90 (bs, 1H) | DMSO-d$_6$ |
| (3S)-(6-Fluoro-3-{(2RS)-2-[(4-fluoro-phenylcarbamoyl)-methyl]-3-phenyl-propionylamino}-1,2,3,4-tetrahydro-9H-carbazol-9-yl)-acetic acid | 1.59 (m, 0.5H), 1.74 (m, 1H), 1.91 (m, 0.5H), 2.32 (m, 2H), 2.68 (m, 4H), 2.90 (m, 1H), 3.08 (m, 1H), 3.57 (m, 1H), 3.95 (m, 1H), 4.84 (m, 2H), 6.87 (m, 1H), 6.97 (d, 0.5H), 7.10 (m, 2.5H), 7.21 (m, 3H), 7.30 (m, 3H), 7.60 (m, 2H), 7.97 (t, 1H), 9.99 (d, 1H), 13.00 (br.s, 1H) | DMSO-d$_6$ |
| (3S)-[3-(Benzyloxycarbonyl-cyclopropylmethyl-amino)-6-fluoro-1,2,3,4-tetrahydro-9H-carbazol-9-yl]-acetic acid | 0.26 (m, 2H), 0.47 (d, 2H), 1.07 (m, 1H), 2.05 (m, 1H), 2.18 (m, 1H), 2.82 (m, 2H), 3.21 (d, 2H), 4.10 (m, 1H), 4.88 (s, 2H), 5.14 (s, 2H), 6.88 (t, 1H), 7.19 (d, 1H), 7.45 (m, 6H), 12.90 (br.s, 1H). | DMSO-d$_6$ |
| (3S)-{3-[Benzyloxycarbonyl-(2- | 2.06 (m, 2H), 2.77 (m, 6H), 3.29 (m, 2H), 3.45 (m, 3H), 4.08 (dd, 1H), 4.88 (m, 2H), 5.13 (s, 2H), | DMSO-d$_6$ |

TABLE 11-continued

| Compound | Chemical shifts (δ) in parts per million (ppm) | Solvent |
|---|---|---|
| methoxy-ethyl)-amino]-6-fluoro-1,2,3,4-tetrahydro-9H-carbazol-9-yl}-acetic acid | 6.89 (m, 1H), 7.16 (m, 1H), 7.34 (m, 6H), 13.00 (br. s, 1H). | |
| (3S)-{6-Fluoro-3-[[3-(2-methoxy-phenyl)-propionyl]-(2-phenoxy-ethyl)-amino]-1,2,3,4-tetrahydro-9H-carbazol-9-yl}-acetic acid | 1.93 (dd, 1H), 2.09 (m, 1H), 2.75 (m, 8H), 3.66 (m, 3H), 3.77 (m, 2H), 4.13 (m, 3H), 4.90 (m, 2H), 6.90 (m, 6H), 7.17 (m, 3H), 7.33 (m, 3H), 12.90 (br. s, 1H) | DMSO-$d_6$ |
| (3S)-{6-Fluoro-3-[naphthalen-1-ylmethyl-(3-phenyl-propionyl)-amino]-1,2,3,4-tetrahydro-9H-carbazol-9-yl}-acetic acid | 1.93 (m, 2H), 2.70-3.08 (m, 8H), 4.41 (m, 0.5H), 4.86 (m, 2.5H), 5.05 (m, 2H), 6.87 (m, 1H), 7.04 (m, 2H), 7.19 (m, 3H), 7.35 (m, 3H), 7.56 (m, 3H), 7.83 (m, 1H), 7.97 (m, 1H), 8.15 (m, 1H), 13.00 (br.s, 1H). | DMSO-$d_6$ |
| (3RS)-(3-Benzyloxycarbonylamino-6-fluoro-1,2,3,4-tetrahydro-9H-carbazol-9-yl)-acetic acid | 1.76 (m, 1H), 2.05 (m, 1H), 2.48 (m, 1H), 2.68 (m, 1H), 2.75 (t, 1H), 2.93 (d, 1H), 3.77 (m, 1H), 4.85 (s, 2H), 5.05 (s, 2H), 6.87 (dt, 1H), 7.14 (dd, 1H), 7.29-7.38 (m, 5H), 7.46 (m, 1H). | DMSO-$d_6$ |
| (3S)-Ethyl [3-(3-butyl-ureido)-1,2,3,4-tetrahydro-9H-carbazol-9-yl]-acetate | 0.86 (t, 3H), 1.20 (t, 3H), 1.31 (m, 2H), 1.42 (m, 2H), 2.06 (m, 2H), 2.64 (dd, 1H), 2.70 (m, 2H), 3.03-3.10 (m, 3H), 4.18 (q, 2H), 4.28 (m, 1H), 4.71 (s, 2H), 7.04-7.21 (m, 3H), 7.45 (d, 1H). | DMSO-$d_6$ |
| (3S)-Ethyl (3-propoxycarbonylamino-1,2,3,4-tetrahydro-9H-carbazol-9-yl)-acetate | 0.93 (t, 3H), 1.24 (t, 3H), 1.63 (m, 2H), 2.03-2.14 (m, 2H), 2.65 (dd, 1H), 2.77 (t, 2H), 3.12 (dd, 1H), 4.02 (t, 2H), 4.20 (m, 4H), 4.72 (s, 2H), 7.07-7.14 (m, 1H,H), 7.17 (m, 2H), 7.44 (d, 1H). | CDCl$_3$ |
| (3S)-Ethyl [3-(2-phenoxy-acetylamino)-1,2,3,4-tetrahydro-9H-carbazol-9-yl]-acetate | 1.24 (t, 3H), 2.04 (m, 1H), 2.17 (m, 1H), 2.60-2.86 (m, 3H), 3.15 (dd, 1H), 4.20 (q, 2H), 4.53 (m, 1H), 4.49 (s, 2H), 4.72 (s, 2H), 6.71 (d, 1H), 6.90 (s, 2H), 7.02-7.27 (m, 6H), 7.45 (d, 1H). | CDCl$_3$ |
| (3R)-Ethyl (3-tert-butoxycarbonylamino-1,2,3,4-tetrahydro-9H-carbazol-9-yl)-acetate | 1.25 (t, 3H), 1.45 (s, 9H), 1.99 (m, 1H), 2.12 (m, 1H), 2.63 (dd, 1H,), 2.75 (m, 2H), 3.09 (dd, 1H), 4.16 (m, 1H), 4.21 (d, 2H), 4.72 (s, 2H), 7.18 (m, 3H), 7.45 (d, 1H). | CDCl$_3$ |
| (3R)-Ethyl {6-fluoro-3-[2-(4-trifluoromethyl-phenyl)-acetylamino]-1,2,3,4-tetrahydro-9H-carbazol-9-yl}-acetate | 1.24 (t, 3H), 2.04 (m, 2H), 2.60 (m, 2H), 2.70 (dt, 1H), 3.01 (dd, 1H), 3.54 (s, 2H), 4.19 (q, 2H), 4.43 (m, 1H), 4.66 (s, 2H), 5.58 (d, 1H), 6.88 (dt, 1H), 7.06 (m, 2H), 7.27 (m, 1H), 7.39 (d, 2H), 7.54 (d, 2H). | CDCl$_3$ |
| (3RS)-Ethyl (3-benzyloxycarbonylamino-8-chloro-6-fluoro-1,2,3,4-tetrahydro-9H-carbazol-9-yl)-acetate | 1.18 (t, 3H), 1.76 (m, 1H), 2.03 (m, 1H), 2.46 (m, 1H), 2.63-2.80 (m, 2H), 2.90 (dd, 1H), 3.75 (m, 1H), 4.14 (q, 2H), 5.03 (s, 2H), 5.15 (s, 2H), 7.01 (dd, 1H), 7.19 (dd, 1H), 7.27-7.36 (m, 5), 7.45 (d, 1H). | DMSO-$d_6$ |
| (3S)-Ethyl [6-fluoro-3-(4-nitro-benzenesulfonylamino)-1,2,3,4-tetrahydro-9H-carbazol-9-yl]-acetate | 1.28 (t, 3H), 2.07 (dd, 2H), 2.54 (dd, 1H), 2.73 (t, 2H), 2.87 (dd, 1H), 3.94 (m, 1H), 4.21 (d, 2H), 4.68 (s, 2H), 4.90 (d, 1H), 6.85-6.94 (m, 2H), 7.06 (dd, 1H), 8.03 (d, 1H), 8.30 (d, 1H). | CDCl$_3$ |
| (3S)-Ethyl {6-fluoro-3-[methyl-(4-nitro-benzenesulfonyl)-amino]-1,2,3,4-tetrahydro-9H-carbazol-9-yl}-acetate | 1.27 (t, 3H), 1.85 (m, 1H), 2.01 (m, 1H), 2.65 (dd, 1H), 2.75-2.82 (m, 3H), 2.94 (s, 3H), 4.20 (d, 2H), 4.36 (m, 1H), 4.67 (s, 2H), 6.90 (dt, 1H), 6.97 (dd, 1H), 7.06 (dd, 1H), 8.03 (d, 1H), 8.37 (d, 1H). | CDCl$_3$ |
| (3RS)-(8-Chloro-6-fluoro-2,3,4,9-tetrahydro-1H-carbazol-3-yl)-carbamic acid benzyl ester | 1.76 (m, 1H), 1.99 (m, 1H), 2.48 (m, 1H), 2.74-2.93 (m, 3H), 3.80 (m, 1H), 5.03 (s, 2H), 7.00 (dd, 1H), 7.10 (dd, 1H), 7.28-7.36 (m, 5H), 7.43 (d, 1H), 11.10 (s, 1H). | DMSO-$d_6$ |

Biological Assays:
Preparation of hCRTH2 Receptor Membranes and Radioligand Binding Assay:

Preparation of the Membranes and Radioligand Binding Assays are Performed According to known procedures (e.g. Sawyer N. et al., Br. J. Pharmacol. 2002, 137, 1163-1172). A clonal HEK 293 cell line, expressing high level of recombinant hCRTH2 receptor, is selected for the preparation of membranes. Cells are detached from culture plates in 5 ml buffer A per plate (5 mM Tris, pH 7.4, 1 mM MgCl$_2$, 0.1 mM PMSF, 0.1 mM phenanthroline) using a police rubber and transferred into centrifugation tubes and frozen at −80° C. After thawing, the cells are centrifuged at 500 g for 5 min and then resuspended in buffer A. Cells are then fragmented by homogenization with a Polytron cell homogenizer for 30 s. The membrane fragments are collected by centrifugation at 3000 g for 40 min and resuspended in buffer B (50 mM Tris, pH 7.4, 25 mM MgCl$_2$, 250 mM saccharose) and aliquots are stored at ±20° C.

Binding assay is performed in a total volume of 250 μl. In each well, 75 μl buffer C (50 mM Tris, pH 7.4, 100 mM NaCl, 1 mM EDTA, 0.1% BSA (protease free), 0.01% NaN$_3$) is mixed with 50 μl {$^3$H}-PGD$_2$ (2.5 nM, 220,000 dpm/well, Amersham Biosciences, TRK734), 100 μl CRTH2 membranes to give 80 μg per well, and 25 μl of test compound in buffer C containing 1% DMSO. For unspecific binding, PGD$_2$ is added to the reaction mixture at 1 µM final concentration. This binding assay mix is incubated at rt for 90 min and then filtered through a GF/C filter plate. The filter is washed three times with ice cold binding buffer C. Then, Microscint-40 (Packard, 40 µl/well) is added and the receptor bound radioactivity is quantified by scintillation counting in a "TopCount" benchtop microplate scintillation counter (Packard).

Results for Ligand Binding to the hCRTH2 Receptor:

Antagonistic activities (IC$_{50}$ values) of compounds of Formula I are in the range of 0.1 to 10000 nM with respect to the hCRTH2 receptor (preferred compounds: <1000 nM, more preferred compounds: <100 nM, most preferred compounds: <10 nM). IC$_{50}$ values of 242 from 251 exemplified compounds (9 IC$_{50}$ values being not available) are in the range of 0.4-2050 nM with an average of 97 nM with respect to the hCRTH2 receptor. Antagonistic activities of selected compounds are displayed in Table 12.

TABLE 12

| Compound | hCRTH2 Bdg IC$_{50}$ (nM) |
| --- | --- |
| (3S)-[3-(3,3-Diphenyl-propionylamino)-6-fluoro-1,2,3,4-tetrahydro-9H-carbazol-9-yl]-acetic acid | 2 |
| (3S)-(3-{Acetyl-[2-(2-fluoro-phenyl)-ethyl]-amino}-6-fluoro-1,2,3,4-tetrahydro-9H-carbazol-9-yl)-acetic acid | 4 |
| (3S)-(6-Fluoro-3-{(2-methoxy-ethyl)-[3-(2-methoxy-phenyl)-propionyl]-amino}-1,2,3,4-tetrahydro-9H-carbazol-9-yl)-acetic acid | 6 |
| (3S)-{3-[(RS)-2-Benzyl-3-(3-methoxy-phenylcarbamoyl)-propionylamino]-6-fluoro-1,2,3,4-tetrahydro-9H-carbazol-9-yl}-acetic acid | 6 |
| (3S)-[3-(3-Benzyl-1-cyclohexylmethyl-ureido)-6-fluoro-1,2,3,4-tetrahydro-9H-carbazol-9-yl]-acetic acid | 6 |
| (3S)-{3-[2-(4-Chloro-phenoxy)-acetylamino]-6-fluoro-1,2,3,4-tetrahydro-9H-carbazol-9-yl}-acetic acid | 9 |
| (3S)-{3-[(2,3-Dihydro-1H-indole-2-carbonyl)-amino]-6-fluoro-1,2,3,4-tetrahydro-9H-carbazol-9-yl}-acetic acid | 11 |
| (3S)-{6-Fluoro-3-[3-(4-methylsulfanyl-phenyl)-propionylamino]-1,2,3,4-tetrahydro-9H-carbazol-9-yl}-acetic acid | 14 |
| (3S)-{3-[3-(2,5-Bis-trifluoromethyl-phenyl)-propionylamino]-6-fluoro-1,2,3,4-tetrahydro-9H-carbazol-9-yl}-acetic acid | 15 |
| (3S)-[3-(3-Benzo[1,3]dioxol-5-yl-propionylamino)-6-fluoro-1,2,3,4-tetrahydro-9H-carbazol-9-yl]-acetic acid | 15 |
| (3S)-{6-Fluoro-3-[ethyl-(3-phenyl-propionyl)-amino]-1,2,3,4-tetrahydro-9H-carbazol-9-yl}-acetic acid | 16 |
| (3S)-{3-[3-(2,4-Dichloro-phenyl)-propionylamino]-6-fluoro-1,2,3,4-tetrahydro-9H-carbazol-9-yl}-acetic acid | 16 |
| (3S)-(6-Fluoro-3-{[(2RS)-8-methoxy-1,2,3,4-tetrahydro-naphthalene-2-carbonyl]-amino}-1,2,3,4-tetrahydro-9H-carbazol-9-yl)-acetic acid | 18 |
| (3S)-{6-Fluoro-3-[((S)-2-methyl-3-phenyl-propionyl)-(2-phenoxy-ethyl)-amino]-1,2,3,4-tetrahydro-9H-carbazol-9-yl}-acetic acid | 21 |
| (3RS)-(3-Benzyloxycarbonylamino-6-trifluoromethyl-1,2,3,4-tetrahydro-9H-carbazol-9-yl)-acetic acid | 26 |
| (3S)-{6-Fluoro-3-[3-(2-hydroxy-phenyl)-propionylamino]-1,2,3,4-tetrahydro-9H-carbazol-9-yl}-acetic acid | 33 |
| (3R)-{3-[3-(3-Chloro-phenyl)-propionylamino]-6-fluoro-1,2,3,4-tetrahydro-9H-carbazol-9-yl}-acetic acid | 39 |
| (3S)-{6-Fluoro-3-[3-(3-trifluoromethoxy-phenyl)-propionylamino]-1,2,3,4-tetrahydro-9H-carbazol-9-yl}-acetic acid | 47 |
| (3RS)-[8-Chloro-6-fluoro-3-(3-phenyl-propionylamino)-1,2,3,4-tetrahydro-9H-carbazol-9-yl]-acetic acid | 57 |
| (3S)-{3-[(2-Benzyloxy-acetyl)-methyl-amino]-6-fluoro-1,2,3,4-tetrahydro-9H-carbazol-9-yl}-acetic acid | 60 |
| (3R)-[6-Fluoro-3-(3-p-tolyl-propionylamino)-1,2,3,4-tetrahydro-9H-carbazol-9-yl]-acetic acid | 61 |
| (3S)-{6-Fluoro-3-[3-(4-methanesulfonyl-phenyl)-propionylamino]-1,2,3,4-tetrahydro-9H-carbazol-9-yl}-acetic acid | 72 |
| (3S)-(3-Isobutoxycarbonylamino-1,2,3,4-tetrahydro-9H-carbazol-9-yl)-acetic acid | 84 |
| (3S)-{3-[3-(3-tert-Butoxycarbonylamino-phenyl)-propionylamino]-6-fluoro-1,2,3,4-tetrahydro-9H-carbazol-9-yl}-acetic acid | 93 |
| (3S)-[3-(2-Benzyloxy-ethoxycarbonylamino)-1,2,3,4-tetrahydro-9H-carbazol-9-yl]-acetic acid | 117 |
| (3R)-[3-(3-Phenylsulfonyl-ureido)-1,2,3,4-tetrahydro-9H-carbazol-9-yl]-acetic acid | 147 |
| (3R)-[3-(3-Naphthalen-1-yl-ureido)-1,2,3,4-tetrahydro-9H-carbazol-9-yl]-acetic acid | 152 |
| (3R)-[3-(2-Thiophen-2-yl-acetylamino)-1,2,3,4-tetrahydro-9H-carbazol-9-yl]-acetic acid | 297 |
| (3R)-[3-(3-Cyclopentyl-propionylamino)-1,2,3,4-tetrahydro-9H-carbazol-9-yl]-acetic acid | 400 |
| (3R)-(3-Benzoylamino-1,2,3,4-tetrahydro-9H-carbazol-9-yl)-acetic acid | 488 |
| (3S)-{6-Fluoro-3-[(1H-indole-2-carbonyl)-amino]-1,2,3,4-tetrahydro-9H-carbazol-9-yl}-acetic acid | 824 |
| (3S)-[3-(3-Butyl-ureido)-1,2,3,4-tetrahydro-9H-carbazol-9-yl]-acetic acid | 896 |

Intracellular Calcium Mobilization Assay (FLIPR):

Cells (HEK-293), stably expressing the hCRTH2 receptor under the control of the cytomegalovirus promotor from a single insertion of the expression vector pcDNA5 (Invitrogen), are grown to confluency in DMEM (low glucose, Gibco) medium supplemented with 10% fetal calf serum (Bioconcept, Switzerland) under standard mammalian cell culture conditions (37° C. in a humidified atmosphere of 5% CO$_2$). Cells are detached from culture dishes using a dissociation buffer (0.02% EDTA in PBS, Gibco) for 1 min, and collected by centrifugation at 200 g at rt for 5 min in assay buffer (equal parts of Hank's BSS (HBSS, Bioconcept) and DMEM (low glucose, without phenol red, Gibco)). After incubation for 45 min (37° C. and 5% CO$_2$) in the presence of 1 µM Fluo-4 and 0.04% Pluronic F-127 (both Molecular Probes), and 20 mM HEPES (Gibco) in assay buffer, the cells are washed with and resuspended in assay buffer, then seeded onto 384-well FLIPR assay plates (Greiner) at 50,000 cells in 66 µl per well, and sedimented by centrifugation. Stock solutions of test compounds are made up at a concentration of 10 mM in DMSO, and serially diluted in assay buffer to concentrations required for inhibition dose response curves. Prostaglandin D$_2$ (Biomol, Plymouth Meeting, Pa.) is used as an agonist.

A FLIPR384 instrument (Molecular Devices) is operated according to the manufacturer's standard instructions, adding 4 µl of test compound dissolved at 10 mM in DMSO and diluted prior to the experiment in assay buffer to obtain the desired final concentration. 10 µl of 80 nM prostaglandin D$_2$ (Biomol, Plymouth Meeting, Pa.) in assay buffer, supplemented with 0.8% bovine serum albumin (fatty acid content <0.02%, Sigma), is then added to obtain a final concentration of 10 nM and 0.1%, respectively. Changes in fluorescence are monitored before and after the addition of test compounds at $\lambda_{ex}$488 nm and $\lambda_{em}$=540 nm. Emission peak values above base level after prostaglandin D$_2$ addition are exported after base line subtraction. Values are normalized to high-level control (no test compound added) after subtraction of base line value (no prostaglandin D$_2$ added). The program XLfit 3.0 (IDBS) is used to fit the data to a single site dose response curve of the equation $(A+((B-A)/(1+((C/x)^D))))$ and to calculate the IC$_{50}$ values.

The invention claimed is:

1. A compound of Formula I:

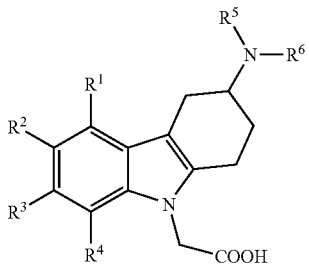

wherein
R$^1$, R$^2$, R$^3$ and R$^4$ are independently hydrogen, C$_{1-5}$-alkyl, C$_{1-5}$-alkoxy, alkenyl, halogen, nitro, cyano, halo-C$_{1-6}$-alkoxy, halo-C$_{1-6}$-alkyl, C$_{1-6}$-alkylsulfonyl, or formyl;
R$^5$ is a hydrogen, alkenyl, C$_{1-6}$-alkyl, cycloalkyl-C$_{1-4}$-alkyl, C$_{1-3}$-alkoxy-C$_{1-4}$-alkyl, aryl-C$_{1-4}$-alkyl, or aryloxy-C$_{1-4}$-alkyl; wherein the aryl is unsubstituted, mono- or di-substituted by C$_{1-2}$-alkylendioxy, C$_{1-4}$-alkoxy, C$_{1-4}$-alkyl, halogen, trifluoromethyl, or trifluoromethoxy; and
R$^6$ is a C$_{1-9}$-alkylaminocarbonyl; C$_{1-9}$-alkylaminothiocarbonyl; C$_{1-9}$-alkylcarbonyl; C$_{1-9}$-alkoxycarbonyl; arylalkenylcarbonyl; arylaminocarbonyl; arylaminothiocarbonyl; aryl-C$_{1-3}$-alkoxy-C$_{1-3}$-alkoxycarbonyl; aryl-C$_{1-3}$-alkoxycarbonyl; aryl-C$_{1-3}$-alkylaminocarbonyl; aryl-C$_{1-6}$-alkylcarbonyl; aryl-C$_{1-3}$-alkoxy-C$_{1-3}$-alkylcarbonyl; arylcarbonyl; arylcarbonyl-C$_{1-4}$-alkylcarbonyl; aryloxy-C$_{1-3}$-alkylcarbonyl; arylsulfonylaminocarbonyl; cycloalkyl-C$_{1-3}$-alkylcarbonyl; diaryl-C$_{1-3}$-alkylcarbonyl; heterocyclylcarbonyl; heteroaryl-C$_{1-3}$-alkylcarbonyl; heteroarylcarbonyl; aryl-C$_{3-6}$-cycloalkylcarbonyl; cycloalkylcarbonyl; or R$^7$—C$_{1-4}$-alkylcarbonyl wherein the bridging C$_{1-4}$-alkyl group of the R$^7$—C$_{1-4}$-alkylcarbonyl may additionally be mono-substituted with an aryl or disubstituted with a hydroxy, and wherein R$^7$ is an arylaminocarbonyl, heteroarylaminocarbonyl, C$_{1-6}$-alkylaminocarbonyl, or aryl-C$_{1-3}$-alkylaminocarbonyl;
further wherein the aryl is unsubstituted, mono- or di-substituted with a C$_{1-2}$-alkylendioxy; C$_{1-6}$-alkoxy; C$_{1-6}$-alkyl; C$_{1-6}$-alkylsulfonyl; phenyl which is unsubstituted, mono- or di-substituted by a halogen, trifluoromethyl, methoxy or methyl; naphthyl; phenyl-C$_{1-3}$-alkyl, wherein the phenyl group is unsubstituted, mono- or di-substituted independently with a halogen, trifluoromethyl, methoxy or methyl; naphthyl-C$_{1-3}$-alkyl; phenoxy, wherein the phenyl group is unsubstituted, mono- or di-substituted independently with a halogen, trifluoromethyl, methoxy or methyl; naphthyloxy; halogen; hydroxy; halo-C$_{1-6}$-alkyl; halo-C$_{1-6}$-alkoxy; C$_{1-6}$-alkylthio; or C$_{1-4}$-alkoxycarbonylamino;
or a salt thereof.

2. The compound according to claim 1, wherein R$^1$, R$^3$ and R$^4$ are hydrogen; or a salt thereof.

3. The compound according to claim 1, wherein R$^2$ is a hydrogen, trifluoromethyl, or halogen;
or a salt thereof.

4. The compound according to claim 1, wherein R$^5$ is a hydrogen; C$_{1-3}$-alkyl; cyclopropylmethyl; 2-methoxyethyl; phenyl-C$_{2-3}$-alkyl; or phenoxyethyl,
wherein the phenyl group is unsubstituted or mono-substituted with C$_{1-2}$-alkylendioxy, C$_{1-4}$-alkoxy, C$_{1-4}$-alkyl, halogen, trifluoromethyl, or trifluoromethoxy;
or a salt thereof.

5. The compound according to claim 1, wherein R$^6$ is a C$_{1-9}$-alkylaminocarbonyl; C$_{1-9}$-alkylcarbonyl; C$_{1-9}$-alkoxycarbonyl; arylalkenylcarbonyl; arylaminocarbonyl; aryl-C$_{1-3}$-alkoxy-C$_{1-3}$-alkoxycarbonyl; aryl-C$_{1-3}$-alkoxycarbonyl; aryl-C$_{1-3}$-alkylaminocarbonyl; aryl-C$_{1-6}$-alkylcarbonyl; aryl-C$_{1-3}$-alkoxy-C$_{1-3}$-alkylcarbonyl; arylcarbonyl; arylcarbonyl-C$_{1-4}$-alkylcarbonyl; aryloxy-C$_{1-3}$-alkylcarbonyl; arylsulfonylaminocarbonyl; cycloalkyl-C$_{1-3}$-alkylcarbonyl; diaryl-C$_{1-3}$-alkylcarbonyl; heterocyclylcarbonyl; heteroaryl-C$_{1-3}$-alkylcarbonyl; heteroarylcarbonyl; aryl-C$_{3-6}$-cycloalkylcarbonyl; cycloalkylcarbonyl; or R$^7$—C$_{1-4}$-alkylcarbonyl, wherein the bridging C$_{1-4}$-alkyl group of the R$^7$—C$_{1-4}$-alkylcarbonyl may additionally be mono-substituted with aryl, and R$^7$ is an arylaminocarbonyl, heteroarylaminocarbonyl, C$_{1-6}$-alkylaminocarbonyl, or aryl-C$_{1-3}$-alkylaminocarbonyl;
further wherein the aryl is unsubstituted, mono- or di-substituted independently with a C$_{1-2}$-alkylendioxy, C$_{1-6}$-alkoxy, C$_{1-6}$-alkyl, C$_{1-6}$-alkylsulfonyl, halogen, hydroxy, halo-C$_{1-6}$-alkyl, halo-C$_{1-5}$-alkoxy, C$_{1-6}$-alkylthio, or C$_{1-4}$-alkoxycarbonylamino;
or a salt thereof.

6. The compound according to claim 1, wherein R$^6$ is an aryl-C$_{1-2}$-alkoxycarbonyl; aryl-C$_{1-2}$-alkylaminocarbonyl; aryl-C$_{1-4}$-alkylcarbonyl; aryloxy-C$_{1-2}$-alkylcarbonyl; diaryl-C$_{2-3}$-alkylcarbonyl; or R$^7$—C$_{2-4}$-alkylcarbonyl, wherein the bridging C$_{2-4}$-alkyl group may additionally be mono-substituted with aryl, and R$^7$ is an arylaminocarbonyl or C$_{1-4}$-alkylaminocarbonyl;
further wherein the aryl is unsubstituted, mono- or di-substituted independently with a C$_{1-2}$-alkylendioxy, C$_{1-6}$-alkoxy, C$_{1-6}$-alkyl, C$_{1-6}$-alkylsulfonyl, halogen, hydroxy, trifluoromethyl, or trifluoromethoxy;
or a salt thereof.

7. The compound according to claim 1, wherein,
if R$^6$ is a group comprising a carbonyl group and one or more aryl moieties,
then R$^6$ comprises a bridging group between said carbonyl group and said one or more aryl moieties, further wherein said carbonyl moiety and at least one of said one or more aryl moieties are directly attached to different atoms of said bridging group;
or a salt thereof.

8. The compound according to claim 1, wherein
R$^6$ is a C$_{1-4}$-alkylcarbonyl or aryl-C$_{2-4}$-alkylcarbonyl, wherein the aryl is unsubstituted, mono- or di-substituted independently with a C$_{1-4}$-alkoxy, C$_{1-4}$-alkyl, halogen, or trifluoromethyl; and
R$^5$ is a phenyl-C$_{2-3}$-alkyl;
or a salt thereof.

9. The compound according to claim 1, wherein the compound is
(3S)-[3-(3,3-diphenyl-propionylamino)-6-fluoro-1,2,3,4-tetrahydro-9H-carbazol-9-yl]-acetic acid;
(3R)-{3-[2-(3-chloro-phenoxy)-acetylamino]-6-fluoro-1,2,3,4-tetrahydro-9H-carbazol-9-yl}-acetic acid;
(3S)-[6-fluoro-3-(3-phenyl-propionylamino)-1,2,3,4-tetrahydro-9H-carbazol-9-yl]-acetic acid;
(3R)-{3-[2-(4-chloro-phenoxy)-acetylamino]-6-fluoro-1,2,3,4-tetrahydro-9H-carbazol-9-yl}-acetic acid;
(3S)-{3-[3-(2-chloro-phenyl)-propionylamino]-6-fluoro-1,2,3,4-tetrahydro-9H-carbazol-9-yl}-acetic acid;

(3R)-(3-isobutoxycarbonylamino-1,2,3,4-tetrahydro-9H-carbazol-9-yl)-acetic acid;
(3R)-[6-fluoro-3-(3-phenyl-propionylamino)-1,2,3,4-tetrahydro-9H-carbazol-9-yl]-acetic acid;
(3S)-{3-[3-(4-chloro-phenyl)-propionylamino]-6-fluoro-1,2,3,4-tetrahydro-9H-carbazol-9-yl}-acetic acid;
(3R)-(3-benzyloxycarbonylamino-6-fluoro-1,2,3,4-tetrahydro-9H-carbazol-9-yl)-acetic acid;
(3S)-(3-benzyloxycarbonylamino-6-fluoro-1,2,3,4-tetrahydro-9H-carbazol-9-yl)-acetic acid;
(3S)-{3-[2-(4-chloro-phenoxy)-acetylamino]-6-fluoro-1,2,3,4-tetrahydro-9H-carbazol-9-yl}-acetic acid;
(3R)-{3-[2-(2-chloro-phenoxy)-acetylamino]-6-fluoro-1,2,3,4-tetrahydro-9H-carbazol-9-yl}-acetic acid;
(3S)-{3-[3-(3-chloro-phenyl)-propionylamino]-6-fluoro-1,2,3,4-tetrahydro-9H-carbazol-9-yl}-acetic acid;
(3S)-[6-fluoro-3-(4-oxo-4-phenyl-butyrylamino)-1,2,3,4-tetrahydro-9H-carbazol-9-yl]-acetic acid;
(3S)-[6-fluoro-3-(2-indan-2-yl-acetylamino)-1,2,3,4-tetrahydro-9H-carbazol-9-yl]-acetic acid;
(3S)-{3-[(2,3-dihydro-1H-indole-2-carbonyl)-amino]-6-fluoro-1,2,3,4-tetrahydro-9H-carbazol-9-yl}-acetic acid;
(3S)-(3-{[2-(4-chloro-phenyl)-acetyl]-ethyl-amino}-6-fluoro-1,2,3,4-tetrahydro-9H-carbazol-9-yl)-acetic acid;
(3R)-(3-propoxycarbonylamino-1,2,3,4-tetrahydro-9H-carbazol-9-yl)-acetic acid;
(3R)-[6-fluoro-3-(2-p-tolyloxy-acetylamino)-1,2,3,4-tetrahydro-9H-carbazol-9-yl]-acetic acid;
(3S)-{6-fluoro-3-[methyl-(3-phenyl-propionyl)-amino]-1,2,3,4-tetrahydro-9H-carbazol-9-yl}-acetic acid;
(3S)-[6-fluoro-3-(3-1H-indol-3-yl-propionylamino)-1,2,3,4-tetrahydro-9H-carbazol-9-yl]-acetic acid;
(3S)-[3-(3-benzo[1,3]dioxol-5-yl-propionylamino)-6-fluoro-1,2,3,4-tetrahydro-9H-carbazol-9-yl]-acetic acid;
(3S)-{6-fluoro-3-[ethyl-(3-phenyl-propionyl)-amino]-1,2,3,4-tetrahydro-9H-carbazol-9-yl}-acetic acid;
(3S)-{3-[2-(4-chloro-phenyl)-acetylamino]-6-fluoro-1,2,3,4-tetrahydro-9H-carbazol-9-yl}-acetic acid;
(3S)-[3-(2,3-diphenyl-propionylamino)-6-fluoro-1,2,3,4-tetrahydro-9H-carbazol-9-yl]-acetic acid;
(3R)-[6-fluoro-3-(2-phenoxy-acetylamino)-1,2,3,4-tetrahydro-9H-carbazol-9-yl]-acetic acid;
(3S)-{3-[3-(3,4-difluoro-phenyl)-propionylamino]-6-fluoro-1,2,3,4-tetrahydro-9H-carbazol-9-yl}-acetic acid;
(3S)-[3-(3-phenyl-propionylamino)-1,2,3,4-tetrahydro-9H-carbazol-9-yl]-acetic acid;
(3R)-[3-(2-benzyloxy-acetylamino)-1,2,3,4-tetrahydro-9H-carbazol-9-yl]-acetic acid;
(3S)-{6-fluoro-3-[3-(2-methoxy-phenyl)-propionylamino]-1,2,3,4-tetrahydro-9H-carbazol-9-yl}-acetic acid;
(3S)-{6-fluoro-3-[propyl-(3-phenyl-propionyl)-amino]-1,2,3,4-tetrahydro-9H-carbazol-9-yl}-acetic acid;
(3S)-[3-(2-benzyloxy-acetylamino)-1,2,3,4-tetrahydro-9H-carbazol-9-yl]-acetic acid;
(3R)-(3-benzyloxycarbonylamino-1,2,3,4-tetrahydro-9H-carbazol-9-yl)-acetic acid;
(3R)-{6-fluoro-3-[2-(4-methoxy-phenyl)-acetylamino]-1,2,3,4-tetrahydro-9H-carbazol-9-yl}-acetic acid;
(3R)-{3-[3-(4-chloro-phenyl)-propionylamino]-6-fluoro-1,2,3,4-tetrahydro-9H-carbazol-9-yl}-acetic acid;
(3S)-{3-[4-(4-bromo-phenyl)-4-oxo-butyrylamino]-6-fluoro-1,2,3,4-tetrahydro-9H-carbazol-9-yl}-acetic acid;
(3S)-(3-{[2-(4-chloro-phenyl)-acetyl]-propyl-amino}-6-fluoro-1,2,3,4-tetrahydro-9H-carbazol-9-yl)-acetic acid;
(3R)-(3-phenyl acetylamino-1,2,3,4-tetrahydro-9H-carbazol-9-yl)-acetic acid;
(3R)-{3-[3-(2-chloro-phenyl)-propionylamino]-6-fluoro-1,2,3,4-tetrahydro-9H-carbazol-9-yl}-acetic acid;
(3S)-{6-fluoro-3-[2-(4-trifluoromethyl-phenoxy)-acetylamino]-1,2,3,4-tetrahydro-9H-carbazol-9-yl}-acetic acid;
(3R)-(6-fluoro-3-phenylacetylamino-1,2,3,4-tetrahydro-9H-carbazol-9-yl)-acetic acid;
(3S)-{6-fluoro-3-[3-(2-hydroxy-phenyl)-propionylamino]-1,2,3,4-tetrahydro-9H-carbazol-9-yl}-acetic acid;
(3S)-[3-(3-1H-benzoimidazol-2-yl-propionylamino)-6-fluoro-1,2,3,4-tetrahydro-9H-carbazol-9-yl]-acetic acid;
(3S)-{6-fluoro-3-[3-(4-hydroxy-phenyl)-propionylamino]-1,2,3,4-tetrahydro-9H-carbazol-9-yl}-acetic acid;
(3S)-[6-fluoro-3-(2-p-tolyloxy-acetylamino)-1,2,3,4-tetrahydro-9H-carbazol-9-yl]-acetic acid;
(3R)-[6-fluoro-3-(2-p-tolyl-acetylamino)-1,2,3,4-tetrahydro-9H-carbazol-9-yl]-acetic acid;
(3R)-{3-[3-(3-chloro-phenyl)-propionylamino]-6-fluoro-1,2,3,4-tetrahydro-9H-carbazol-9-yl}-acetic acid;
(3R)-[3-(2-phenoxy-acetylamino)-1,2,3,4-tetrahydro-9H-carbazol-9-yl]-acetic acid;
(3S)-[6-fluoro-3-(3-p-tolyl-propionylamino)-1,2,3,4-tetrahydro-9H-carbazol-9-yl]-acetic acid;
(3S)-(3-benzyloxycarbonylamino-1,2,3,4-tetrahydro-9H-carbazol-9-yl)-acetic acid;
(3S)-[6-fluoro-3-(2-p-tolyl-acetylamino)-1,2,3,4-tetrahydro-9H-carbazol-9-yl]-acetic acid;
(3S)-[3-(3-phenethyl-ureido)-1,2,3,4-tetrahydro-9H-carbazol-9-yl]-acetic acid;
(3S)-{6-fluoro-3-[3-(3-hydroxy-phenyl)-propionylamino]-1,2,3,4-tetrahydro-9H-carbazol-9-yl}-acetic acid;
(3R)-[3-(2-benzyloxy-ethoxycarbonylamino)-1,2,3,4-tetrahydro-9H-carbazol-9-yl]-acetic acid;
(3S)-[6-fluoro-3-(3-naphthalen-2-yl-propionylamino)-1,2,3,4-tetrahydro-9H-carbazol-9-yl]-acetic acid;
(3S)-{6-fluoro-3-[4-(4-methanesulfonyl-phenyl)-4-oxo-butyrylamino]-1,2,3,4-tetrahydro-9H-carbazol-9-yl}-acetic acid;
(3S)-(3-{[2-(4-chloro-phenyl)-acetyl]-methyl-amino}-6-fluoro-1,2,3,4-tetrahydro-9H-carbazol-9-yl)-acetic acid;
(3S)-[3-(3-phenylsulfonyl-ureido)-1,2,3,4-tetrahydro-9H-carbazol-9-yl]-acetic acid;
(3S)-{6-fluoro-3-[3-(4-methoxy-phenyl)-propionylamino]-1,2,3,4-tetrahydro-9H-carbazol-9-yl}-acetic acid;
(3R)-[3-(3-phenyl-propionylamino)-1,2,3,4-tetrahydro-9H-carbazol-9-yl]-acetic acid;
(3R)-{3-[2-(4-chloro-phenyl)-acetylamino]-6-fluoro-1,2,3,4-tetrahydro-9H-carbazol-9-yl}-acetic acid;
(3R)-[6-fluoro-3-(3-p-tolyl-propionylamino)-1,2,3,4-tetrahydro-9H-carbazol-9-yl]-acetic acid;
(3R)-{6-fluoro-3-[3-(4-methoxy-phenyl)-propionylamino]-1,2,3,4-tetrahydro-9H-carbazol-9-yl}-acetic acid;

(3S)-{6-fluoro-3-[3-(4-hydroxy-3-methoxy-phenyl)-propionylamino]-1,2,3,4-tetrahydro-9H-carbazol-9-yl}-acetic acid;
(3S)-{6-fluoro-3-[2-(3-trifluoromethyl-phenyl)-acetylamino]-1,2,3,4-tetrahydro-9H-carbazol-9-yl}-acetic acid;
(3S)-{6-fluoro-3-[2-(4-methoxy-phenyl)-acetylamino]-1,2,3,4-tetrahydro-9H-carbazol-9-yl}-acetic acid;
(3R)-{3-[2-(3-chloro-phenyl)-acetylamino]-6-fluoro-1,2,3,4-tetrahydro-9H-carbazol-9-yl}-acetic acid;
(3S)-{6-fluoro-3-[2-(4-trifluoromethyl-phenyl)-acetylamino]-1,2,3,4-tetrahydro-9H-carbazol-9-yl}-acetic acid;
(3R)-(3-tert-butoxycarbonylamino-1,2,3,4-tetrahydro-9H-carbazol-9-yl)-acetic acid;
(3R)-{3-[2-(3,4-dichloro-phenyl)-acetylamino]-6-fluoro-1,2,3,4-tetrahydro-9H-carbazol-9-yl}-acetic acid;
(3S)-(3-isobutoxycarbonylamino-1,2,3,4-tetrahydro-9H-carbazol-9-yl)-acetic acid;
(3S)-{6-fluoro-3-[3-(3-methoxy-phenyl)-propionylamino]-1,2,3,4-tetrahydro-9H-carbazol-9-yl}-acetic acid;
(3S)-[6-fluoro-3-(2-phenoxy-acetylamino)-1,2,3,4-tetrahydro-9H-carbazol-9-yl]-acetic acid;
(3R)-{3-(3-phenethyl-ureido)-1,2,3,4-tetrahydro-9H-carbazol-9-yl}-acetic acid;
(3S)-[3-(2-benzyloxy-ethoxycarbonylamino)-1,2,3,4-tetrahydro-9H-carbazol-9-yl]-acetic acid;
(3S)-[3-(2-phenoxy-acetylamino)-1,2,3,4-tetrahydro-9H-carbazol-9-yl]-acetic acid;
(3S)-(3-propoxycarbonylamino-1,2,3,4-tetrahydro-9H-carbazol-9-yl)-acetic acid;
(3S)-[3-(2-thiophen-2-yl-acetylamino)-1,2,3,4-tetrahydro-9H-carbazol-9-yl]-acetic acid;
(3S)-(3-phenylacetylamino-1,2,3,4-tetrahydro-9H-carbazol-9-yl)-acetic acid;
(3R)-[3-(3-phenylsulfonyl-ureido)-1,2,3,4-tetrahydro-9H-carbazol-9-yl]-acetic acid;
(3S)-[3-(3-benzyl-ureido)-1,2,3,4-tetrahydro-9H-carbazol-9-yl]-acetic acid;
(3R)-[3-(3-naphthalen-1-yl-ureido)-1,2,3,4-tetrahydro-9H-carbazol-9-yl]-acetic acid;
(3S)-(3-decanoylamino-1,2,3,4-tetrahydro-9H-carbazol-9-yl)-acetic acid;
(3S)-[6-fluoro-3-(naphthalen-2-yl-acryloylamino)-1,2,3,4-tetrahydro-9H-carbazol-9-yl]acetic acid;
(3S)-{3-[2-(4-tert-butyl-phenyl)-acetylamino]-6-fluoro-1,2,3,4-tetrahydro-9H-carbazol-9-yl}-acetic acid;
(3R)-(3-benzyloxycarbonylamino-8-chloro-6-fluoro-1,2,3,4-tetrahydro-9H-carbazol-9-yl)-acetic acid;
(3S)-(3-benzyloxycarbonylamino-8-chloro-6-fluoro-1,2,3,4-tetrahydro-9H-carbazol-9-yl)-acetic acid;
(3S)-[6-fluoro-3-(3-pyridin-3-yl-propionylamino)-1,2,3,4-tetrahydro-9H-carbazol-9-yl]-acetic acid;
(3R)-[3-(3-benzyl-ureido)-1,2,3,4-tetrahydro-9H-carbazol-9-yl]-acetic acid;
(3S)-[3-(3-methyl-butyrylamino)-1,2,3,4-tetrahydro-9H-carbazol-9-yl]-acetic acid;
(3R)-{6-fluoro-3-[2-(4-trifluoromethyl-phenyl)-acetylamino]-1,2,3,4-tetrahydro-9H-carbazol-9-yl}-acetic acid;
(3S)-[3-(3-phenyl-ureido)-1,2,3,4-tetrahydro-9H-carbazol-9-yl]-acetic acid;
(3S)-[3-(3-cyclopentyl-propionylamino)-1,2,3,4-tetrahydro-9H-carbazol-9-yl]-acetic acid;
(3R)-[3-(2-thiophen-2-yl-acetylamino)-1,2,3,4-tetrahydro-9H-carbazol-9-yl]-acetic acid;
(3S)-(3-butyrylamino-1,2,3,4-tetrahydro-9H-carbazol-9-yl)-acetic acid;
(3R)-(3-benzyloxycarbonylamino-8-chloro-5-fluoro-1,2,3,4-tetrahydro-9H-carbazol-9-yl)-acetic acid;
(3S)-(3-benzyloxycarbonylamino-8-chloro-5-fluoro-1,2,3,4-tetrahydro-9H-carbazol-9-yl)-acetic acid;
(3S)-(3-heptanoylamino-1,2,3,4-tetrahydro-9H-carbazol-9-yl)-acetic acid;
(3R)-[3-(3-cyclopentyl-propionylamino)-1,2,3,4-tetrahydro-9H-carbazol-9-yl]-acetic acid;
(3R)-(3-decanoylamino-1,2,3,4-tetrahydro-9H-carbazol-9-yl)-acetic acid;
(3R)-(3-benzoylamino-1,2,3,4-tetrahydro-9H-carbazol-9-yl)-acetic acid;
(3R)-[3-(3-butyl-ureido)-1,2,3,4-tetrahydro-9H-carbazol-9-yl]-acetic acid;
(3R)-{6-fluoro-3-[(1H-indole-2-carbonyl)-amino]-1,2,3,4-tetrahydro-9H-carbazol-9-yl}-acetic acid;
(3R)-[3-(3-methyl-butyrylamino)-1,2,3,4-tetrahydro-9H-carbazol-9-yl]-acetic acid; or
(3S)-[3-(3-butyl-ureido)-1,2,3,4-tetrahydro-9H-carbazol-9-yl]-acetic acid;

or a salt thereof.

10. The compound according to claim 1, wherein the compound is:
(3R)-[3-(3-Benzyl-ureido)-6-fluoro-1,2,3,4-tetrahydro-9H-carbazol-9-yl]-acetic acid;
(3S)-[3-(3-Benzyl-ureido)-6-fluoro-1,2,3,4-tetrahydro-9H-carbazol-9-yl]-acetic acid;
(3S)-[6-Fluoro-3-(3-phenethyl-ureido)-1,2,3,4-tetrahydro-9H-carbazol-9-yl]-acetic acid;
(3R)-[3-(3-Benzyl-ureido)-8-chloro-6-fluoro-1,2,3,4-tetrahydro-9H-carbazol-9-yl]-acetic acid;
(3S)-[3-(3-Benzyl-ureido)-8-chloro-6-fluoro-1,2,3,4-tetrahydro-9H-carbazol-9-yl]-acetic acid;
(3R)-[8-Chloro-6-fluoro-3-(3-phenethyl-ureido)-1,2,3,4-tetrahydro-9H-carbazol-9-yl]-acetic acid;
(3S)-[8-Chloro-6-fluoro-3-(3-phenethyl-ureido)-1,2,3,4-tetrahydro-9H-carbazol-9-yl]-acetic acid;
(3R)-(3-Benzyloxycarbonylamino-6-trifluoromethyl-1,2,3,4-tetrahydro-9H-carbazol-9-yl)-acetic acid;
(3S)-(3-Benzyloxycarbonylamino-6-trifluoromethyl-1,2,3,4-tetrahydro-9H-carbazol-9-yl)-acetic acid;
(3R)-(3-Benzyloxylcarbonylamino-8-bromo-6-fluoro-1,2,3,4-tetrahydro-9H-carbazol-9-yl)-acetic acid;
(3S)-(3-Benzyloxycarbonylamino-8-bromo-6-fluoro-1,2,3,4-tetrahydro-9H-carbazol-9-yl)-acetic acid;
(3R)-(3-Benzyloxycarbonylamino-6-fluoro-8-vinyl-1,2,3,4-tetrahydro-9H-carbazol-9-yl)-acetic acid;
(3S)-(3-Benzyloxycarbonylamino-6-fluoro-8-vinyl-1,2,3,4-tetrahydro-9H-carbazol-9-yl)-acetic acid;
(3R)-(3-Benzyloxycarbonylamino-6-fluoro-8-methanesulfonyl-1,2,3,4-tetrahydro-9H-carbazol-9-yl)-acetic acid;
(3S)-(3-Benzyloxycarbonylamino-6-fluoro-8-methanesulfonyl-1,2,3,4-tetrahydro-9H-carbazol-9-yl)-acetic acid;
(3S)-(3-Benzyloxycarbonylamino-6-fluoro-8-methyl-1,2,3,4-tetrahydro-9H-carbazol-9-yl)-acetic acid;
(3S)-(3-Benzyloxycarbonylamino-7-chloro-6-fluoro-1,2,3,4-tetrahydro-9H-carbazol-9-yl)-acetic acid;
(3S)-(8-Allyl-3-benzyloxycarbonylamino-6-fluoro-1,2,3,4-tetrahydro-9H-carbazol-9-yl)-acetic acid;
(3R)-(3-Benzyloxycarbonylamino-8-chloro-1,2,3,4-tetrahydro-9H-carbazol-9-yl)-acetic acid;

(3R)-{3-[3-(2,4-Dimethoxy-phenyl)-propionylamino]-6-fluoro-1,2,3,4-tetrahydro-9H-carbazol-9-yl}-acetic acid;
(3S)-[6-Fluoro-3-(3-naphthalen-1-yl-propionylamino)-1,2,3,4-tetrahydro-9H-carbazol-9-yl]-acetic acid;
(3R)-{6-Fluoro-3-[2-(2-methoxy-phenoxy)-acetylamino]-1,2,3,4-tetrahydro-9H-carbazol-9-yl}-acetic acid;
(3S)-{6-Fluoro-3-[2-(2-methoxy-phenoxy)-acetylamino]-1,2,3,4-tetrahydro-9H-carbazol-9-yl}-acetic acid;
(3R)-{6-Fluoro-3-[3-(2-methylphenyl)-propionylamino]-1,2,3,4-tetrahydro-9H-carbazol-9-yl}-acetic acid;
(3S)-{6-Fluoro-3-[3-(2-methylphenyl)-propionylamino]-1,2,3,4-tetrahydro-9H-carbazol-9-yl}-acetic acid;
(3R)-{6-Fluoro-3-[3-(3-methylphenyl)-propionylamino]-1,2,3,4-tetrahydro-9H-carbazol-9-yl}-acetic acid;
(3S)-{6-Fluoro-3-[3-(3-methylphenyl)-propionylamino]-1,2,3,4-tetrahydro-9H-carbazol-9-yl}-acetic acid;
(3R)-{6-Fluoro-3-[3-(3-methoxy-phenyl)-propionylamino]-1,2,3,4-tetrahydro-9H-carbazol-9-yl}-acetic acid;
(3S)-{6-Fluoro-3-[3-(3-methoxy-phenyl)-propionylamino]-1,2,3,4-tetrahydro-9H-carbazol-9-yl}-acetic acid;
(3R)-{6-Fluoro-3-[2-(3-methoxy-phenoxy)-acetylamino]-1,2,3,4-tetrahydro-9H-carbazol-9-yl}-acetic acid;
(3S)-{6-Fluoro-3-[2-(3-methoxy-phenoxy)-acetylamino]-1,2,3,4-tetrahydro-9H-carbazol-9-yl}-acetic acid;
(3R)-{6-Fluoro-3-[2-(2-methylphenoxy)-acetylamino]-1,2,3,4-tetrahydro-9H-carbazol-9-yl}-acetic acid;
(3S)-{6-Fluoro-3-[2-(2-methylphenoxy)-acetylamino]-1,2,3,4-tetrahydro-9H-carbazol-9-yl}-acetic acid;
(3S)-{3-[3-(2,5-Dimethoxy-phenyl)-propionylamino]-6-fluoro-1,2,3,4-tetrahydro-9H-carbazol-9-yl}-acetic acid;
(3S)-{6-Fluoro-3-[3-(4-trifluoromethyl-phenyl)-propionylamino]-1,2,3,4-tetrahydro-9H-carbazol-9-yl}-acetic acid;
(3S)-{3-[3-(2,6-Dichloro-phenyl)-propionylamino]-6-fluoro-1,2,3,4-tetrahydro-9H-carbazol-9-yl}-acetic acid;
(3S)-{3-[3-(2,5-Bis-trifluoromethyl-phenyl)-propionylamino]-6-fluoro-1,2,3,4-tetrahydro-9H-carbazol-9-yl}-acetic acid;
(3S)-{6-Fluoro-3-[3-(4-methylsulfanyl-phenyl)-propionylamino]-1,2,3,4-tetrahydro-9H-carbazol-9-yl}-acetic acid;
(3S)-{6-Fluoro-3-[3-(4-iodo-phenyl)-propionylamino]-1,2,3,4-tetrahydro-9H-carbazol-9-yl}-acetic acid;
(3S)-{6-Fluoro-3-[3-(4-isopropyl-phenyl)-propionylamino]-1,2,3,4-tetrahydro-9H-carbazol-9-yl}-acetic acid;
(3S)-{6-Fluoro-3-[3-(3-trifluoromethyl-phenyl)-propionylamino]-1,2,3,4-tetrahydro-9H-carbazol-9-yl}-acetic acid;
(3S)-{3-[3-(2,4-Dichloro-phenyl)-propionylamino]-6-fluoro-1,2,3,4-tetrahydro-9H-carbazol-9-yl}-acetic acid;
(3S)-{6-Fluoro-3-[3-(4-fluoro-phenyl)-propionylamino]-1,2,3,4-tetrahydro-9H-carbazol-9-yl}-acetic acid;
(3S)-{3-[3-(3,5-Bis-trifluoromethyl-phenyl)-propionylamino]-6-fluoro-1,2,3,4-tetrahydro-9H-carbazol-9-yl}-acetic acid;
(3S)-{3-[3-(4-Ethyl-phenyl)-propionylamino]-6-fluoro-1,2,3,4-tetrahydro-9H-carbazol-9-yl}-acetic acid;
(3S)-{6-Fluoro-3-[3-(3-iodo-phenyl)-propionylamino]-1,2,3,4-tetrahydro-9H-carbazol-9-yl}-acetic acid;
(3S)-{6-Fluoro-3-[3-(4-methanesulfonyl-phenyl)-propionylamino]-1,2,3,4-tetrahydro-9H-carbazol-9-yl}-acetic acid;
(3S)-{3-[3-(2,3-Dimethoxy-phenyl)-propionylamino]-6-fluoro-1,2,3,4-tetrahydro-9H-carbazol-9-yl}-acetic acid;
(3S)-{3-[3-(2-Bromo-phenyl)-propionylamino]-6-fluoro-1,2,3,4-tetrahydro-9H-carbazol-9-yl}-acetic acid;
(3S)-{6-Fluoro-3-[3-(3-trifluoromethoxy-phenyl)-propionylamino]-1,2,3,4-tetrahydro-9H-carbazol-9-yl}-acetic acid;
(3S)-{3-[3-(2,4-Dimethyl-phenyl)-propionylamino]-6-fluoro-1,2,3,4-tetrahydro-9H-carbazol-9-yl}-acetic acid;
(3S)-{3-[3-(3-Bromo-phenyl)-propionylamino]-6-fluoro-1,2,3,4-tetrahydro-9H-carbazol-9-yl}-acetic acid;
(3S)-{3-[3-(3-tert-Butoxycarbonylamino-phenyl)-propionylamino]-6-fluoro-1,2,3,4-tetrahydro-9H-carbazol-9-yl}-acetic acid;
(3S)-{6-Fluoro-3-[(S)-3-(4-fluoro-phenyl)-2-phenyl-propionylamino]-1,2,3,4-tetrahydro-9H-carbazol-9-yl}-acetic acid;
(3S)-{6-Fluoro-3-[(S)-3-(4-methoxy-phenyl)-2-phenyl-propionylamino]-1,2,3,4-tetrahydro-9H-carbazol-9-yl}-acetic acid;
(3S)-{6-Fluoro-3-[3-(2-fluoro-phenyl)-propionylamino]-1,2,3,4-tetrahydro-9H-carbazol-9-yl}-acetic acid;
(3S)-(6-Fluoro-3-{[(2RS)-1,2,3,4-tetrahydro-naphthalene-2-carbonyl]-amino}-1,2,3,4-tetrahydro-9H-carbazol-9-yl)-acetic acid;
(3S)-(6-Fluoro-3-{[(2RS)-8-methoxy-1,2,3,4-tetrahydro-naphthalene-2-carbonyl]-amino}-1,2,3,4-tetrahydro-9H-carbazol-9-yl)-acetic acid;
(3S)-(6-Fluoro-3-{(2RS)-2-[(4-fluoro-phenylcarbamoyl)-methyl]-3-phenyl-propionylamino}-1,2,3,4-tetrahydro-9H-carbazol-9-yl)-acetic acid;
(3S)-{3-[(2RS)-2-Benzyl-3,3-dimethyl-butyrylamino]-6-fluoro-1,2,3,4-tetrahydro-9H-carbazol-9-yl}-acetic acid;
(3S)-(6-Fluoro-3-{[(2RS)-8-methoxy-1,2,3,4-tetrahydro-naphthalene-2-carbonyl]-amino}-1,2,3,4-tetrahydro-9H-carbazol-9-yl)-acetic acid;
(3S)-{6-Fluoro-3-[3-(3-fluoro-phenyl)-propionylamino]-1,2,3,4-tetrahydro-9H-carbazol-9-yl}-acetic acid;
(3S)-(6-Fluoro-3-{[(2RS)-8-methoxy-1,2,3,4-tetrahydro-naphthalene-2-carbonyl]-amino}-1,2,3,4-tetrahydro-9H-carbazol-9-yl)-acetic acid;
(3S)-{6-Fluoro-3-[(2R)-2-methyl-3-phenyl-propionylamino]-1,2,3,4-tetrahydro-9H-carbazol-9-yl}-acetic acid;
(3S)-[3-(2,2-Dimethyl-3-phenyl-propionylamino)-6-fluoro-1,2,3,4-tetrahydro-9H-carbazol-9-yl]-acetic acid;
(3S)-[6-Fluoro-3-(3-methyl-3-phenyl-butyrylamino)-1,2,3,4-tetrahydro-9H-carbazol-9-yl]-acetic acid;
(3S)-{6-Fluoro-3-[(3S)-3-phenyl-butyrylamino]-1,2,3,4-tetrahydro-9H-carbazol-9-yl}-acetic acid;
(3S)-[3-(2-Benzyloxy-acetylamino)-6-fluoro-1,2,3,4-tetrahydro-9H-carbazol-9-yl]-acetic acid;
(3S)-[6-Fluoro-3-(4-phenyl-butyrylamino)-1,2,3,4-tetrahydro-9H-carbazol-9-yl]-acetic acid;

(3S)-{3-[(2R,3R)-2,3-Dihydroxy-3-(2-methoxy-phenyl-carbamoyl)-propionylamino]-6-fluoro-1,2,3,4-tetrahydro-9H-carbazol-9-yl}-acetic acid;
(3R)-{8-Chloro-6-fluoro-3-[3-(2-methylphenyl)-propionylamino]-1,2,3,4-tetrahydro-9H-carbazol-9-yl}-acetic acid;
(3S)-{8-Chloro-6-fluoro-3-[3-(2-methylphenyl)-propionylamino]-1,2,3,4-tetrahydro-9H-carbazol-9-yl}-acetic acid;
(3R)-{8-Chloro-6-fluoro-3-[2-(2-methoxy-phenoxy)-acetylamino]-1,2,3,4-tetrahydro-9H-carbazol-9-yl}-acetic acid;
(3S)-{8-Chloro-6-fluoro-3-[2-(2-methoxy-phenoxy)-acetylamino]-1,2,3,4-tetrahydro-9H-carbazol-9-yl}-acetic acid;
(3R)-{8-Chloro-6-fluoro-3-[3-(3-hydroxy-phenyl)-propionylamino]-1,2,3,4-tetrahydro-9H-carbazol-9-yl}-acetic acid;
(3S)-{8-Chloro-6-fluoro-3-[3-(3-hydroxy-phenyl)-propionylamino]-1,2,3,4-tetrahydro-9H-carbazol-9-yl}-acetic acid;
(3R)-{8-Chloro-6-fluoro-3-[3-(3-methoxy-phenyl)-propionylamino]-1,2,3,4-tetrahydro-9H-carbazol-9-yl}-acetic acid;
(3S)-{8-Chloro-6-fluoro-3-[3-(3-methoxy-phenyl)-propionylamino]-1,2,3,4-tetrahydro-9H-carbazol-9-yl}-acetic acid;
(3R)-{8-Chloro-6-fluoro-3-[3-(3-methylphenyl)-propionylamino]-1,2,3,4-tetrahydro-9H-carbazol-9-yl}-acetic acid;
(3S)-{8-Chloro-6-fluoro-3-[3-(3-methylphenyl)-propionylamino]-1,2,3,4-tetrahydro-9H-carbazol-9-yl}-acetic acid;
(3R)-{8-Chloro-6-fluoro-3-[3-(2-hydroxy-phenyl)-propionylamino]-1,2,3,4-tetrahydro-9H-carbazol-9-yl}-acetic acid;
(3S)-{8-Chloro-6-fluoro-3-[3-(2-hydroxy-phenyl)-propionylamino]-1,2,3,4-tetrahydro-9H-carbazol-9-yl}-acetic acid;
(3R)-[8-Chloro-6-fluoro-3-(3-phenyl-propionylamino)-1,2,3,4-tetrahydro-9H-carbazol-9-yl]-acetic acid;
(3S)-[8-Chloro-6-fluoro-3-(3-phenyl-propionylamino)-1,2,3,4-tetrahydro-9H-carbazol-9-yl]-acetic acid;
(3R)-{8-Chloro-6-fluoro-3-[3-(2-methoxy-phenyl)-propionylamino]-1,2,3,4-tetrahydro-9H-carbazol-9-yl}-acetic acid;
(3S)-{8-Chloro-6-fluoro-3-[3-(2-methoxy-phenyl)-propionylamino]-1,2,3,4-tetrahydro-9H-carbazol-9-yl}-acetic acid;
(3R)-{8-Chloro-3-[3-(3-chloro-phenyl)-propionylamino]-6-fluoro-1,2,3,4-tetrahydro-9H-carbazol-9-yl}-acetic acid;
(3S)-{8-Chloro-3-[3-(3-chloro-phenyl)-propionylamino]-6-fluoro-1,2,3,4-tetrahydro-9H-carbazol-9-yl}-acetic acid;
(3R)-[8-Chloro-6-fluoro-3-(3-1H-indol-3-yl-propionylamino)-1,2,3,4-tetrahydro-9H-carbazol-9-yl]-acetic acid;
(3S)-[₈-Chloro-6-fluoro-3-(3-1H-indol-3-yl-propionylamino)-1,2,3,4-tetrahydro-9H-carbazol-9-yl]-acetic acid;
(3R)-{8-Chloro-3-[2-(2-chloro-phenoxy)-acetylamino]-6-fluoro-1,2,3,4-tetrahydro-9H-carbazol-9-yl}-acetic acid;
(3S)-{8-Chloro-3-[2-(2-chloro-phenoxy)-acetylamino]-6-fluoro-1,2,3,4-tetrahydro-9H-carbazol-9-yl}-acetic acid;
(3R)-{8-Chloro-6-fluoro-3-[2-(2-methylphenyl)-oxy-acetylamino]-1,2,3,4-tetrahydro-9H-carbazol-9-yl}-acetic acid;
(3S)-{8-Chloro-6-fluoro-3-[2-(2-methylphenyl)-oxy-acetylamino]-1,2,3,4-tetrahydro-9H-carbazol-9-yl}-acetic acid;
(3R)-[3-(3-Benzo[1,3]dioxol-5-yl-propionylamino)-8-chloro-6-fluoro-1,2,3,4-tetrahydro-9H-carbazol-9-yl]-acetic acid;
(3S)-[3-(3-Benzo[1,3]dioxol-5-yl-propionylamino)-8-chloro-6-fluoro-1,2,3,4-tetrahydro-9H-carbazol-9-yl]-acetic acid;
(3R)-{8-Chloro-6-fluoro-3-[2-(3-methoxy-phenoxy)-acetylamino]-1,2,3,4-tetrahydro-9H-carbazol-9-yl}-acetic acid;
(3S)-{8-Chloro-6-fluoro-3-[2-(3-methoxy-phenoxy)-acetylamino]-1,2,3,4-tetrahydro-9H-carbazol-9-yl}-acetic acid;
(3R)-{8-Chloro-3-[2-(3-chloro-phenoxy)-acetylamino]-6-fluoro-1,2,3,4-tetrahydro-9H-carbazol-9-yl}-acetic acid;
(3S)-{8-Chloro-3-[2-(3-chloro-phenoxy)-acetylamino]-6-fluoro-1,2,3,4-tetrahydro-9H-carbazol-9-yl}-acetic acid;
(3R)-{8-Chloro-3-[3-(2-chloro-phenyl)-propionylamino]-6-fluoro-1,2,3,4-tetrahydro-9H-carbazol-9-yl}-acetic acid;
(3S)-{8-Chloro-3-[3-(2-chloro-phenyl)-propionylamino]-6-fluoro-1,2,3,4-tetrahydro-9H-carbazol-9-yl}-acetic acid;
(3R)-[8-Chloro-6-fluoro-3-(2-indan-2-yl-acetylamino)-1,2,3,4-tetrahydro-9H-carbazol-9-yl]-acetic acid;
(3S)-[8-Chloro-6-fluoro-3-(2-indan-2-yl-acetylamino)-1,2,3,4-tetrahydro-9H-carbazol-9-yl]-acetic acid;
(3R)-[6-Fluoro-3-(1-methyl-3-phenethyl-ureido)-1,2,3,4-tetrahydro-9H-carbazol-9-yl]-acetic acid;
(3S)-{3-[3-(2-Chloro-benzyl)-1-methyl-ureido]-6-fluoro-1,2,3,4-tetrahydro-9H-carbazol-9-yl}-acetic acid;
(3S)-{3-(3-Benzyl-1-methyl-ureido)-6-fluoro-1,2,3,4-tetrahydro-9H-carbazol-9-yl]-acetic acid;
(3S)-[3-(Benzyloxycarbonyl-methyl-amino)-6-fluoro-1,2,3,4-tetrahydro-9H-carbazol-9-yl]-acetic acid;
{(3S)-3-[(2-Chloro-benzyloxycarbonyl)-methyl-amino]-6-fluoro-1,2,3,4-tetrahydro-9H-carbazol-9-yl}-acetic acid;
(3S)-(6-Fluoro-3-{[2-(4-methoxy-phenyl)-acetyl]-methyl-amino}-1,2,3,4-tetrahydro-9H-carbazol-9-yl)-acetic acid;
(3S)-(6-Fluoro-3-{methyl-[2-(4-methylphenyl)-acetyl]-amino}-1,2,3,4-tetrahydro-9H-carbazol-9-yl)-acetic acid;
(3S)-(6-Fluoro-3-{[2-(2-methoxy-phenyl)-acetyl]-methyl-amino}-1,2,3,4-tetrahydro-9H-carbazol-9-yl)-acetic acid;
(3S)-{6-Fluoro-3-[(2-indan-2-yl-acetyl)-methyl-amino]-1,2,3,4-tetrahydro-9H-carbazol-9-yl}-acetic acid;
(3S)-(3-{[2-(3-Chloro-phenyl)-acetyl]-methyl-amino}-6-fluoro-1,2,3,4-tetrahydro-9H-carbazol-9-yl)-acetic acid;
(3S)-(6-Fluoro-3-{methyl-[2-(3-methylphenyl)-acetyl]-amino}-1,2,3,4-tetrahydro-9H-carbazol-9-yl)-acetic acid;
(3S)-(6-Fluoro-3-{[2-(3-methoxy-phenyl)-acetyl]-methyl-amino}-1,2,3,4-tetrahydro-9H-carbazol-9-yl)-acetic acid;

(3S)-(3-{[2-(2-Chloro-phenoxy)-acetyl]-methyl-amino}-6-fluoro-1,2,3,4-tetrahydro-9H-carbazol-9-yl)-acetic acid;

(3S)-(3-{[2-(4-Chloro-phenoxy)-acetyl]-methyl-amino}-6-fluoro-1,2,3,4-tetrahydro-9H-carbazol-9-yl)-acetic acid;

(3S)-(6-Fluoro-3-{[3-(3-methoxy-phenyl)-propionyl]-methyl-amino}-1,2,3,4-tetrahydro-9H-carbazol-9-yl)-acetic acid;

(3S)-(6-Fluoro-3-{methyl-[2-(2-methylphenyl)-acetyl]-amino}-1,2,3,4-tetrahydro-9H-carbazol-9-yl)-acetic acid;

(3S)-{3-[(3,3-Diphenyl-propionyl)-methyl-amino]-6-fluoro-1,2,3,4-tetrahydro-9H-carbazol-9-yl}-acetic acid;

(3S)-(6-Fluoro-3-{[3-(2-methoxy-phenyl)-propionyl]-methyl-amino}-1,2,3,4-tetrahydro-9H-carbazol-9-yl)-acetic acid;

(3S)-{6-Fluoro-3-[(3-1H-indol-3-yl-propionyl)-methyl-amino]-1,2,3,4-tetrahydro-9H-carbazol-9-yl}-acetic acid;

(3S)-{3-[(2-Benzyloxy-acetyl)-methyl-amino]-6-fluoro-1,2,3,4-tetrahydro-9H-carbazol-9-yl}-acetic acid;

(3S)-{3-[(2,3-Diphenyl-propionyl)-methyl-amino]-6-fluoro-1,2,3,4-tetrahydro-9H-carbazol-9-yl}-acetic acid;

(3S)-{6-Fluoro-3-[[3-(2-methoxy-phenyl)-propionyl]-(3-phenyl-propyl)-amino]-1,2,3,4-tetrahydro-9H-carbazol-9-yl}-acetic acid;

(3S)-{3-[Acetyl-(3-phenyl-propyl)-amino]-6-fluoro-1,2,3,4-tetrahydro-9H-carbazol-9-yl}-acetic acid;

(3S)-{3-[3-Benzyl-(1-cyclopropylmethyl)-ureido]-6-fluoro-1,2,3,4-tetrahydro-9H-carbazol-9-yl}-acetic acid;

(3S)-[3-(Benzyloxycarbonyl-cyclopropylmethyl-amino)-6-fluoro-1,2,3,4-tetrahydro-9H-carbazol-9-yl]-acetic acid;

(3S)-{3-[Cyclopropylmethyl-(3-phenyl-propionyl)-amino]-6-fluoro-1,2,3,4-tetrahydro-9H-carbazol-9-yl}-acetic acid;

(3S)-{3-[Cyclopropylmethyl-((S)-2-methyl-3-phenyl-propionyl)-amino]-6-fluoro-1,2,3,4-tetrahydro-9H-carbazol-9-yl}-acetic acid;

(3S)-(3-{Cyclopropylmethyl-[3-(2-methoxy-phenyl)-propionyl]-amino}-6-fluoro-1,2,3,4-tetrahydro-9H-carbazol-9-yl)-acetic acid;

(3S)-{3-[2-(3-Chloro-phenoxy)-acetyl]-cyclopropylmethyl-amino}-6-fluoro-1,2,3,4-tetrahydro-9H-carbazol-9-yl)-acetic acid;

(3S)-{3-[Cyclopropylmethyl-(3,3-diphenyl-propionyl)-amino]-6-fluoro-1,2,3,4-tetrahydro-9H-carbazol-9-yl}-acetic acid;

(3S)-{3-[Cyclopropylmethyl-(2-naphthalen-1-yl-acetyl)-amino]-6-fluoro-1,2,3,4-tetrahydro-9H-carbazol-9-yl}-acetic acid;

(3S)-(3-{Benzyloxycarbonyl-[2-(4-trifluoromethyl-phenoxy)-ethyl]-amino}-6-fluoro-1,2,3,4-tetrahydro-9H-carbazol-9-yl)-acetic acid;

(3S)-(3-{Acetyl-[2-(4-trifluoromethyl-phenoxy)-ethyl]-amino}-6-fluoro-1,2,3,4-tetrahydro-9H-carbazol-9-yl)-acetic acid;

(3S)-(6-Fluoro-3-{propionyl-[2-(4-trifluoromethyl-phenoxy)-ethyl]amino}-1,2,3,4-tetrahydro-9H-carbazol-9-yl)-acetic acid;

(3S)-(6-Fluoro-3-{(3-phenyl-propionyl)-[2-(4-trifluoromethyl-phenoxy)-ethyl]-amino}-1,2,3,4-tetrahydro-9H-carbazol-9-yl)-acetic acid;

(3S)-(6-Fluoro-3-{[3-(2-methoxy-phenyl)-propionyl]-[2-(4-trifluoromethyl-phenoxy)-ethyl]-amino}-1,2,3,4-tetrahydro-9H-carbazol-9-yl)-acetic acid;

(3S)-{6-Fluoro-3-[(2-phenoxy-ethyl)-(3-phenyl-propionyl)-amino]-1,2,3,4-tetrahydro-9H-carbazol-9-yl}-acetic acid;

(3S)-{6-Fluoro-3-[((S)-2-methyl-3-phenyl-propionyl)-(2-phenoxy-ethyl)-amino]-1,2,3,4-tetrahydro-9H-carbazol-9-yl}-acetic acid;

(3S)-{6-Fluoro-3-[[3-(2-methoxy-phenyl)-propionyl]-(2-phenoxy-ethyl)-amino]-1,2,3,4-tetrahydro-9H-carbazol-9-yl}-acetic acid;

(3S)-{3-[Acetyl-(2-phenoxy-ethyl)-amino]-6-fluoro-1,2,3,4-tetrahydro-9H-carbazol-9-yl}-acetic acid;

(3S)-{3-[3-Benzyl-1-(2-methoxy-ethyl)-ureido]-6-fluoro-1,2,3,4-tetrahydro-9H-carbazol-9-yl}-acetic acid;

(3S)-{3-[Benzyloxycarbonyl-(2-methoxy-ethyl)-amino]-6-fluoro-1,2,3,4-tetrahydro-9H-carbazol-9-yl}-acetic acid;

(3S)-{6-Fluoro-3-[(2-methoxy-ethyl)-(3-phenyl-propionyl)-amino]-1,2,3,4-tetrahydro-9H-carbazol-9-yl}-acetic acid;

(3S)-{6-Fluoro-3-[(2-methoxy-ethyl)-((S)-2-methyl-3-phenyl-propionyl)-amino]-1,2,3,4-tetrahydro-9H-carbazol-9-yl}-acetic acid;

(3S)-(6-Fluoro-3-{(2-methoxy-ethyl)-[3-(2-methoxy-phenyl)-propionyl]-amino}-1,2,3,4-tetrahydro-9H-carbazol-9-yl)-acetic acid;

(3S)-{3-[[2-(3-Chloro-phenoxy)-acetyl]-(2-methoxy-ethyl)-amino]-6-fluoro-1,2,3,4-tetrahydro-9H-carbazol-9-yl}-acetic acid;

(3S)-{3-[(3,3-Diphenyl-propionyl)-(2-methoxy-ethyl)-amino]-6-fluoro-1,2,3,4-tetrahydro-9H-carbazol-9-yl}-acetic acid;

(3S)-{6-Fluoro-3-[(2-methoxy-ethyl)-(2-naphthalen-1-yl-acetyl)-amino]-1,2,3,4-tetrahydro-9H-carbazol-9-yl}-acetic acid;

(3S)-(6-Fluoro-3-{[(2S)-2-methyl-3-phenyl-propionyl]-phenethyl-amino}-1,2,3,4-tetrahydro-9H-carbazol-9-yl)-acetic acid;

(3S)-(6-Fluoro-3-{[3-(2-methoxy-phenyl)-propionyl]-phenethyl-amino}-1,2,3,4-tetrahydro-9H-carbazol-9-yl)-acetic acid;

(3S)-[3-(Acetyl-phenethyl-amino)-6-fluoro-1,2,3,4-tetrahydro-9H-carbazol-9-yl]-acetic acid;

(3S)-{6-Fluoro-3-[(2-naphthalen-1-yl-acetyl)-phenethyl-amino]-1,2,3,4-tetrahydro-9H-carbazol-9-yl}-acetic acid;

(3S)-{6-Fluoro-3-[phenethyl-(3-phenyl-propionyl)-amino]-1,2,3,4-tetrahydro-9H-carbazol-9-yl}-acetic acid;

(3S)-[3-(3-Benzyl-1-naphthalen-1-ylmethyl-ureido)-6-fluoro-1,2,3,4-tetrahydro-9H-carbazol-9-yl]-acetic acid;

(3S)-[3-(Benzyloxycarbonyl-naphthalen-1-ylmethyl-amino)-6-fluoro-1,2,3,4-tetrahydro-9H-carbazol-9-yl]-acetic acid;

(3S)-{6-Fluoro-3-[naphthalen-1-ylmethyl-(3-phenyl-propionyl)-amino]-1,2,3,4-tetrahydro-9H-carbazol-9-yl}-acetic acid;

(3S)-{6-Fluoro-3-[((S)-2-methyl-3-phenyl-propionyl)-naphthalen-1-ylmethyl-amino]-1,2,3,4-tetrahydro-9H-carbazol-9-yl}-acetic acid;

(3S)-(6-Fluoro-3-{[3-(2-methoxy-phenyl)-propionyl]-naphthalen-1-ylmethyl-amino}-1,2,3,4-tetrahydro-9H-carbazol-9-yl)-acetic acid;

(3S)-{3-[(3,3-Diphenyl-propionyl)-naphthalen-1-ylm-ethyl-amino]-6-fluoro-1,2,3,4-tetrahydro-9H-carbazol-9-yl}-acetic acid;

(3S)-[3-(Acetyl-naphthalen-1-ylmethyl-amino)-6-fluoro-1,2,3,4-tetrahydro-9H-carbazol-9-yl]-acetic acid;

(3S)-[6-Fluoro-3-(naphthalen-1-ylmethyl-propionyl-amino)-1,2,3,4-tetrahydro-9H-carbazol-9-yl]-acetic acid;

(3S)-{3-[(RS)-2-Benzyl-3-(2-methylphenyl)-carbamoyl-propionylamino]-6-fluoro-1,2,3,4-tetrahydro-9H-carbazol-9-yl}-acetic acid;

(3S)-{3-[(RS)-2-Benzyl-3-(3-methoxy-phenylcarbamoyl)-propionylamino]-6-fluoro-1,2,3,4-tetrahydro-9H-carbazol-9-yl}-acetic acid;

(3S)-{3-[(RS)-2-Benzyl-3-(4-chloro-phenylcarbamoyl)-propionylamino]-6-fluoro-1,2,3,4-tetrahydro-9H-carbazol-9-yl}-acetic acid;

(3S)-{3-[(RS)-2-Benzyl-3-(4-fluoro-benzylcarbamoyl)-propionylamino]-6-fluoro-1,2,3,4-tetrahydro-9H-carbazol-9-yl}-acetic acid;

[(3S)-3-((RS)-2-Benzyl-3-propylcarbamoyl-propionylamino)-6-fluoro-1,2,3,4-tetrahydro-9H-carbazol-9-yl]-acetic acid;

(3S)-[6-Fluoro-3-(3-thiophen-2-yl-propionylamino)-1,2,3,4-tetrahydro-9H-carbazol-9-yl]-acetic acid;

(3S)-{3-[3-(3-Chloro-isoxazol-5-yl)-propionylamino]-6-fluoro-1,2,3,4-tetrahydro-9H-carbazol-9-yl}-acetic acid;

(3S)-[6-Fluoro-3-(3-pyrimidin-2-yl-propionylamino)-1,2,3,4-tetrahydro-9H-carbazol-9-yl]-acetic acid;

(3S)-{6-Fluoro-3-[3-phenyl-4-([1,3,4]thiadiazol-2-ylcarbamoyl)-butyrylamino]-1,2,3,4-tetrahydro-9H-carbazol-9-yl}-acetic acid;

(3S)-[3-(1,3-Dibenzyl-ureido)-6-fluoro-1,2,3,4-tetrahydro-9H-carbazol-9-yl]-acetic acid;

(3S)-(3-{Acetyl-[2-(2-fluoro-phenyl)-ethyl]-amino}-6-fluoro-1,2,3,4-tetrahydro-9H-carbazol-9-yl)-acetic acid;

(3S)-(3-{Acetyl-[2-(3-fluoro-phenyl)-ethyl]-amino}-6-fluoro-1,2,3,4-tetrahydro-9H-carbazol-9-yl)-acetic acid;

(3S)-[3-(3-Benzyl-1-cyclohexylmethyl-ureido)-6-fluoro-1,2,3,4-tetrahydro-9H-carbazol-9-yl]-acetic acid; or (3S)-(3-{Cyclohexylmethyl-[3-(2-methoxy-phenyl)-propionyl]-amino}-6-fluoro-1,2,3,4-tetrahydro-9H-carbazol-9-yl)-acetic acid;

or a salt thereof.

11. A pharmaceutical composition, comprising a compound according to claim 1, or a pharmaceutically acceptable salt thereof, and a pharmaceutically acceptable carrier.

12. A medicament, comprising a compound according to claim 1, or a pharmaceutically acceptable salt thereof.

13. A method of antagonizing a CRTH2 receptor, comprising the step of administering an effective amount of a compound according to claim 1, or a pharmaceutically acceptable salt thereof, to a patient in need thereof.

14. The method of claim 13, wherein said patient has a disease or disorder that comprises allergic asthma, rhinitis, allergic rhinitis, chronic obstructive pulmonary disease, dermatitis, inflammatory bowel disease, rheumatoid arthritis, allergic nephritis, conjunctivitis, atopic dermatitis, bronchial asthma, food allergy, systemic mast cell disorders, anaphylactic shock, urticaria, eczema, itching, inflammation, ischemia-reperfusion injury, cerebrovascular disorders, pleuritis, ulcerative colitis, an eosinophil-related disease, or a basophil-related disease.

15. The method of claim 14, wherein said patient has an eosinophil-related disease comprising Churg-Strauss syndrome or sinusitis.

16. The method of claim 14, wherein said patient has a basophil-related disease comprising basophilic leukemia or basophilic leukocytosis.

17. The compound according to claim 1, wherein
$R^5$ is hydrogen, methyl, ethyl, or n-propyl;
or a salt thereof.

18. The compound according to claim 2, wherein
$R^5$ is hydrogen, methyl, ethyl, or n-propyl;
or a salt thereof.

19. The compound according to claim 1, wherein $R^6$ is aryl-$C_{1-3}$-alkoxycarbonyl; aryl-$C_{1-3}$-alkylaminocarbonyl; aryl-$C_{1-6}$-alkylcarbonyl; aryl-$C_{1-3}$-alkoxy-$C_{1-3}$-alkylcarbonyl; arylcarbonyl-$C_{1-4}$-alkylcarbonyl; aryloxy-$C_{1-3}$-alkylcarbonyl; cycloalkyl-$C_{1-3}$-alkylcarbonyl; diaryl-$C_{1-3}$-alkylcarbonyl; aryl-$C_{3-6}$-cycloalkylcarbonyl; or $R^7$—$C_{1-4}$-alkylcarbonyl wherein the bridging $C_{1-4}$-alkyl group of the $R^7$—$C_{1-4}$-alkylcarbonyl may additionally be mono-substituted with an aryl, and wherein $R^7$ is an arylaminocarbonyl, heteroarylaminocarbonyl, $C_{1-6}$-alkylaminocarbonyl, or aryl-$C_{1-3}$-alkylaminocarbonyl; further wherein the aryl is unsubstituted, mono- or di-substituted with a $C_{1-2}$-alkylendioxy; $C_{1-6}$-alkoxy; $C_{1-6}$-alkyl; $C_{1-6}$-alkylsulfonyl; halogen; hydroxy; halo-$C_{1-6}$-alkyl; halo-$C_{1-6}$-alkoxy; $C_{1-6}$-alkylthio, or $C_{1-4}$-alkoxycarbonylamino;
or a salt thereof.

20. The compound according to claim 17, wherein $R^6$ is aryl-$C_{1-3}$-alkoxycarbonyl; aryl-$C_{1-3}$-alkylaminocarbonyl; aryl-$C_{1-6}$-alkylcarbonyl; aryl-$C_{1-3}$-alkoxy-$C_{1-3}$-alkylcarbonyl; arylcarbonyl-$C_{1-4}$-alkylcarbonyl; aryloxy-$C_{1-3}$-alkylcarbonyl; cycloalkyl-$C_{1-3}$-alkylcarbonyl; diaryl-$C_{1-3}$-alkylcarbonyl; aryl-$C_{3-6}$-cycloalkylcarbonyl; or $R^7$—$C_{1-4}$-alkylcarbonyl wherein the bridging $C_{1-4}$-alkyl group of the $R^7$—$C_{1-4}$-alkylcarbonyl may additionally be mono-substituted with an aryl, and wherein $R^7$ is an arylaminocarbonyl, heteroarylaminocarbonyl, $C_{1-6}$-alkylaminocarbonyl, or aryl-$C_{1-3}$-alkylaminocarbonyl; further wherein the aryl is unsubstituted, mono- or di-substituted with a $C_{1-2}$-alkylendioxy; $C_{1-6}$-alkoxy; $C_{1-6}$-alkyl; $C_{1-6}$-alkylsulfonyl; halogen; hydroxy; halo-$C_{1-6}$-alkyl; halo-$C_{1-6}$-alkoxy; $C_{1-6}$-alkylthio, or $C_{1-4}$-alkoxycarbonylamino;
or a salt thereof.

21. The compound according to claim 18, wherein $R^6$ is aryl-$C_{1-3}$-alkoxycarbonyl; aryl-$C_{1-3}$-alkylaminocarbonyl; aryl-$C_{1-6}$-alkylcarbonyl; aryl-$C_{1-3}$-alkoxy-$C_{1-3}$-alkylcarbonyl; arylcarbonyl-$C_{1-4}$-alkylcarbonyl; aryloxy-$C_{1-3}$-alkylcarbonyl; cycloalkyl-$C_{1-3}$-alkylcarbonyl; diaryl-$C_{1-3}$-alkylcarbonyl; aryl-$C_{3-6}$-cycloalkylcarbonyl; or $R^7$—$C_{1-4}$-alkylcarbonyl wherein the bridging $C_{1-4}$-alkyl group of the $R^7$—$C_{1-4}$-alkylcarbonyl may additionally be mono-substituted with an aryl, and wherein $R^7$ is an arylaminocarbonyl, heteroarylaminocarbonyl, $C_{1-6}$-alkylaminocarbonyl, or aryl-$C_{1-3}$-alkylaminocarbonyl; further wherein the aryl is unsubstituted, mono- or di-substituted with a $C_{1-2}$-alkylendioxy; $C_{1-6}$-alkoxy; $C_{1-6}$-alkyl; $C_{1-6}$-alkylsulfonyl; halogen; hydroxy; halo-$C_{1-6}$-alkyl; halo-$C_{1-6}$-alkoxy; $C_{1-6}$-alkylthio, or $C_{1-4}$-alkoxycarbonylamino;
or a salt thereof.

22. The compound according to claim 1, wherein $R^6$ represents $C_{1-9}$-alkylaminocarbonyl; $C_{1-9}$-alkylcarbonyl; or $C_{1-9}$-alkoxycarbonyl;
or a salt thereof.

23. The compound according to claim 2, wherein $R^6$ represents $C_{1-9}$-alkylaminocarbonyl; $C_{1-9}$-alkylcarbonyl; or $C_{1-9}$-alkoxycarbonyl;
or a salt thereof.

* * * * *